US009550975B2

(12) United States Patent
Dezawa et al.

(10) Patent No.: US 9,550,975 B2
(45) Date of Patent: *Jan. 24, 2017

(54) SSEA-3 PLURIPOTENT STEM CELL ISOLATED FROM BODY TISSUE

(76) Inventors: Mari Dezawa, Miyagi (JP); Yoshinori Fujiyoshi, Kyoto (JP); Youichi Nabeshima, Kyoto (JP); Shohei Wakao, Miyagi (JP)

( * ) Notice: Subject to any disclaimer, the term of this patent is extended or adjusted under 35 U.S.C. 154(b) by 158 days.

This patent is subject to a terminal disclaimer.

(21) Appl. No.: 12/836,264

(22) Filed: Jul. 14, 2010

(65) Prior Publication Data

US 2011/0070647 A1    Mar. 24, 2011

Related U.S. Application Data

(60) Provisional application No. 61/213,788, filed on Jul. 15, 2009, provisional application No. 61/290,159, filed on Dec. 24, 2009.

(51) Int. Cl.

| | | |
|---|---|---|
| C12N 15/02 | (2006.01) | |
| C12N 5/00 | (2006.01) | |
| C12N 5/074 | (2010.01) | |
| C12N 15/113 | (2010.01) | |
| C12N 5/0775 | (2010.01) | |
| C12N 15/86 | (2006.01) | |
| C12N 5/073 | (2010.01) | |
| A61K 35/50 | (2015.01) | |
| A61K 35/12 | (2015.01) | |
| A61K 35/28 | (2015.01) | |

(52) U.S. Cl.
CPC ........... *C12N 5/0607* (2013.01); *C12N 5/0696* (2013.01); *A61K 35/12* (2013.01); *A61K 35/28* (2013.01); *A61K 35/50* (2013.01); *C12N 5/0605* (2013.01); *C12N 5/0662* (2013.01); *C12N 5/0663* (2013.01); *C12N 5/0667* (2013.01); *C12N 5/0668* (2013.01); *C12N 15/1138* (2013.01); *C12N 15/86* (2013.01); *C12N 2506/1353* (2013.01); *C12N 2509/00* (2013.01)

(58) Field of Classification Search
CPC .... A61K 2300/00; A61K 35/50; A61K 35/16; A61K 35/19; A61K 2035/122; A61K 31/7088; A61K 31/7105; A61K 31/713; C12N 5/0605; C12N 2310/14; C12N 2310/531; C12N 15/1138; C12N 15/86; C12N 2310/141; C12N 5/0607; C12N 2509/00; C12N 5/0662; C12N 2500/02; C12N 2506/1353; C12N 5/0663; C12N 5/0667; C12N 5/0668; C12N 2501/38; C12N 2501/65; C12N 2502/11; C12N 2710/10343; C12N 2740/15043; C12N 2800/30; C12N 2830/008; C12N 5/0647; C12N 5/0683; C12N 9/22; C12N 2506/03; C12N 2830/85; C12N 5/0623; C12N 5/0658; C12N 5/0664; C12N 5/0673

See application file for complete search history.

(56) References Cited

U.S. PATENT DOCUMENTS

| | | | |
|---|---|---|---|
| 7,060,492 B2 | 6/2006 | Vacanti et al. | |
| 2004/0057942 A1 | 3/2004 | Vacanti et al. | |
| 2006/0216821 A1 | 9/2006 | Totey et al. | |
| 2009/0068742 A1 | 3/2009 | Yamanaka | |
| 2009/0155225 A1 | 6/2009 | Ratajczak et al. | |
| 2009/0175832 A1 | 7/2009 | Zhao et al. | |
| 2011/0070647 A1* | 3/2011 | Dezawa | C12N 5/0607 435/378 |

FOREIGN PATENT DOCUMENTS

| | | |
|---|---|---|
| WO | WO-2005/017117 A2 | 2/2005 |
| WO | WO-2007/047581 A2 | 4/2007 |
| WO | WO 2007/069666 A1 | 6/2007 |
| WO | WO-2008/080200 A1 | 7/2008 |

OTHER PUBLICATIONS

Huang et al. Isolation of Mesenchymal Stem Cells from Human Placental Decidua Basalis and Resistance to Hypoxia and Serum Deprivation. Stem Cell Review and Rep., 2009, vol. 5, pp. 247-255.*
Battula et al. Human placenta and bone marrow derived MSC cultured in serum-free, b-FGF-containing medium express cell surface frizzled-9 and SSEA-4 and give rise to multilineage differentiation. Differentiation, 2007, vol. 75, 279-291.*
Sung et al. Stemness Evaluation of Mesenchymal Stem Cells from Placentas According to Developmental Stage: Comparison to Those from Adult Bone Marrow. Journal of Korean Medical Science, 2010, vol. 25, pp. 1418-1426.*
Chen et al. Differentiation of rat marrow mesenchymal stem cells into pancreatic islet beta-cells. World J. Gastroenterology, 2004, vol. 10, pp. 3016-3020.*
Chen et al. Engraftment potential of human placenta-derived mesenchymal stem cells after in utero transplantation in rats. Human Reproduction, 2009, vol. 24, pp. 154-165.*
Schwartz et al. J. Multipotent adult progenitor cells from bone marrow differentiate into functional hepatocyte-like cells. Clinical Invest., 2002, vol. 109, pp. 1291-1302.*
Kerkis et al. Isolation and Characterization of a Population of Immature Dental Pulp Stem Cells Expressing OCT-4 and Other Embryonic Stem Cell MarkersCells Tissues Organs, 2006, vol. 184, pp. 105-116.*

(Continued)

*Primary Examiner* — Deborah Crouch
(74) *Attorney, Agent, or Firm* — Foley & Lardner LLP

(57) ABSTRACT

Objects of the present invention are to provide a method for directly obtaining pluripotent stem cells from body tissue and the thus obtained pluripotent stem cells. The present invention relates to SSEA-3 (+) pluripotent stem cells that can be isolated from body tissue.

3 Claims, 50 Drawing Sheets

(56) References Cited

OTHER PUBLICATIONS

Liu et al. Dental Pulp Stem Cells. Methods in Enzymology, 2006, vol. 419, pp. 99-113.*
Rezapour et al. Telomere length and telomerase expression in human dental pulp cells. British Society for Dental Research, Sep. 1-4, 2009, Abs. 0228.*
Brooke et al. Molecular Trafficking Mechanisms of Multipotent Mesenchymal Stem Cells Derived from Human Bone Marrow and Placenta. Stem Cells and Development, 2008, vol. 17, pp. 929-940.*
Iohara et al. Side Population Cells Isolated from Porcine Dental Pulp Tissue with Self-Renewal and Multipotency for Dentinogenesis, Chondrogenesis, Adipogenesis, and Neurogenesis. Stem Cells, 2006, vol. 24, pp. 2493-2503.*
Iohara et al. Novel Stem Cell Source for Vasculogenesis in Ischemia: Subfraction of Side Population Cells from Dental Pulp. Stem Cells, 2008, vol. 26, pp. 2408-2418.*
Ferro et al. Isolation and Characterization of Human Dental Pulp Derived Stem Cells by Using Media Containing Low Human Serum Percentage as Clinical Grade Substitutes for Bovine SerumPLOS, 2012, vol. 7, e48945.*
Nakashima et al. Human dental pulp stem cells with highly angiogenic and neurogenic potential for possible use in pulp regeneration. Cytokine & Growth Factors, 2009, vol. 20, pp. 435-440.*
Chan et al. Antigen-presenting property of mesenchymal stem cells occurs during a narrow window at low levels of interferon-gamma. Blood, 2006, vol. 107, pp. 4817-4824.*
Gang et al. SSEA-4 identifies mesenchymal stem cells from bone marrow. Blood, 2007, vol. 109, pp. 1743-1751.*
Chris H. Jo et al., "Fetal mesenchymal stem cells derived from human umbilical cord sustain primitive characteristics during extensive expansion", Cell Tissue Res (2008) 334:423-433.
James A. Thomson et al., "Isolation of a primate embryonic stem cell line", Proc. Natl. Acad. Sci. USA, vol. 92, pp. 7844-7848, Aug. 1995.
Yasumasa Kuroda et al., "Unique multipotent cells in adult human mesenchymal cell populations", PNAS, May 11, 2010, vol. 107, No. 19, pp. 8639-8643.
Yong-Can Huang et al., "Isolation of Mesenchymal Stem Cells from Human Placental Decidua Basalis and Resistance to Hypoxia and Serum Deprivation", Stem Cell Rev. And Rep. (2009) 5:247-255.
Young-sup Yoon et al., "Clonally expanded novel multipotent stem cells from human bone marrow regenerate myocardium after myocardial infarction", The Journal of Clinical Investigation vol. 115, No. 2, Feb. 2005, pp. 325-338.
Eun J. Gang et al., "SSEA-4 identified mesenchymal stem cells from bone marrow", Blood, Feb. 15, 2007, vol. 109, No. 4, pp. 1743-1751.
Sebastien Start et al., "Ear mesenchymal stem cells: an efficient adult multipotent cell population fit for rapid and scalable expansion", Journal of Biotechnology 139 (2009) 291 299.
Joshua R. Mauney et al., "Matrix-mediated retention of in vitro osteogenic differentiation potential and in vivo bone-forming capacity by human adult bone marrow-derived mesenchymal stem cells during ex vivo expansion", Journal of Biomedical Material Research Part A DOI 10.1002, 2006, pp. 464-475.
Christine Moriscot et al., "Human Bone Marrow Mesenchymal Stem Cells Can Express Insulin and Key Transcription Factors of the Endocrine Pancreas Developmental Pathway upon Genetic and/or Microenvironmental Manipulation In Vitro", Stem Cells 2005; 23:594-604.
EP Patent Application No. 10799956.7, Communication dated Jan. 11, 2013.
CA Application No. 2,768,238, Office Action issued May 21, 2013.
CA Application No. 201080041908.7, Office Action issued May 22, 2013.
Draper J., et al., "Surface antigens of human embryonic stem cells: changes upon differentiation in culture", J. Anat. (2002) 200, pp. 249-258.
Henderson, J.K. et al., "Preimplantation Human Embryos and Embryonic Stem Cells Show Comparable Expression of Stage-Specific Enbryonic Antgens", Stem Cells 2002;20:329-337.
Moon, J.H., et al., Successful vitrification of human amnion-derived mesenchymal stem cells, Human Reproduction, 2008, vol. 23, No. 8 pp. 1760-1770.
Xiang-ming, Liu et al., "Culture and exogenous gene expression of adipose tissue-derived multipotent stem cells", Chinese Journal of Experimental Surgery, Feb. 2003, vol. 20, No. 2, pp. 162-163.
McGuckin, C.P. et al., "Production of Stem Cells With Embryonic Characteristics From Human Umbilical Cord Blood", Cell Proliferation, (2005) vol. 38, No. 4, pp. 245-255.
Zhang, Y.H. et al. "Isolation and Culture of Bone Marrow Mesenchymal Stem Cells From Human Fetus and Their Biological Properties", Chinese Journal of Agricultural Biotechnology (2008), 5(3), 237-244.
Australian Application No. 2010271722, Office Action issued Sep. 13, 2013.
Shinya Yamanaka, "Elite and stochastic models for induced pluripotent stem cell generation", Nature, vol. 460, No. 7251, Jul. 2, 2009 (Jul. 2, 2009), pp. 49-52, XP055083198.
Kubis et al., "Adult fast myosin pattern and $Ca^{2+}$ -induced slow myosin pattern in primary skeletal muscle culture," Proc. Natl. Aced, Sci, USA, Apr. 1997, 94:4205-4210.
Office Action dated Sep. 3, 2014 in U.S. Appl. No. 13/435,703.
i McKenna et al., "Isolation and Characterization of Umbilical Cord Blood-Derived Multipotent Stem Cells Arising from Adherent CD45+/CD34+ Cell Subset," Blood, 2005, 106(11):310A, Abstract 1064.

* cited by examiner

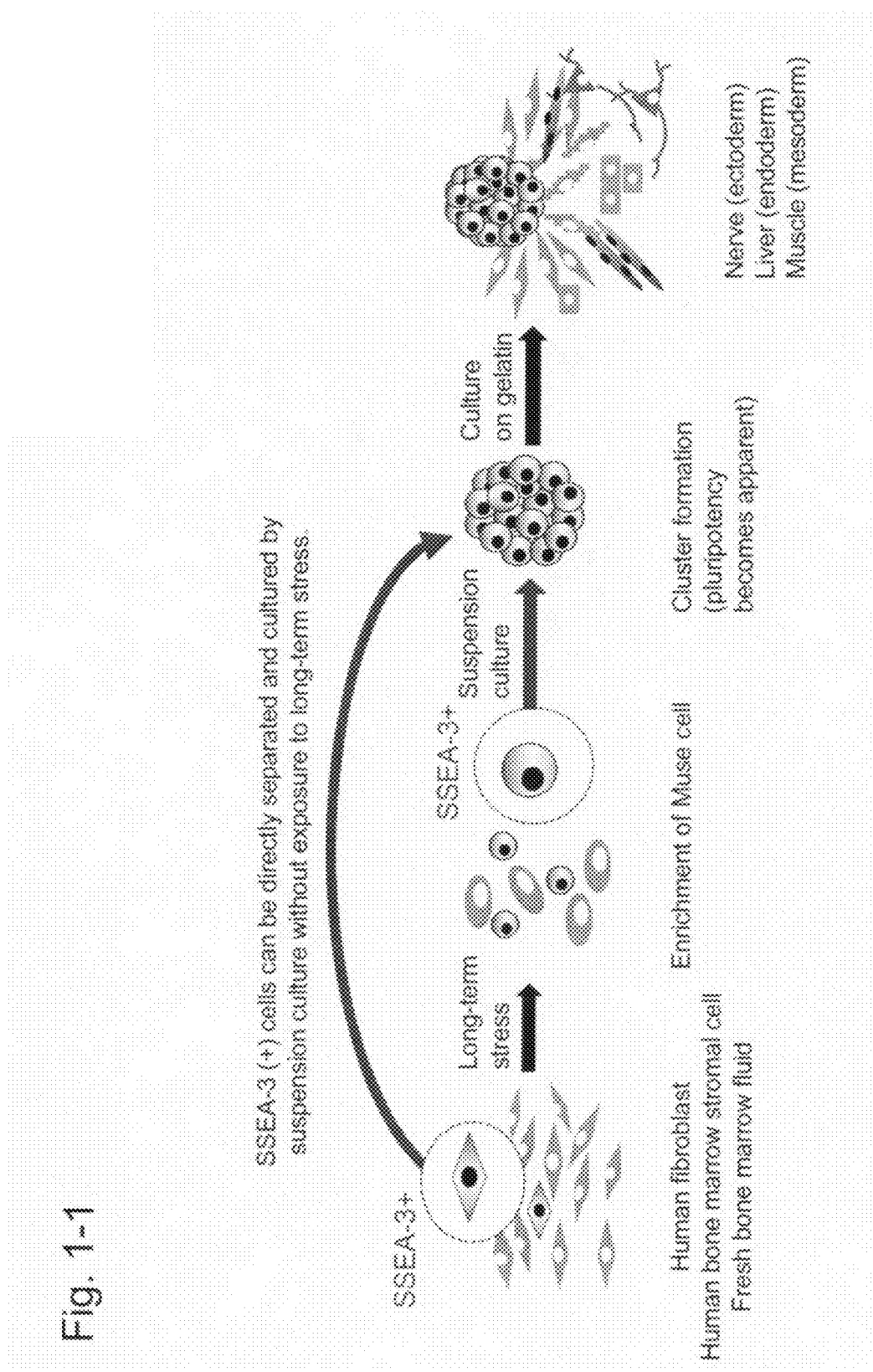

Fig. 2

| Gene Symbol | Total | D24 EB body/D24 Native | NHDF EB body/NHDF Native | Gene Title |
|---|---|---|---|---|
| THBD | 1267.42467 | 42.96487494 | 1224.459795 | thrombomodulin |
| IL1RN | 960.4457022 | 12.0038603 | 948.4418419 | interleukin 1 receptor antagonist |
| FOS | 954.4076469 | 88.7202031 | 865.6874438 | v-fos FBJ murine osteosarcoma viral oncogene homolog |
| SLC16A6 | 849.437506 | 715.7799818 | 133.6575242 | solute carrier family 16, member 6 (monocarboxylic acid transporter 7) |
| TYRP1 | 768.3374259 | 11.67216252 | 756.6652634 | tyrosinase-related protein 1 |
| CACNA1A | 685.5302732 | 3.084442121 | 682.445831 | Calcium channel, voltage-dependent, P/Q type, alpha 1A subunit |
| C16orf81 | 531.0858738 | 528.3969782 | 2.688895627 | chromosome 16 open reading frame 81 |
| CHI3L1 | 489.924397 | 373.8511267 | 116.0732704 | chitinase 3-like 1 (cartilage glycoprotein-39) |
| PRSS35 | 441.7622409 | 371.6403738 | 70.12186703 | protease, serine, 35 |
| KYNU | 420.8532931 | 182.1885786 | 238.6647145 | kynureninase (L-kynurenine hydrolase) |
| SLC16A6 | 407.4159044 | 315.8163678 | 91.59953662 | solute carrier family 16, member 6 (monocarboxylic acid transporter 7) |
| APOE | 357.4991884 | 105.5807107 | 251.9184778 | apolipoprotein E |
| THBD | 347.7592226 | 34.12473279 | 313.6344898 | thrombomodulin |
| SYTL5 | 320.0330513 | 15.80876986 | 304.2242814 | synaptotagmin-like 5 |
| CHI3L1 | 299.4142542 | 260.1989748 | 39.21527948 | chitinase 3-like 1 (cartilage glycoprotein-39) |
| ABCA13 | 290.3969665 | 271.9782856 | 18.41868089 | ATP-binding cassette, sub-family A (ABC1), member 13 |
| ANGPTL4 | 284.3113469 | 11.53113972 | 272.7802072 | angiopoietin-like 4 |
| PTGS2 | 273.0706903 | 201.4865123 | 71.58417805 | prostaglandin-endoperoxide synthase 2 (prostaglandin G/H synthase and cyclooxygenase) |
| STC1 | 255.0878156 | 29.28287475 | 225.8049409 | stanniocalcin 1 |
| CCDC102B | 253.1960755 | 37.22467468 | 215.9714008 | coiled-coil domain containing 102B |

Fig. 3

| Gene Symbol | Total | D24 EB/hES | EB/hES | NHDF EB/hES | Gene Title |
|---|---|---|---|---|---|
| MMP1 | 36528.90821 | 6836.563387 | | 29692.34482 | matrix metallopeptidase 1 (interstitial collagenase) |
| EREG | 19813.4402 | 18961.45781 | | 851.9823837 | epiregulin |
| CHI3L1 | 9641.34444 | 8842.305483 | | 799.038957 | chitinase 3-like 1 (cartilage glycoprotein-39) |
| — | 7940.341316 | 7298.64809 | | 641.6932268 | Transcribed locus |
| CHI3L1 | 5714.359227 | 5385.877946 | | 328.4812811 | chitinase 3-like 1 (cartilage glycoprotein-39) |
| SRGN | 4655.28423 | 4636.821662 | | 18.46256778 | serglycin |
| — | 4397.855874 | 3959.205654 | | 438.6502206 | MRNA full length insert cDNA clone EUROIMAGE 1913076 |
| RIN2 | 3611.379317 | 859.9132609 | | 2751.466056 | Ras and Rab interactor 2 |
| LUM | 3396.245648 | 1797.976375 | | 1598.269272 | lumican |
| CLCA2 | 3331.259662 | 747.5657674 | | 2583.693895 | CLCA family member 2, chloride channel regulator |
| IL8 | 3143.389365 | 2638.045747 | | 505.3436182 | interleukin 8 |
| LOC401097 | 3012.485859 | 1860.366679 | | 1152.119181 | Similar to LOC166075 |
| DPT | 2807.405266 | 56.39203934 | | 2751.013226 | dermatopontin |
| ELTD1 | 2658.65006 | 1751.976082 | | 906.6739784 | EGF, latrophilin and seven transmembrane domain containing 1 |
| IGFBP1 | 2423.035758 | 2405.299722 | | 17.73603586 | insulin-like growth factor binding protein 1 |
| SLC16A4 | 2305.561138 | 1826.823338 | | 478.7378001 | solute carrier family 16, member 4 (monocarboxylic acid transporter 5) |
| SRGN | 2293.730946 | 2279.537455 | | 14.19349126 | serglycin |
| GREM2 | 2053.928699 | 159.813291 | | 1894.115408 | gremlin 2, cysteine knot superfamily, homolog (Xenopus laevis) |
| IGFBP5 | 1960.755393 | 1915.425977 | | 45.3294163 | insulin-like growth factor binding protein 5 |
| SORDL | 1918.477233 | 1217.387684 | | 701.0895492 | sulfide quinone reductase-like (yeast) |

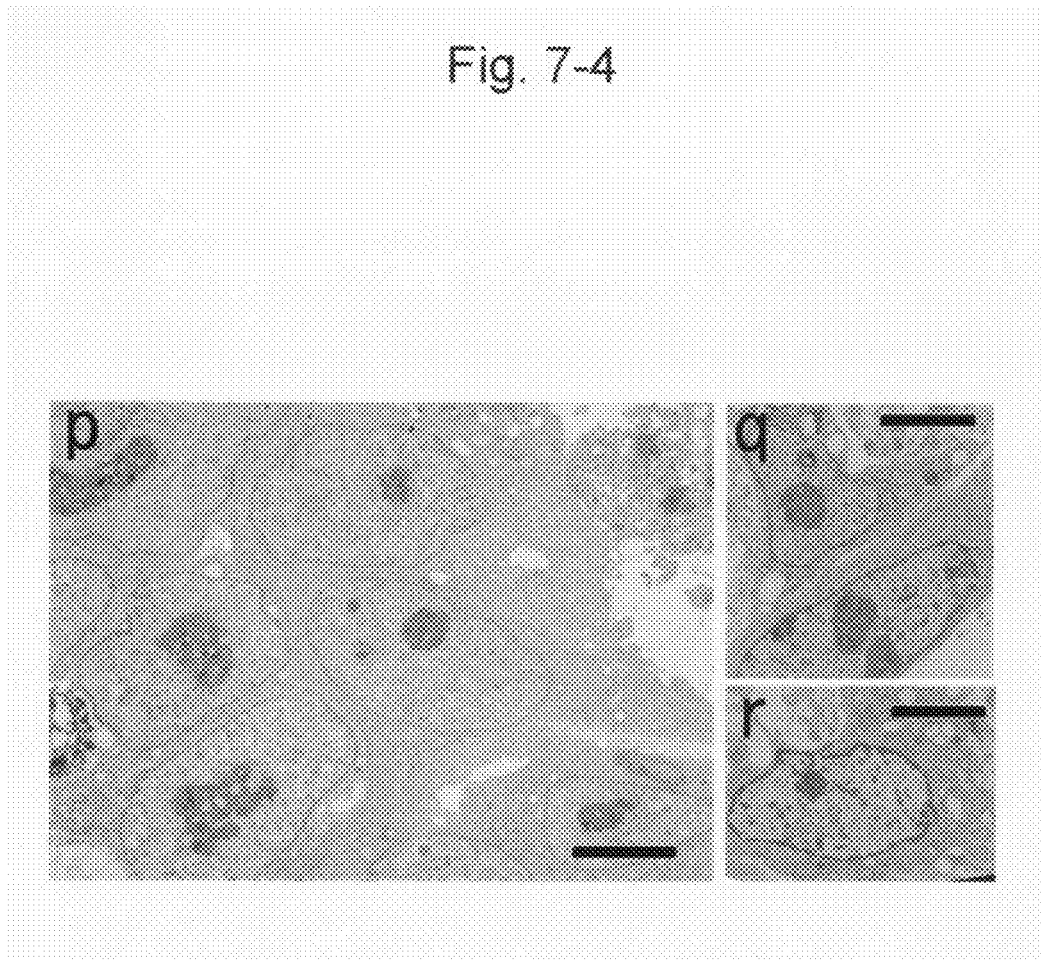

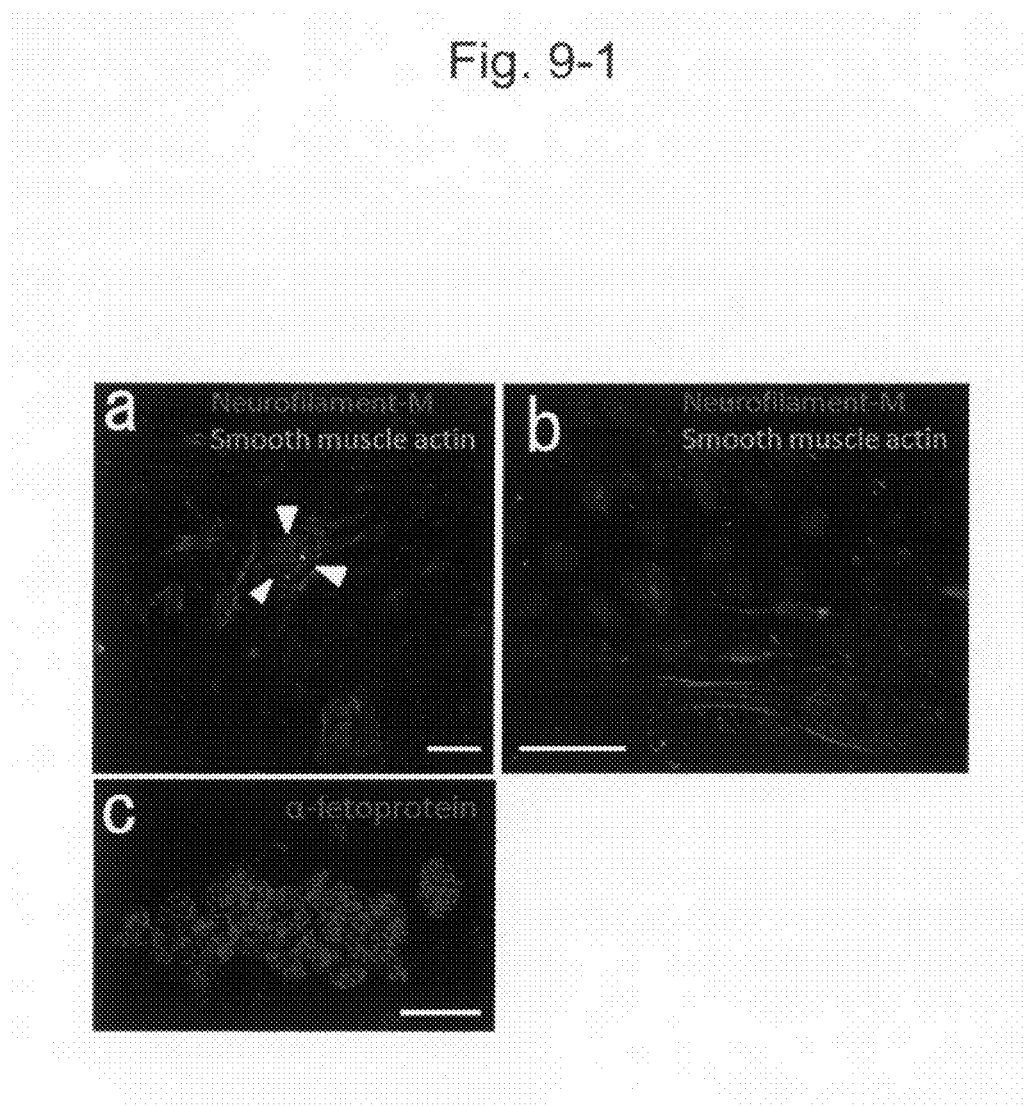

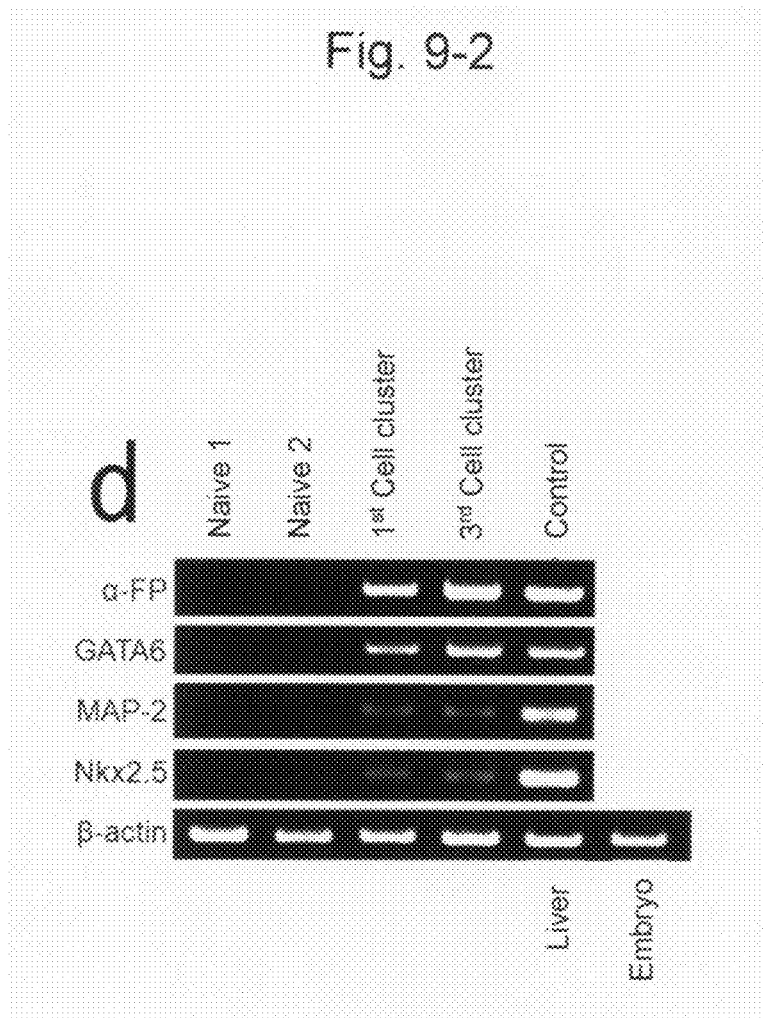

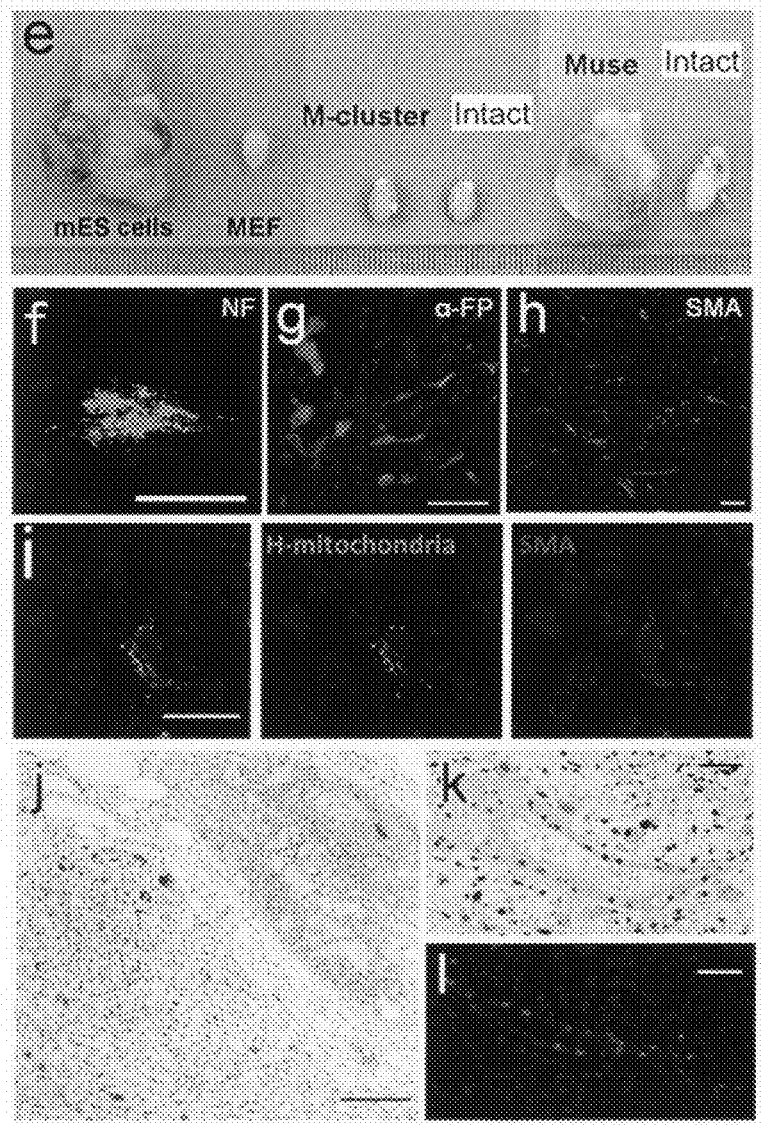

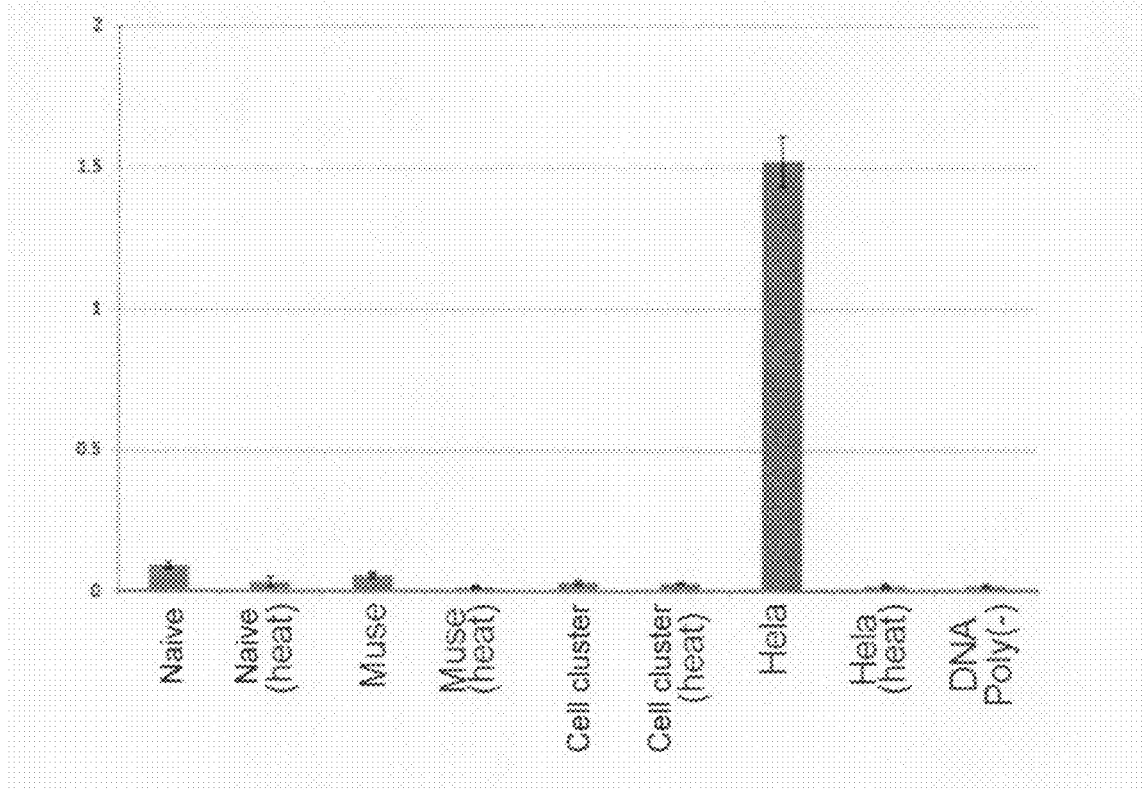

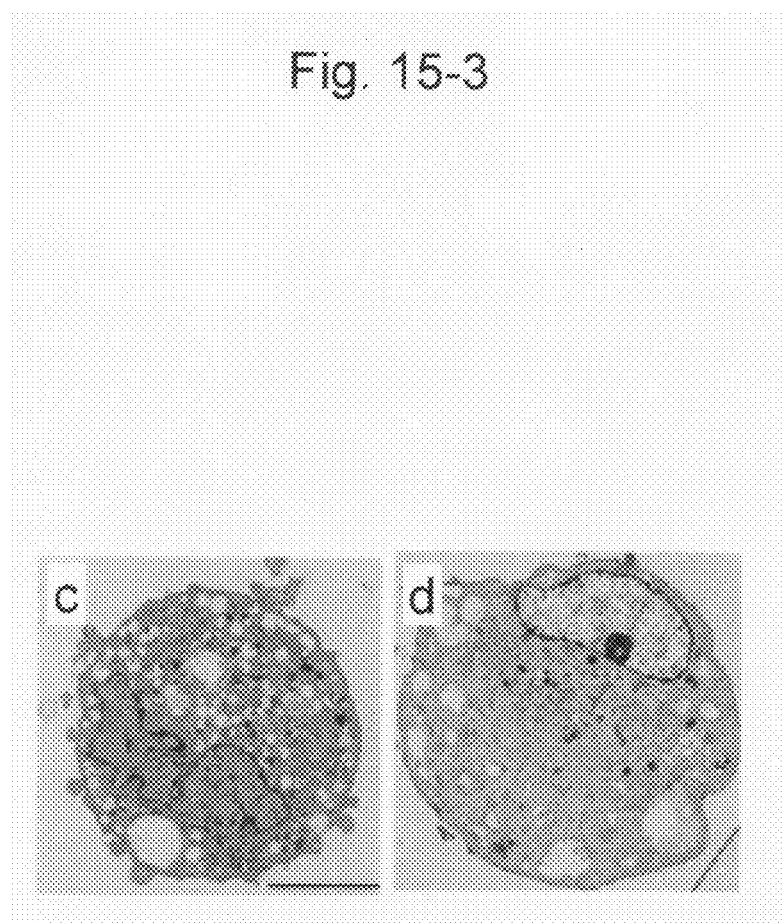

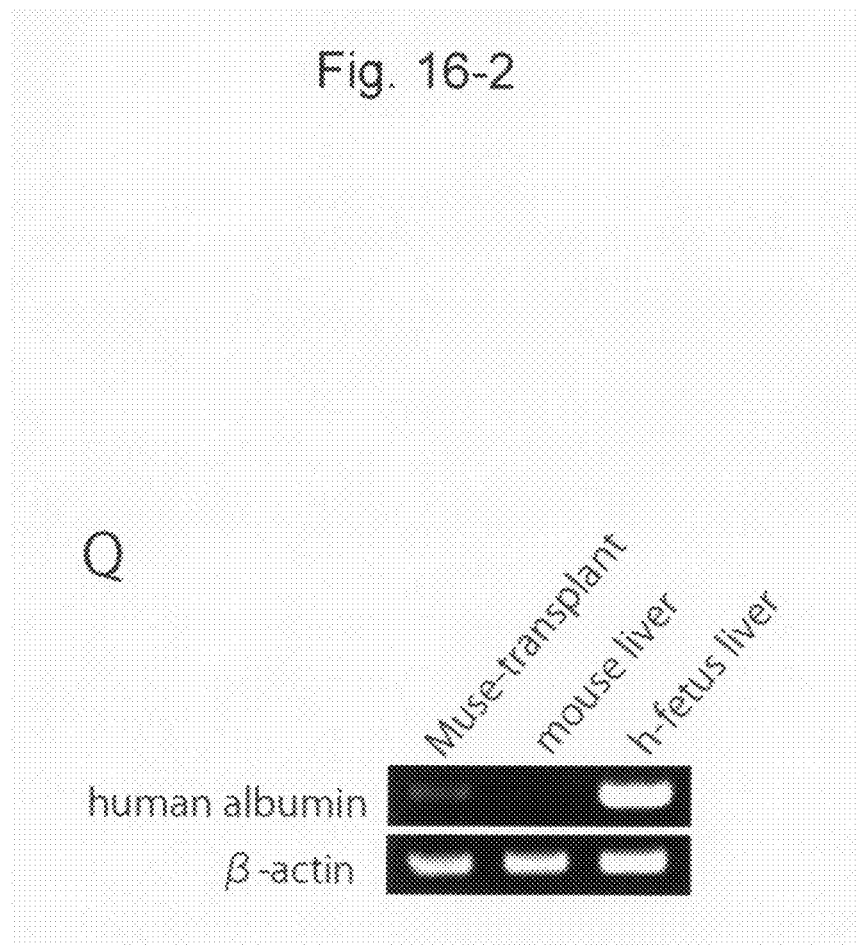

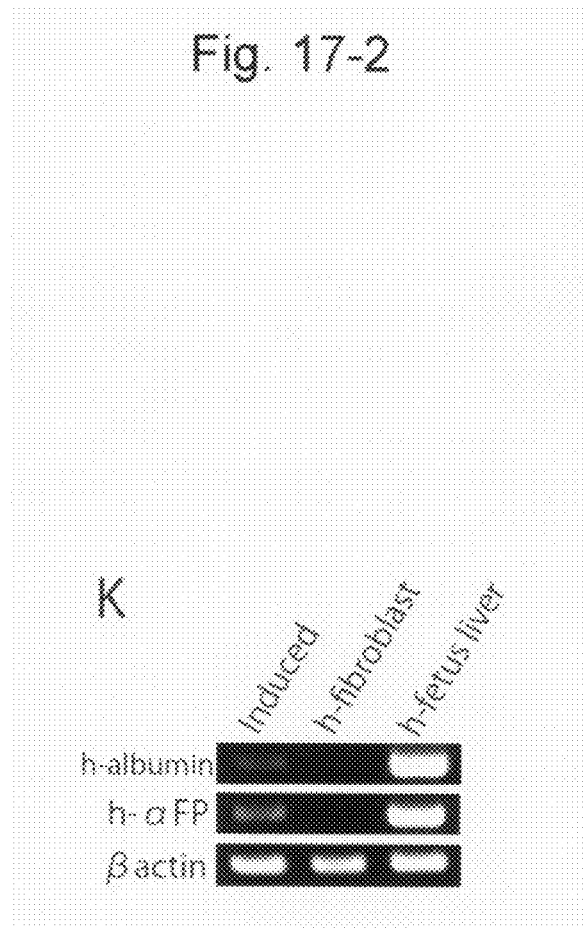

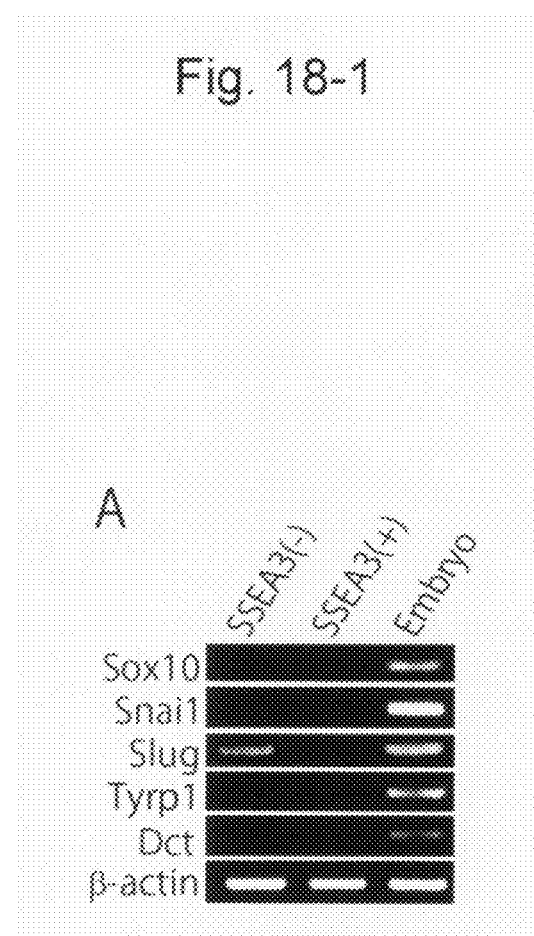

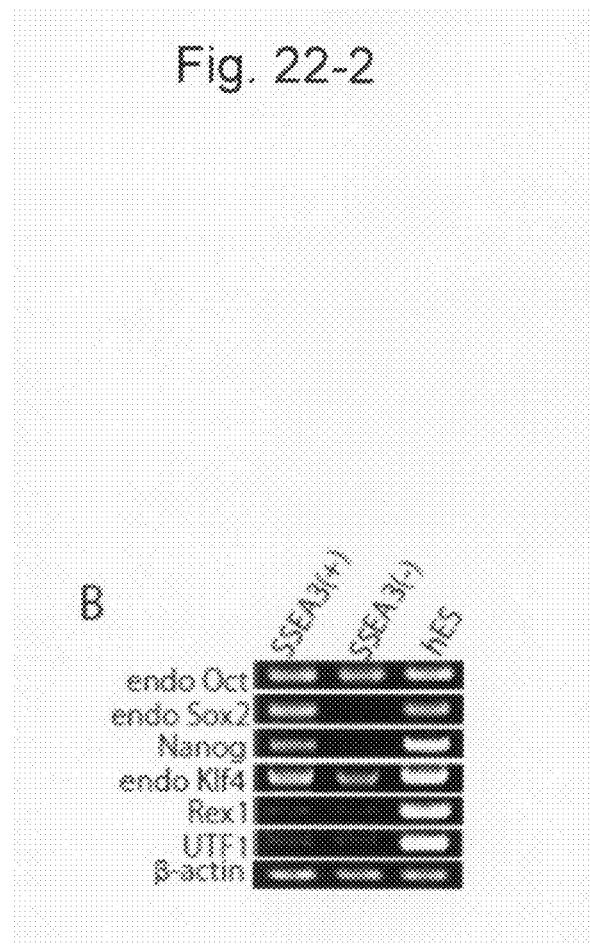

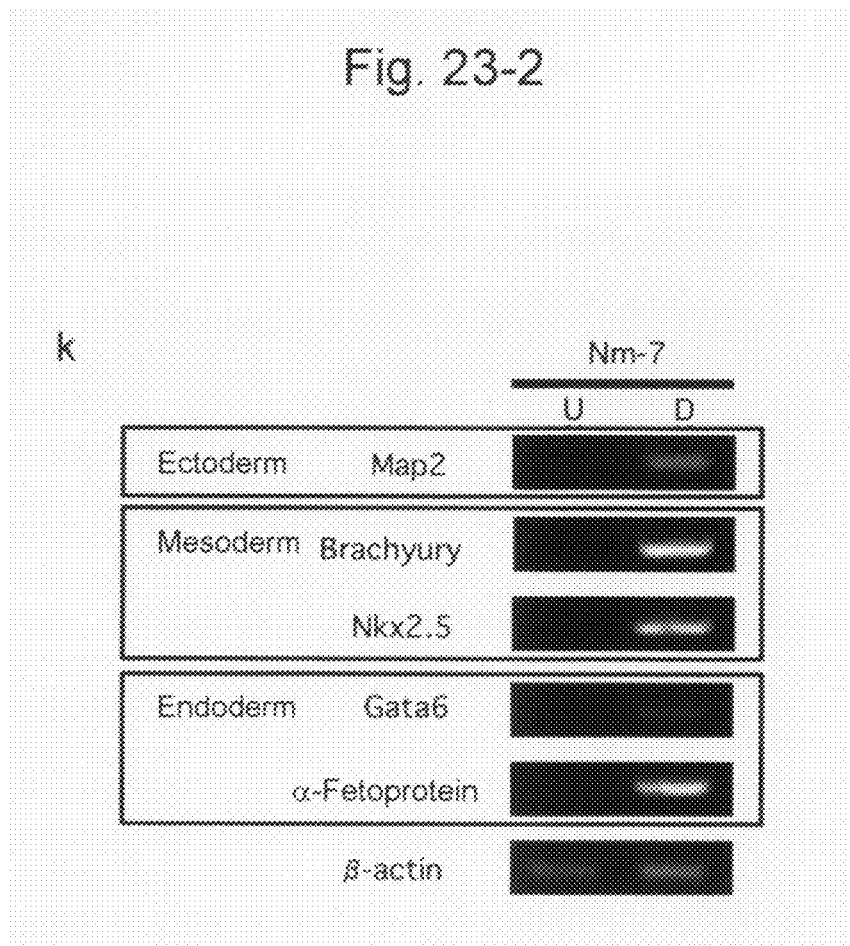

| Symbol | Description | Naïve Cluster | Naïve iPS | iPS Cluster |
|---|---|---|---|---|
| ABCA13 | ATP-binding cassette, sub-family A (ABC1), member 13 | | | 4.1E-01 |
| ALPL | Alkaline phosphatase, liver/bone/kidney | | | 2.9E-03* |
| ATRX | Alpha thalassemia/mental retardation syndrome X-linked (RAD54 homolog, S. cerevisiae) | | | 9.9E-01 |
| BMP4 | Bone morphogenetic protein 4 | | | 1.4E-01* |
| BMPR1A | Bone morphogenetic protein receptor, type IA | | | 6.6E-01 |
| CBX7 | Chromobox homolog 7 | | ▨ | 5.5E+00** |
| CTR9 | Ctr9, Paf1/RNA polymerase II complex component, homolog (S. cerevisiae) | | | 6.2E-01 |
| DAZL | Deleted in azoospermia-like | | | 5.8E-02^ |
| DDX4 | DEAD (Asp-Glu-Ala-Asp) box polypeptide 4 | | | 8.0E-01 |
| DNMT1 | DNA (cytosine-5-)-methyltransferase 1 | | | 2.1E-01* |
| DNMT3B | DNA (cytosine-5-)-methyltransferase 3 beta | | | 6.2E-04* |
| DPPA2 | Developmental pluripotency associated 2 | | | 1.6E-03* |
| DPPA3 | Developmental pluripotency associated 3 | | | 1.1E-02* |
| DPPA4 | Developmental pluripotency associated 4 | | | 1.1E-04* |
| EPC1 | Enhancer of polycomb homolog 1 (Drosophila) | | | 8.2E-01 |
| ERAS | ES cell expressed Ras | | | 1.1E-01* |
| F11R | F11 receptor | | | 2.0E-03* |
| FGFR1 | Fibroblast growth factor receptor 1 (fms-related tyrosine kinase 2, Pfeiffer syndrome) | | | 5.8E-03 |
| FOXD3 | Forkhead box D3 | | | 4.2E-04^ |
| GDF3 | Growth differentiation factor 3 | | | 8.0E+00* |
| GRB7 | Growth factor receptor-bound protein 7 | | | 1.8E-03* |
| HAND1 | Heart and neural crest derivatives expressed 1 | | | 1.9E-02* |
| HES1 | Hairy and enhancer of split 1, (Drosophila) | | | 1.4E+00 |
| HEXIM1 | Hexamethylene bis-acetamide inducible 1 | | | 2.8E+00 |
| HOXB1 | Homeobox B1 | | | 4.7E-02* |
| ID1 | Inhibitor of DNA binding 1, dominant negative helix-loop-helix protein | | | 3.3E+00** |
| ID3 | Inhibitor of DNA binding 3, dominant negative helix-loop-helix protein | | | 3.0E+00** |
| IFITM1 | Interferon induced transmembrane protein 1 (9-27) | | | 1.7E-01* |
| KCNK3 | Potassium channel, subfamily K, member 3 | | | 3.4E+00** |
| KITLG | KIT ligand | | ▨ | 1.2E-01** |
| KLF4 | Kruppel-like factor 4 (gut) | | | 1.0E+00 |
| LIN28 | Lin-28 homolog (C. elegans) | | | 3.5E-04* |
| MSX2 | Msh homeobox 2 | | | 3.8E-01 |
| MYC | V-myc myelocytomatosis viral oncogene homolog (avian) | | | 7.6E-01 |
| NANOG | Nanog homeobox | | | 4.0E-04* |
| NAT1 | N-acetyltransferase 1 (arylamine N-acetyltransferase) | | | 9.4E-01 |
| NKX1-2 | NK1 homeobox 2 | | | 2.3E-03* |
| NR6B1 | Nuclear receptor subfamily 6, group B, member 1 | | | 2.4E-01** |
| OCT3/4 | POU class 5 homeobox 1 | | | 1.8E-02* |
| OTX2 | Orthodenticle homeobox 2 | | | 8.0E+00* |
| PAN3 | PAN3 poly(A) specific ribonuclease subunit homolog (S. cerevisiae) | | | 4.5E-01 |
| PODXL | Podocalyxin-like | | | 3.8E-02* |
| PRDM1 | PR domain containing 1, with ZNF domain | | | 1.0E-01** |
| RAG1AP1 | Recombination activating gene 1 activating protein 1 | | | 8.6E-01 |
| SALL4 | Sal-like 4 (Drosophila) | | | 6.4E-04* |
| SIX4 | SIX homeobox 4 | | | 9.9E-01 |
| SOX2 | SRY (sex determining region Y)-box 2 | | | 7.4E-04* |
| SPAG9 | Sperm associated antigen 9 | | | 1.3E+00 |
| SPRY1 | Sprouty homolog 1, antagonist of FGF signaling (Drosophila) | | | 5.1E-01 |
| SPRY2 | Sprouty homolog 2 (Drosophila) | | | 1.9E+00 |
| SSBP2 | Single-stranded DNA binding protein 2 | | | 1.7E+00 |
| STAT3 | Signal transducer and activator of transcription 3 (acute-phase response factor) | | | 1.6E+00 |
| TDGF1 | Teratocarcinoma-derived growth factor 1 | | | 3.8E-05* |
| TFE3 | Transcription factor binding to IGHM enhancer 3 | | | 1.1E+00 |
| TRDMT1 | tRNA aspartic acid methyltransferase 1 | | | 7.3E-01 |
| UTF1 | Undifferentiated embryonic cell transcription factor 1 | | | 8.0E+00* |
| VIM | Vimentin | | ▨ | 1.4E-02** |

Fig. 27

| Animal | Reprogramming factor [b] | Cell type | Time (week) | Efficiency |
|---|---|---|---|---|
| Mouse | Viral-integrating vectors | | | |
| | O, K, S, M | MEFs | 2-3 | 0.01-0.50% |
| | O, K, S, M | Hepatocyte | 2-3 | 1-3% |
| | O, K, S, M | Gastric epithelial cell | 2-3 | 1-3% |
| | O, K, S, M | B cell | 2-3 | 0.01-0.10% |
| | O, K, S, M | B cell | 3-4 | 0.1-0.2% |
| | O, K, S, M | Neural stem cell | 1-2 | 3-5% |
| | O, K, S | MEFs | 3-4 | 0.001-0.010% |
| | O, K, S | Hepatocyte | 2-3 | 0.5-1.0% |
| | O, K, M | Neural stem cell | 1-2 | 0.1-1.0% |
| | O, K, | Neural stem cell | 2-3 | 0.1-1.0% |
| | O, M, S | Neural stem cell | 3-4 | 0.1-1.0% |
| | O, K | Neural stem cell | 2-3 | 0.1-0.2% |
| | O, M | Neural stem cell | 3-4 | 0.1-0.2% |
| | Non-integrating viral vectors [c] | | | |
| | O, K, S, M | Hepatocyte | 4-5 | 0.0001 to 0.0010% |
| | Plasmid-based vedtros [c] | | | |
| | O, K, S, M | MEFs | 3-4 | 0.0001 to 0.0010% |
| Human | Viral-integrating vectors | | | |
| | O, K, S, M | Dermal fibroblast | 4-5 | 0.001-0.002% |
| | O, K, L, N | Dermal fibroblast | 2-3 | N.D. |
| | O, K, S, M | Bone marrow stromal cell | 2-3 | N.D. |
| | O, K, N | Dermal fibroblast | 2-3 | N.D. |
| | O, K, L | Dermal fibroblast | 2-3 | N.D. |
| | O, S, K [d] | Dermal fibroblast | 4 | 0.1-1.0% |
| | O, S [d] | Dermal fibroblast | 4 | 0.001-0.010% |
| | O, S, L, N [e] | Dermal fibroblast | | 0.002% |
| | O, K, S, M, T,LT | Dermal fibroblast | | 0.0417% |
| | O, K, S, M, p, U | Dermal fibroblast | | N.D. |

MEFs, Mouse embryonic fibroblast  ; N.D., not determined.

[b] O, Oct4; S, Sox2; M, c-Myc; K, Klf4; N, Nanog; L, Lin28; T, hTERT; LT, Large T antigen; p, p53RNAi; U, Utf1
[c] Integration-free clones.
[d] Valpronic acid (VPA) used in association
[e] CHIR99021, PD0325901, A-83-01

Fig. 28-1

| Gene Symbol | Total | D24 EB/hES | NHDF EB/hES | Gene Title |
|---|---|---|---|---|
| MMP1 | | 6836.563387 | 29692.34482 | matrix metallopeptidase 1 (interstitial collagenase) |
| EREG | | 18961.45781 | 851.9823837 | epiregulin |
| CHI3L1 | | 8842.305483 | 799.038957 | chitinase 3-like 1 (cartilage glycoprotein-39) |
| | | 7298.64809 | 641.6932268 | Transcribed locus |
| CHI3L1 | | 5385.877946 | 328.4812811 | chitinase 3-like 1 (cartilage glycoprotein-39) |
| SRGN | | 4636.821662 | 18.46256778 | serglycin |
| | | 3959.205654 | 438.6502206 | mRNA full length insert cDNA clone EUROIMAGE 1913076 |
| RIN2 | | 859.9132609 | 2751.466056 | Ras and Rab interactor 2 |
| LUM | | 1797.976375 | 1598.269272 | lumican |
| CLCA2 | | 747.5657674 | 2583.693895 | CLCA family member 2, chloride channel regulator |
| IL8 | | 2638.045747 | 505.3436182 | interleukin 8 |
| LOC401097 | | 1860.366679 | 1152.119181 | Similar to LOC166075 |
| DPT | | 56.39203934 | 2751.013226 | dermatopontin |
| ELTD1 | | 1751.976082 | 906.6739784 | EGF, latrophilin and seven transmembrane domain containing 1 |
| IGFBP1 | | 2405.299722 | 17.73603586 | insulin-like growth factor binding protein 1 |
| SLC16A4 | | 1826.823338 | 478.7378001 | solute carrier family 16, member 4 (monocarboxylic acid transporter 5) |
| SRGN | | 2279.537455 | 14.19349126 | serglycin |
| GREM2 | | 159.813291 | 1894.115408 | gremlin 2, cysteine knot superfamily, homolog (Xenopus laevis) |
| IGFBP5 | | 1915.425977 | 45.3294163 | insulin-like growth factor binding protein 5 |
| SORDL | | 1217.387684 | 701.0895492 | sulfide_quinone_reductase-like (yeast) |
| — | 1814.837028 | 655.8277916 | 1159.009236 | Transcribed locus |
| AREG /// LOC727738 | 1806.585841 | 1672.163804 | 134.4220365 | amphiregulin (schwannoma-derived growth factor) /// similar to Amphiregulin precursor (AR) (Colorectum cell-derived growth factor) (CRDGF) |
| EMP1 | 1801.38162 | 557.8761568 | 1243.505463 | epithelial membrane protein 1 |
| COL15A1 | 1748.186405 | 119.9214244 | 1628.264981 | collagen, type XV, alpha 1 |
| FBN1 | 1697.498686 | 953.834625 | 743.6640606 | fibrillin 1 |
| IL1RN | 1663.004514 | 120.1560006 | 1542.848513 | interleukin 1 receptor antagonist |
| DAB2 | 1494.45958 | 464.4242886 | 1030.035291 | disabled homolog 2, mitogen-responsive phosphoprotein (Drosophila) |
| GREM2 | 1444.798877 | 147.9138456 | 1296.885032 | gremlin 2, cysteine knot superfamily, homolog (Xenopus laevis) |
| PDGFC | 1416.788978 | 865.6973811 | 551.0915972 | platelet derived growth factor C |
| PAPPA | 1357.515527 | 803.4393837 | 554.0761438 | pregnancy-associated plasma protein A, pappalysin 1 |
| C10orf116 | 1307.677751 | 258.5741117 | 1049.103639 | chromosome 10 open reading frame 116 |
| IL1R1 | 1259.786075 | 623.1158457 | 636.6702292 | interleukin 1 receptor, type I |
| — | 1200.501384 | 523.8789352 | 676.6224486 | Transcribed locus |
| EBF3 | 1185.690975 | 796.9144449 | 388.77653 | early B-cell factor 3 |
| PROS1 | 1149.848318 | 449.3148088 | 700.5335091 | protein S (alpha) |
| FAP | 1125.578819 | 484.0830816 | 641.4957369 | fibroblast activation protein, alpha |
| C8orf4 | 1116.284673 | 13.09736284 | 1103.18731 | chromosome 8 open reading frame 4 |
| FOS | 1107.696912 | 165.1111658 | 942.5857465 | v-fos FBJ murine osteosarcoma viral oncogene homolog |
| COMP | 1090.255019 | 16.76702438 | 1073.487994 | cartilage oligomeric matrix protein |
| GLRB | 1052.249166 | 768.4562142 | 283.7929515 | glycine receptor, beta |
| SLC14A1 | 1052.151636 | 958.7509434 | 93.40069261 | solute carrier family 14 (urea transporter), member 1 (Kidd blood group) |
| ABCC3 | 1037.863003 | 663.4940584 | 374.3689445 | ATP-binding cassette, sub-family C (CFTR/MRP), member 3 |
| CLEC2B | 1019.89733 | 18.2056167 | 1001.691714 | C-type lectin domain family 2, member B |
| COL3A1 | 1018.504577 | 517.5218326 | 500.9827444 | collagen, type III, alpha 1 (Ehlers-Danlos syndrome type IV, autosomal dominant) |
| MAP7 | 1016.798284 | 145.1429371 | 871.6553471 | microtubule-associated protein 7 |
| OSR2 | 966.5431651 | 38.9019319 | 927.6412332 | odd-skipped related 2 (Drosophila) |
| HOXB2 | 950.0476607 | 518.760048 | 431.2876127 | homeobox B2 |
| ITGBL1 | 948.2039106 | 494.167077 | 454.0368336 | integrin, beta-like 1 (with EGF-like repeat domains) |
| ABCA8 | 943.3622113 | 894.3291151 | 49.03309627 | ATP-binding cassette, sub-family A (ABC1), member 8 |
| NRP1 | 894.0228288 | 518.9430639 | 375.0797648 | neuropilin 1 |

Fig. 28-2

| Gene | Value 1 | Value 2 | Value 3 | Description |
|---|---|---|---|---|
| NOL3 | 15.41799591 | 7.766489677 | 7.651506237 | nucleolar protein 3 (apoptosis repressor with CARD domain) |
| — | 15.41596274 | 11.95827993 | 3.457682805 | CDNA clone IMAGE:4822326 |
| SVEP1 | 15.41468788 | 5.535677064 | 9.879010816 | sushi, von Willebrand factor type A, EGF and pentraxin domain containing 1 |
| CAMK2D | 15.41262564 | 8.17551343 | 7.23711221 | calcium/calmodulin-dependent protein kinase (CaM kinase) II delta |
| hCG_1815491 | 15.41192586 | 10.46719301 | 4.944732847 | hCG1815491 |
| C18orf10 | 15.40701547 | 9.506970952 | 5.90004452 | chromosome 18 open reading frame 10 |
| — | 15.40096737 | 10.7727781 | 4.628189269 | — |
| ANXA2 | 15.39954343 | 6.204722252 | 9.194821182 | annexin A2 |
| BGN | 15.3988053 | 4.361357791 | 11.03744751 | biglycan |
| NPAS2 | 15.36079462 | 10.69063847 | 4.670156155 | neuronal PAS domain protein 2 |
| GPR39 | 15.35089265 | 12.85500307 | 2.495889575 | G protein-coupled receptor 39 |
| TBC1D20 | 15.35003815 | 6.745091841 | 8.604946313 | TBC1 domain family, member 20 |
| CDC14B | 15.33832482 | 6.806843594 | 8.531481228 | CDC14 cell division cycle 14 homolog B (S. cerevisiae) |
| NOTCH2NL | 15.3272291 | 11.83504048 | 3.492188618 | Notch homolog 2 (Drosophila) N-terminal like |
| LCP2 | 15.3251731 | 4.546855376 | 10.77831772 | Lymphocyte cytosolic protein 2 (SH2 domain containing leukocyte protein of 76kDa) |
| AQP1 | 15.32426142 | 2.821856353 | 12.50240507 | aquaporin 1 (Colton blood group) |
| — | 15.32367793 | 6.021056047 | 9.302621887 | CDNA FLJ41633 fis, clone FCBBF3003435 |
| SLC8A1 | 15.31594521 | 9.090876077 | 6.225069136 | solute carrier family 8 (sodium/calcium exchanger), member 1 |
| BMPR2 | 15.31387606 | 6.189677952 | 9.124198105 | bone morphogenetic protein receptor, type II (serine/threonine kinase) |
| — | 15.29567333 | 7.834223924 | 7.461449409 | Transcribed locus |
| TTC28 | 15.28559523 | 5.590303325 | 9.6952919 | tetratricopeptide repeat domain 28 |
| — | 15.28329827 | 8.748454619 | 6.534843649 | CDNA FLJ26764 fis, clone PRS02668 |
| C9orf3 | 15.27777853 | 8.911694325 | 6.366084206 | Chromosome 9 open reading frame 3 |
| — | 15.27597235 | 5.290822744 | 9.98514961 | — |
| — | 15.26155759 | 5.468095085 | 9.793462509 | Transcribed locus |
| ZNF221 | 15.25363462 | 6.258695067 | 8.994939557 | zinc finger protein 221 |
| LOC100130069 /// PLOD1 | 15.2427204 | 8.617209232 | 6.625511171 | procollagen-lysine 1, 2-oxoglutarate 5-dioxygenase 1 /// hypothetical protein LOC100130069 |
| LGALS3 | 15.23097353 | 7.89432313 | 7.336650397 | lectin, galactoside-binding, soluble, 3 |
| TMEM39A | 15.22760776 | 7.429853967 | 7.797753794 | Transmembrane protein 39A |
| HECA | 15.21973088 | 7.310799768 | 7.908931111 | headcase homolog (Drosophila) |
| EHD2 | 15.21817806 | 6.844545618 | 8.373632438 | EH-domain containing 2 |
| COL13A1 | 15.21773453 | 2.819123808 | 12.39861073 | collagen, type XIII, alpha 1 |
| — | 15.21711024 | 5.44080361 | 9.776366627 | CDNA clone IMAGE:4828503 |
| — | 15.20772937 | 10.54579274 | 4.66193663 | — |
| — | 15.19097239 | 6.187291277 | 9.003681115 | Transcribed locus |
| — | 15.18035142 | 6.732157641 | 8.448193782 | Transcribed locus |
| RAB40B | 15.17098134 | 5.006355059 | 10.16462628 | RAB40B, member RAS oncogene family |
| RHOJ | 15.1707093 | 12.84707507 | 2.323634225 | ras homolog gene family, member J |
| — | 15.16823555 | 10.37451911 | 4.793716442 | Transcribed locus |
| PECAM1 | 15.16685381 | 10.89929086 | 4.267562956 | platelet/endothelial cell adhesion molecule (CD31 antigen) |
| RUNX2 | 15.16677852 | 13.13542498 | 2.031353545 | runt-related transcription factor 2 |
| EGFR | 15.16406401 | 7.455536404 | 7.708527604 | epidermal growth factor receptor (erythroblastic leukemia viral (v-erb-b) oncogene homolog, avian) |
| — | 15.15700188 | 7.0370799 | 8.119921977 | — |
| COMT | 15.14255329 | 9.027278661 | 6.115274626 | catechol-O-methyltransferase |
| RALBP1 | 15.13725631 | 9.952643151 | 5.184613157 | ralA binding protein 1 |
| RSPH3 | 15.13130254 | 8.227915901 | 6.903386637 | radial spoke head 3 homolog (Chlamydomonas) |
| — | 15.1292579 | 6.122960267 | 9.00629763 | MRNA; cDNA DKFZp56400862 (from clone DKFZp56400862) |
| HOMER3 | 15.11743606 | 5.720074493 | 9.397361565 | homer homolog 3 (Drosophila) |
| TTC8 | 15.115157 | 6.058678355 | 9.056478645 | tetratricopeptide repeat domain 8 |
| TAS2R14 | 15.11245803 | 9.533766985 | 5.578691043 | taste receptor, type 2, member 14 |
| HOMER3 | 15.11159228 | 7.270534231 | 7.841058048 | homer homolog 3 (Drosophila) |
| TPCN1 | 15.09788412 | 7.691551981 | 7.406332139 | two pore segment channel 1 |
| THBD | 15.09190347 | 7.106698173 | 7.985205298 | thrombomodulin |
| CAPN8 /// LOC644151 | 15.09078702 | 8.956617146 | 6.134169873 | calpain 8 /// similar to calpain 8 |
| ALDH1L2 | 15.08198674 | 9.273925498 | 5.808061237 | Aldehyde dehydrogenase 1 family, member L2 |

SSEA-3 PLURIPOTENT STEM CELL ISOLATED FROM BODY TISSUE

BACKGROUND OF THE INVENTION

Field of the Invention

The present invention relates to body tissue-derived Pluripotent stem cells.

Background Art

Planarians and newts can regenerate their entire bodies even after their bodies have been cut. Such high regenerative capacity depends on the presence of pluripotent stem cells existing in the mesenchymal tissues. However, in the case of higher organisms such as humans, the tissue regenerative capacity is far lower than that of those animals. An inner cell cluster (or ICM: inner cell mass) in a mammalian blastocyst is recognized as a collection of pluripotent stem cells that is capable of differentiating into cells of ectodermal, mesodermal, and endodermal cell lineages. However, such pluripotency becomes limited as development proceeds, followed by cell differentiation for specialization resulting in each type of tissue.

In recent years, adult stem cells or tissue stem cells that can contribute to tissue regeneration have been attracting attention. However, it has remained unknown whether or not pluripotent stem cells are present in mature mammalian bodies, as in the case of planarians or newts.

Bone marrow stromal cell (MSC) fractions having the ability to differentiate into bone, cartilage, adipocytes, neuronal cells, skeletal muscles, and the like have been reported as cells obtained from an adult having differentiation potency (see Non-Patent Documents 1 and 2). However, bone marrow stromal cells (MSCs) are comprised of various kinds of cell populations. The differentiation potency of MSC population is varied, but the main body thereof is not clearly understood. Furthermore, it requires stimulation with a specific compound, gene transfer, or the like for differentiation into specific cells. Specifically, there is a need to construct a system for inducing differentiation.

Furthermore, iPS cells (induced pluripotent stem cells) (see Patent document 1, Patent document 2, Non-patent document 3, and the like) have been reported as adult-derived pluripotent stem cells. However, establishment of iPS cells requires an induction operation using a specific substance, such as introduction of a specific gene into a dermal fibroblast fraction (dermal fibroblast) that is a mesenchymal cell population or introduction of a specific compound into somatic cells.

Patent document 1 JP Patent No. 4183742
Patent document 2 JP Patent Publication (Kokai) No. 2008-307007 A
Non-patent document 1 M. DEZAWA et al., The Journal of Clinical Investigation, 113, 12, pp. 1701-1710, (2004)
Non-patent document 2 M. DEZAWA et al., SCIENCE, 2005 Jul. 8, 309, pp. 314-317, (2005)
Non-patent document 3 Okita K. et al. SCIENCE, 2008 Nov. 7, 322 (5903), pp. 949-953

SUMMARY OF THE INVENTION

An object of the present invention is to provide a method for directly obtaining pluripotent stem cells from body tissue and pluripotent stem cells obtained by the method.

The present inventors have discovered that in the research process concerning bone marrow stromal cell (MSC: bone marrow stromal cell) fractions, characteristic cell clusters are formed at extremely low frequency from untreated (naive) human MSC cells. The appearance of initial cell clusters closely resembles that of ES cells. However, the cell clusters do not undergo infinite growth, unlike ES cells. They stop growth when they reach a size within a certain period and then they form heterogeneous populations containing various cells such as hair cells and pigment cells. Also, immunocytochemistry was performed for such cell clusters, so that different cells positive for ectodermal, endodermal, and mesodermal markers, respectively, were detected in a cell cluster. The present inventors considered from the results the possible presence of cells equivalent to pluripotent/multipotent cells in untreated (naive) human MSC cell fractions that are generally maintained and cultured. The present inventors then further intensively studied the matter.

It is known that when a body is exposed to stress or injured, tissue stem cells in a dormant state are activated, contributing to tissue regeneration. The present inventors have provided stimulation stress to mesenchymal cells such as bone marrow stromal cell (MSC) fractions and dermal fibroblast fractions while culturing them according to various methods (e.g., serum free culture, culture using Hank's Balanced Salt Solution (HBSS), low oxygen culture, a total of 3 hours of intermittent short-time trypsin culture, and 8 or 16 hours of long-time trypsin incubation), collected surviving cells, and then performed suspension culture in methylcellulose (MC)-containing medium (called "MC culture"). As a result, formation of various sizes of embryoid body-like cell clusters (up to a maximum diameter of 150 µm) was confirmed. In particular, embryoid body-like cell cluster formation was confirmed at the highest frequency in human dermal fibroblast fractions and human MSC fractions subjected to long-term trypsin incubation.

The present inventors have examined the properties of cells in the thus obtained embryoid body-like cell clusters, and thus they have discovered that such cells have the properties of pluripotent stem cells. The present inventors have further discovered that cells in the obtained embryoid body-like cell clusters had properties that pluripotent/multipotent stem cells which have been conventionally reported do not have. The present inventors have further examined proteins expressed by cells in the obtained cell clusters, and thus they have discovered that the cells exert expression patterns differing from those exerted by conventionally reported pluripotent stem cells such as ES cells and iPS cells.

The present inventors have further discovered that SSEA-3 is expressed as a surface antigen of the above pluripotent stem cells and that the above pluripotent stem cells can also be isolated from body tissue using SSEA-3 expression as an marker.

The present inventors have also discovered that the above pluripotent stem cells are novel type of pluripotent stem cells that differ from conventionally reported pluripotent stem cells such as ES cells and iPS cells. Specifically, the present inventors have discovered that the pluripotent stem cells can be directly obtained from body tissue without any induction operation. Thus, the present inventors have completed the present invention. The present inventors have designated the pluripotent stem cells Muse cells (Multilineage-differentiating Stress Enduring cells).

The present invention is as follows.
[1] A SSEA-3-positive pluripotent stem cell, which can be isolated from body tissue.

The pluripotent stem cells can be isolated from a culture product of body tissue such as cultured fibroblasts and myeloid stem cells and can also be isolated in the form of single cells.

[2] The pluripotent stem cell according to [1], which is positive for CD105.

[3] The pluripotent stem cell according to [1] or [2], which is negative for CD117 (c-Kit) and negative for CD146.

[4] The pluripotent stem cell according to [1] or [2], which is negative for CD117, negative for CD146, negative for NG2, negative for CD34, negative for vWF, and negative for CD271.

[5] The pluripotent stem cell according to [1] or [2], which is negative for CD34, negative for CD117, negative for CD146, negative for CD271, negative for NG2, negative for vWF, negative for Sox10, negative for Snail, negative for Slug, negative for Tyrp1, and negative for Dct.

[6] The pluripotent stem cell according to any one of [1] to [5], which has low or no telomerase activity.

[7] The pluripotent stem cell according to any one of [1] to [6], which is capable of differentiating into the three germ layers.

The pluripotent stem cells of the present invention are capable of differentiating into the three germ layers through in vitro adherent culture. Specifically, the pluripotent stem cells can differentiate into cells representative of the three germ layers, skin, liver, nerve, muscle, bone, fat, and the like through in vitro induction culture. Also, the pluripotent stem cells are capable of differentiating into cells characteristic of the three germ layers when transplanted in vivo into the testis. Furthermore, the pluripotent stem cells are capable of surviving and differentiating into organs (e.g., skin, spinal cord, liver, and muscle) when transplanted to the damaged organs via intravenous injection into a living body.

[8] The pluripotent stem cell according to any one of [1] to [7], which does not undergo neoplastic proliferation.

The pluripotent stem cells of the present invention have a property such that they grow at a growth rate of about 1.3 days/cell division by suspension culture but stop the growth within about 10 days and also have a property such that when transplanted into the testis, they do not become cancerous for at least a half year.

[9] The pluripotent stem cell according to any one of [1] to [8], which has self-renewal capability.

The pluripotent stem cells of the present invention can be grown through repetition of suspension culture and adherent culture. Also, the pluripotent stem cells of the present invention undergo asymmetric division as in the case of other somatic stem cells.

[10] The pluripotent stem cell according to any one of [1] to [9], which is resistant to stress.

[11] The pluripotent stem cell according to any one of [1] to [10], which has high phagocytic ability.

[12] The pluripotent stem cell according to any one of [1] to [11], which is positive for at least one of the 22 following odorant receptors:

olfactory receptor, family 8, subfamily G, member 2 (OR8G2);
olfactory receptor, family 7, subfamily G, member 3 (OR7G3);
olfactory receptor, family 4, subfamily D, member 5 (OR4D5);
olfactory receptor, family 5, subfamily AP, member 2 (OR5AP2);
olfactory receptor, family 10, subfamily H, member 4 (OR10H4);
olfactory receptor, family 10, subfamily T, member 2 (OR10T2);
olfactory receptor, family 2, subfamily M, member 2 (OR2M2);
olfactory receptor, family 2, subfamily T, member 5 (OR2T5);
olfactory receptor, family 7, subfamily D, member 4 (OR7D4);
olfactory receptor, family 1, subfamily L, member 3 (OR1L3);
olfactory receptor, family 4, subfamily N, member 4 (OR4N4);
olfactory receptor, family 2, subfamily A, member 7 (OR2A7);
guanine nucleotide binding protein (G protein), alpha activating activity polypeptide, olfactory type (GNAL);
olfactory receptor, family 6, subfamily A, member 2 (OR6A2);
olfactory receptor, family 2, subfamily B, member 6 (OR2B6);
olfactory receptor, family 2, subfamily C, member 1 (OR2C1);
olfactory receptor, family 52, subfamily A, member 1 (OR52A1);
olfactory receptor, family 10, subfamily H, member 3 (OR10H3);
olfactory receptor, family 10, subfamily H, member 2 (OR10H2);
olfactory receptor, family 51, subfamily E, member 2 (OR51E2);
olfactory receptor, family 5, subfamily P, member 2 (OR5P2); and
olfactory receptor, family 10, subfamily P, member 1 (OR10P1).

[13] The pluripotent stem cell according to any one of [1] to [12], which is positive for at least one of the 5 following chemokine receptors:

chemokine (C—C motif) receptor 5 (CCR5);
chemokine (C—X—C motif) receptor 4 (CXCR4);
chemokine (C—C motif) receptor 1 (CCR1);
Duffy blood group, chemokine receptor (DARC); and
chemokine (C—X—C motif) receptor 7 (CXCR7).

[14] The pluripotent stem cell according to any one of [1] to [13], which is derived from mesodermal tissue or mesenchymal tissue.

[15] A cell cluster or a cell fraction, which contains the pluripotent stem cell according to any one of [1] to [14].

[16] A method for isolating a pluripotent stem cell or a pluripotent cell fraction from body tissue, which uses at least one of the following properties (i) to (vi) as an index:

(i) being positive for SSEA-3;
(ii) being positive for CD105;
(iii) being negative for CD117 and negative for CD146;
(iv) being negative for CD117, negative for CD146, negative for NG2, negative for CD34, negative for vWF, and negative for CD271;
(v) being negative for CD34, negative for CD117, negative for CD146, negative for CD271, negative for NG2, negative for vWF, negative for Sox10, negative for Snail, negative for Slug, negative for Tyrp1, and negative for Dct; and
(vi) having low or no telomerase activity.

[17] A method for isolating a pluripotent stem cell or a pluripotent cell fraction, which comprises exposing body tissue-derived cells to cellular stress and then collecting surviving cells.

[18] The method for isolating a pluripotent stem cell or a pluripotent cell fraction according to [17], wherein cellular stress is selected from among protease treatment, culture under low-oxygen conditions, culture under low phosphate conditions, culture under serum starvation conditions, culture in a sugar starvation state, culture under exposure to radiation, culture under exposure to heat shock, culture in the presence of a toxic substance, culture in the presence of active oxygen, culture under mechanical stimulation, and culture under pressure treatment.

[19] The method for isolating a pluripotent stem cell or a pluripotent cell fraction according to [18], wherein the cellular stress is trypsin incubation.

[20] A pluripotent stem cell, which is a cell derived or induced from the pluripotent stem cell according to any one of [1] to [14].

Examples of the derived cell or the induced cell include cells induced by gene transfer or addition of a compound. Another example thereof is an iPS cell from the stem cell of the present invention.

[21] A differentiated cell, which is a cell derived or induced from the pluripotent stem cell according to any one of [1] to [14].

[22] A pharmaceutical composition, which comprises the pluripotent stem cell according to any one of [1] to [14] and [20].

[23] A pharmaceutical composition, which comprises the differentiated cell according to [21].

The specification includes part or all of the contents as disclosed in the specifications and/or drawings of U.S. Provisional Application No. 61/213,788 and U.S. Provisional Application No. 61/290,159, which are priority documents of the present application.

BRIEF DESCRIPTION OF THE DRAWINGS

FIG. 1-1 shows the relationship among mesenchymal cell fractions, Muse cells, and M-clusters (Muse cell-derived embryoid body-like cell clusters). As shown in FIG. 1, SSEA-3-positive cells are directly separated and then cultured by suspension culture without exposure to long-term stress, so that M-clusters can be obtained.

FIG. 1-2 shows a method for causing the growth of Muse cells in large amounts.

FIG. 2 shows factors, the ratio of the expression level thereof in a M-cluster to that in a naive cell fraction was high.

FIG. 3 shows factors, the ratio of the expression level thereof in a M-cluster to that in human ES cells was high.

FIG. 6a shows a single cell (Bar=10 μm) in a Muse-enriched cell fraction, FIG. 6b shows a human ES cell-derived embryoid body cell cluster (Bar=25 μm), FIG. 6c shows a M-cluster (Bar=25 μm) with a diameter of about 25 μm, FIG. 6d shows a human ES-derived cell cluster (on day 4) stained by alkaline phosphatase staining (Bar=25 μm), and FIGS. 6e-g show immunologically stained images of Oct3/4(e), Sox2(f), and PAR4(g) in M-clusters.

FIG. 7-1 shows photos showing the characteristics of cell clusters from H-fibroblast fractions and human MSC(H-MSC) fractions. FIGS. 7-1 a and b show cell clusters (Bar=100 μm) spontaneously formed by general adherent culture for naive human MSC fractions. FIGS. 7-1 c and d show the state of an H-fibroblast-1 fraction on day 0 (c) and day 7 (d) subjected to long-term trypsin incubation followed by MC culture (Bar=100 μm). An arrow head in FIG. 7-1 d indicates a M-cluster. FIGS. 7-1e and f show M-clusters formed from an H-fibroblast-1 fraction on day 7 of MC culture (Bar=50 μm).

FIG. 7-2 shows photos showing the characteristics of cell clusters from H-fibroblast fractions and human MSC(H-MSC) fractions. FIGS. 7-2 g-l show the results of immunostaining; that is, show the localization of Nanog (FIGS. 7-2 g and j), Oct3/4 (FIGS. 7-2 h), SSEA-3 (FIG. 7-2 i), PAR4 (FIG. 7-2 k), and Sox2 (FIG. 7-2 l) in M-clusters (FIGS. 7-2 g, i, and k) formed from H-fibroblast fractions and M-clusters (FIGS. 7-2 h, j, and l) formed from H-MSC fractions (Bar=50 μm).

FIG. 7-3 shows photos showing the characteristics of cell clusters from H-fibroblast fractions and human MSC (H-MSC) fractions. FIGS. 7-3 m-o show the results of alkaline phosphatase staining for human ES cells (FIG. 7-3 m), M-clusters (FIG. 7-3 n) from H-fibroblast fractions, and naive H-fibroblast-1 fractions (FIG. 7-3o) (Bar=50 μm).

FIG. 7-4 shows electron micrographs showing the characteristics of cell clusters from H-fibroblast fractions and human MSC(H-MSC) fractions. FIGS. 7-4 p-r show electron microscopic images of human ES cell embryoid bodies (FIG. 7-4 p, on day 3 of MC culture), H-fibroblast-1 fraction-derived M-clusters (FIGS. 7-4 q and r, on day 5 of MC culture) (Bar=5 μm).

FIG. 8-1 shows the clonality and self-renewal of M-clusters. Specifically, FIG. 8-1 shows the outline of an experiment conducted for determination of the clonality and self-renewal of Muse cells.

FIG. 8-2 shows the growth rate of suspended Muse cells.

FIG. 8-3 shows a normal karyotype of cells clonally expanded from a single M-cluster (H-fibroblast-1-derived, $1^{st}$ generation (cycle)).

FIG. 9-1 shows the differentiation of M-clusters. FIGS. 9-1 a-c show immunologically stained images showing the localization of α smooth muscle actin and neurofilaments (FIGS. 9-1a and b) and α-fetoprotein (FIG. 9-1c) in differentiated cell clusters from an H-fiboroblast-1 fraction (Bar=500 μm in FIG. 9-1a; Bar=50 μm in FIGS. 9-1b and c). Arrow heads in FIG. 9-1a indicate adhered M-clusters.

FIG. 9-2 shows the results of RT-PCR analysis for α-fetoprotein (α-FP) expression, GATA6 expression, MAP-2 expression, and Nkx2.5 expression in cell populations prepared by culturing a naive cell fraction, and $1^{st}$-generation and $3^{rd}$-generation M-clusters from H-fibroblast fractions on gelatin so as to induce spontaneous differentiation. As positive controls, human fetus liver was used for α-FP and whole human embryos were used for GATA6, MAP-2, and Nkx2.5.

FIGS. 9-3 e-l show the testes of immunodeficient mice to which a Muse-enriched cell fraction was administered. FIG. 9-3e shows a control intact testis, a testis obtained via administration of mouse ES cells (mES cells) (week 8), a testis obtained via administration of MEF (feeder cells) (week 8), a testis obtained via administration of a M-cluster (M-clusters) (month 6), and a testis obtained via administration of a Muse-enriched cell fraction (Muse) (month 6). FIGS. 9-3f-i show immunostained images of neurofilament M (FIG. 9-3f, stained green in the photo), α-fetoprotein (FIG. 9-3g, stained green in the photo), and smooth muscle actin (FIG. 9-3h, stained red in the photo) in testicular tissue obtained via administration of Muse-enriched cell fractions or M-clusters (Bar=50 μm). Three panels in FIG. 9-3i show double-stained images of human mitochondria (stained green) and smooth muscle actin (stained red) (Bar=20 μm).

FIGS. 9-3*j-l* show images of testicular tissue obtained via administration of Muse-enriched cell fractions (FIGS. 9*j* and *k*). The tube-like structure as observed in FIG. 9*k* is stained with an antibody against human mitochondria (Bar=500 μm in FIG. 9-3*j*; Bar=50 μm in FIGS. 9-3*k-l*).

FIG. 10*b* shows the telomerase activity of H-MSC-derived naive cell fractions (Naive), Muse-enriched cell fractions (Muse), and M-clusters (day 7). Heat-inactivated samples (Heat) were used as negative controls.

FIG. 12*a* shows M-clusters formed by performing MC culture (8 hr-hBM-MC, 7 days) for mononuclear cell fractions isolated from human bone marrow and then subjected to 8 hr-long trypsin incubation (Bar=100 μm). FIG. 12*b* shows an alkaline phosphatase-stained image of M-clusters formed by 8 hr-hBM-MC (7 days) (Bar=50 μm).

FIG. 15-1 shows photos showing: a stained image of SSEA-3 (+) cells (left in 15-1*a*) in naive cell fractions; and a stained image of SSEA-3 (+) cells (right in 15-1*a*) that clonally expanded from single M-clusters from SSEA-3 (+) cells collected by FACS sorting. Each bar in this figure indicates 100 μm.

FIG. 15-2 shows photos of stained images showing the localization of Numblike (green) that is a factor involved in asymmetric division during cell division of Muse cells (H-fibroblasts). Each bar in this figure indicates 100 μm.

FIG. 15-3 shows electron micrographs showing H-fibroblast-derived SSEA-3 (−) cells (FIG. 15-3*c*) and SSEA-3 (+) cells (FIG. 15-3*d*). Each bar in this figure indicates 5 μm.

FIG. 15-4 shows photos of stained images showing Oct3/4 (green) (FIG. 15-4*e*), Sox2 (green) (FIG. 15-4*f*), and SSEA-3 (red) (FIG. 15-4*g*) in H-fibroblast-derived Muse cells.

FIG. 16-1 shows photos showing the differentiation of GFP-labeled SSEA-3 (+) Muse cell fractions in damaged tissue of severely immunodeficient mice (Nog mice). FIGS. 16-1N and O show GFP (+) cells of a spinal cord damaged due to compression (4 weeks later), expressing neurofilaments (red) and human golgi complexes (white). FIG. 16-1 O shows an enlarged image of a part enclosed by a square in FIG. 16-1 N. FIG. 16-1P shows GFP (+) target cells of a damaged liver (4 weeks later), expressing human albumin (red) and human golgi complexes (white).

FIG. 16-2 shows photos showing the expression of human albumin in the liver into which SSEA-3 (+) Muse cells were transplanted, as examined by RT-PCR.

FIG. 16-3 shows photos showing the differentiation of GFP-labeled SSEA-3 (+) Muse cell fractions in damaged tissue of severely immunodeficient mice (Nog mice). Specifically, the photos show GFP (+) cells of muscle (3 weeks later) expressing human dystrophin (red).

FIG. 17-1 shows photos showing the differentiation of cells grown from M-clusters formed from single Muse cells. FIGS. 17-1 A-D show the results of neutralization. FIG. 17-1A shows the thus formed spheres. Furthermore, as immunostaining data for spheres, FIG. 17-1B shows the expression of nestin, FIG. 17-1C shows the expression of Musashi, and FIG. 17-1D shows the expression of NuroD. FIG. 17-1E shows MAP-2 (+) cells obtained by further causing these spheres to differentiate into neural cells. FIGS. 17-1F-G show the results of bone cell induction and specifically show the expression of osteocalcin (F) and ALP (G). FIGS. 17-1H and I show the results of adipocyte induction. FIG. 17-1H shows cells containing lipid droplets and FIG. 17-1I shows the result of oil red staining. FIGS. 17-1J shows the result of hepatocyte induction; that is, α-fetoprotein (+) cells.

FIG. 17-2 shows photos showing the expression of human albumin and human α-fetoprotein in cells induced by hepatocyte induction, as examined by RT-PCR.

FIG. 18-1 shows photos showing the expression of Sox10, Snail, Slug, Tyrp1, and Dct in SSEA-3 (+) Muse cells, as examined by RT-PCR.

FIG. 18-2 shows the expression of NG2, CD34, vWF, CD117, CD146, and CD271, as analyzed by FACS. In naive human dermal fibroblasts, NG2 that is a pericyte marker and CD34 and vWF that are endothelial progenitor cell markers were found to be negative. They were also found to be negative in SSEA-3 (+) cells. Few naive human dermal fibroblasts were found to be positive for CD117 that is a melanoblast marker, CD146 that is a pericyte marker, and CD271 that is a NCSC marker (0.2%, 0.2%, and 0.8%, respectively), but were not thought to be Muse cells since they were SSEA-3 (−) cells.

FIG. 18-3 shows that a Muse cell phagocytized ferrite.

FIG. 19*a* shows a state of human iPS cells induced from dermal fibroblast (NHDF)-derived Muse cells. FIGS. 19*b-f* show the expression of pluripotent cell markers ("b" shows the expression of Nonog, "c" shows the expression of Oct3/4, "d" shows the expression of Sox2, "e" shows the expression of SSEA-3, and "f" shows the expression of Tra-1-60).

FIG. 22-1 shows photos showing the results of Tra-1-81 immunostaining of colonies formed by SSEA-3 (+) and (−) cells on day 30 after culturing on MEF feeder cells following introduction of Oct3/4, Sox2, Klf4, and c-Myc with retrovirus. Human ES cells were used as controls. Colonies (a1) from SSEA-3 (+) cells and human ES cells (a2) were positive for Tra-1-81, but all colonies from SSEA-3 (−) cells were negative for the same.

FIG. 22-2 shows photos showing the expression of pluripotency markers (endogenous Oct3/4 (endo Oct), endogenous Sox2 (endo Sox2), Nanog, endogenous Klf4 (endo Klf4), Rex1, and UTF1) for SSEA-3 (+) and (−) cells at a stage after 30 days of culture on MEF as in 22-1. In the SSEA-3 (−) cell population, no Sox2 and Nanog signals were observed.

FIG. 22-3 shows photos showing colonies (FIGS. 22-3D and D1) that grew from iPS cells (Muse cell-derived iPS cells) (FIGS. 22-3C and C1) induced from Muse cells and from SSEA-3 (−) cells.

FIG. 23-1 shows photos showing in vitro differentiation of iPS cells induced from dermal fibroblast (NHDF)-derived Muse cells. FIG. 23-1i shows the expression of α-fetoprotein (green) that is an endodermal marker and smooth muscle actin (red (blue indicates DNA)) that is a mesodermal marker. FIG. 23-1j shows the expression of neurofilament (green) that is an ectodermal marker.

FIG. 23-2 shows the results of RT-PCR analysis for in vitro differentiation of iPS cells induced from Muse cells. FIG. 23-2 specifically shows the expression of markers for the 3 germ layers.

FIG. 23-3 shows photos showing tissue structures of teratomas formed from iPS cells induced from dermal fibroblast (NHDF)-derived Muse cells. FIG. 23-3 specifically shows differentiation of iPS cells into various types of tissue, as revealed by HE (Hematoxylin and eosin) staining. FIG. 23-3m shows cartilage, FIG. 23-3n shows muscle, FIG. 23-3o shows neural epithelium, FIG. 23-3p shows pigmented epithelium, and FIG. 23-3q shows columnar epithelium.

FIG. 25 shows the results of quantitative PCR for factors involved in the cell cycle of naive fibroblasts (Naive), M-clusters, and iPS cells. Among columns denoted with "/Naive," open columns indicate that the ratio of Muse fractions or M-clusters to naive cells is less than 2 (2:1) and higher than ½ (1:2). Also, filled columns indicate that the same ratio is higher than 2 (2:1). Columns shaded with oblique lines indicate that the same ratio is lower than ½ (1:2). Among columns denoted with "/iPS," Symbol "*" indicates that the gene expression level in M-clusters is higher than that in iPS cells. Symbol "**" indicates that the gene expression level in iPS cells is higher than that in M-clusters.

FIG. 26 shows the results of quantitative PCR for factors involved in pluripotency and the undifferentiated cell state of naive fibroblasts (Naive), M-clusters, and iPS cells. The meaning of each column is as defined in FIG. 25.

FIG. 27 shows the summary of a research report concerning the induction efficiency of iPS cell lines prepared in human and mouse models. FIG. 27 shows combinations of transcription factors inducing nuclear reprogramming.

FIG. 28-1 shows the ratio of gene expression levels between (i) Muse cells derived from bone marrow (D24 EB) or human dermal fibroblasts (NHDF EB) and (ii) human embryonic stem cells (hES).

FIG. 28-2 shows the ratio of gene expression levels between (i) Muse cells derived from bone marrow (D24 EB) or human dermal fibroblasts (NHDF EB) and (ii) human embryonic stem cells (hES).

DETAILED DESCRIPTION OF THE PREFERRED EMBODIMENTS

Figures 1, 2:
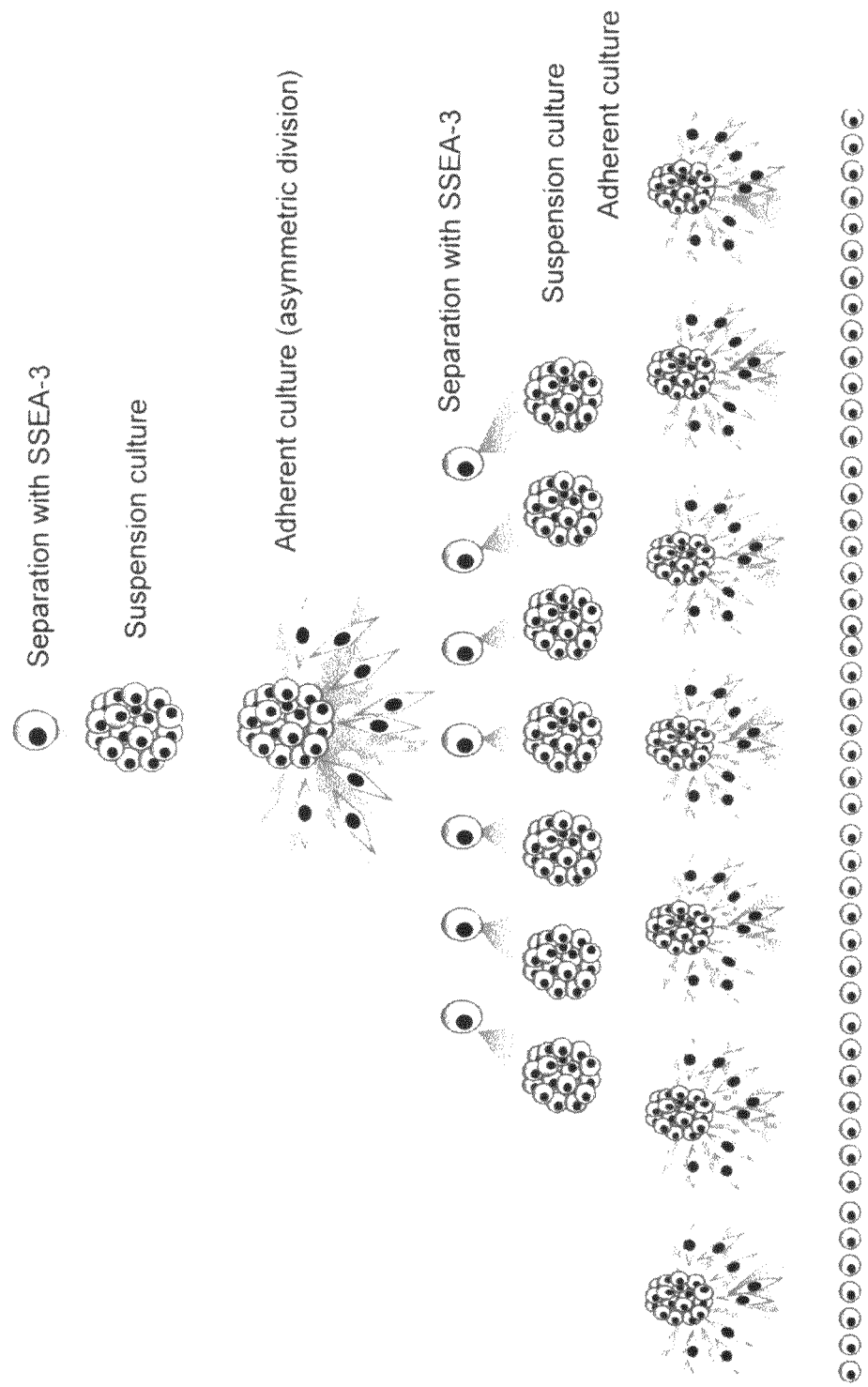

The present invention will be described in detail as follows.

The present invention relates to pluripotent stem cells or pluripotent stem cell fractions that can be directly obtained from body tissue of a living body (in vivo), a method for isolating the pluripotent stem cells or the pluripotent stem cell fractions, and the body tissue-derived pluripotent stem cells or pluripotent stem cell fractions obtained by the method. The pluripotent stem cells of the present invention are referred to as Muse cells (multilineage-differentiating stress enduring cells).

In the present invention, the term "cell fraction" refers to a cell population containing at least a given amount of a cell to be isolated. For example, the term "pluripotent stem cell fraction" refers to a cell population containing a pluripotent stem cell in an amount corresponding to 1% or more thereof, 10% or more thereof, 30% or more thereof, 50% or more thereof, 70% or more thereof, 90% or more thereof, or 95% or more thereof. Examples thereof include cell clusters obtained via culture of pluripotent stem cells and cell populations obtained via enrichment of pluripotent stem cells. Also, the cell fraction may also be referred to as a substantially homogenous cell fraction.

The term "living body" refers to a living mammalian body, and it specifically refers to an animal body that undergoes development to some extent. In the present invention, examples of such living body do not include fertilized eggs or embryos at development stages before the blastula stage, but include embryos at development stages on and after the blastula stage, such as fetuses and blastulae. Examples of mammals include, but are not limited to, primates such as humans and monkeys, rodents such as mice, rats, rabbits, and guinea pigs, cats, dogs, sheep, pigs, cattle, horses, donkeys, goats, and ferrets. The pluripotent stem cells of the present invention are clearly distinguished from embryonic stem cells (ES cells) or embryonic germ stem cells (EG cells) in that they are from living body tissue.

The term "mesodermal tissue" refers to tissue of mesodermal origin that appears in the course of initial development of an animal. Examples of mesodermal tissue include tissue of the muscular system, connective tissue, tissue of the circulatory system, tissue of the excretory system, and tissue of the genital system. For example, the pluripotent stem cells of the present invention can be obtained from bone marrow fluid or skin tissue such as dermis connective tissue.

The term "mesenchymal tissue" refers to tissue such as bone, cartilage, fat, blood, bone marrow, skeletal muscle, dermis, ligament, tendon, and heart tissue. For example, the pluripotent stem cells of the present invention can be obtained from the bone marrow or skin. Also, the pluripotent stem cells can also be obtained from the umbilical cord.

The expression "cells can be directly obtained from tissue" means that cells can be isolated from tissue without any artificial induction operation such as introduction of a foreign gene or a foreign protein or treatment with a compound (e.g., administration of a compound). Such foreign gene may be, but is not limited to, a gene capable of reprogramming the nucleus of a somatic cell, for example. Examples of such foreign gene include Oct family genes such as an Oct3/4 gene, Klf family genes such as a Klf gene, Myc family genes such as a c-Myc gene, and Sox family genes such as a Sox2 gene. Also, examples of a foreign protein include proteins encoded by these genes and cytokines. Furthermore, examples of a compound include a low-molecular-weight compound capable of inducing the expression of the above gene that can reprogram the nucleus of a somatic cell, DMSO, a compound that can function as a reducing agent, and a DNA methylating agent. The pluripotent stem cells of the present invention are clearly distinguished from iPS cells (induced pluripotent stem cells) and ES cells in that the pluripotent stem cells of the present invention can be directly obtained from living bodies or tissue. In addition, in the present invention, cell culture, isolation of a cell or a cell fraction using a cell surface marker as an index, exposure of cells to cellular stress, and provision of a physical impact on cells are not included in examples of artificial induction operation. Also, the pluripotent cells of the present invention may also be characterized in that they can be obtained without requiring reprogramming or induction of dedifferentiation.

The pluripotent stem cells of the present invention are thought to be present in mesodermal tissue or mesenchymal tissue, or the like of a living body. In the present invention, cells or cell fractions existing in these types of tissue are isolated. The pluripotent stem cells of the present invention are present in the bone marrow, for example, so that they may be supplied from the bone marrow to each tissue of a living body via blood or the like. Hence, the pluripotent stem cells can be isolated from the bone marrow, each tissue of a living body, such as skin, and even blood.

The term "pluripotent stem cell(s)" refers to cells having pluripotency and having the following properties.
(1) The pluripotent stem cells express pluripotency markers such as Nanog, Oct3/4, SSEA-3, PAR-4, and Sox2.
(2) The pluripotent stem cells exhibit clonality by which they expand from a single cell and keep producing clones of themselves.
(3) The pluripotent stem cells exhibit self-renewal capability.
(4) The pluripotent stem cells can differentiate in vitro and in vivo into the three germ layers (endodermal cell lineage, mesodermal cell lineage, and ectodermal cell lineage).
(5) The pluripotent stem cells differentiate into the three germ layers when transplanted into the testis or subcutaneous tissue of a mouse.
(6) The pluripotent stem cells are found to be positive through alkaline phosphatase staining.

The pluripotent stem cells of the present invention are clearly distinguished from adult stem cells and tissue stem cells in that pluripotent stem cells of the present invention have pluripotency. Also, the pluripotent stem cells of the present invention are clearly distinguished from cell fractions such as bone marrow stromal cells (MSC) in that pluripotent stem cells of the present invention are isolated in the form of a single cell or a plurality of cells having pluripotency.

Moreover, the pluripotent stem cells of the present invention have the following properties.
(i) The growth rate is relatively gentle and the division cycle takes 1 day or more, such as 1.2-1.5 days. However, the pluripotent stem cells do not exert infinite proliferation in a manner similar to ES cells or iPS cells.
(ii) When transplanted into an immunodeficient mouse, the pluripotent stem cells differentiate into an endodermal cell lineage, a mesodermal cell lineage, and an ectodermal cell lineage. The pluripotent stem cells are characterized in that they do not become cancerous for a half year or longer, unlike ES cells or iPS cells, whereby teratomas become cancerous within a short time period.
(iii) The pluripotent stem cells form embryoid body-like cell clusters as a result of suspension culture.
(iv) The pluripotent stem cells form embryoid body-like cell clusters as a result of suspension culture and stop growth within about 10 days. Subsequently, when the clusters are transferred for adherent culture, they start to grow again.
(v) Asymmetric division is associated with growth.
(vi) The karyotypes of the cells are normal.
(vii) The pluripotent stem cells have no or low telomerase activity. The expression " . . . have no or low telomerase activity" refers to no or low telomerase activity being detected when such activity is detected using a TRAPEZE XL telomerase detection kit (Millipore), for example. The term "low telomerase activity" refers to a situation in which cells have telomerase activity to the same degree as that of human fibroblasts or have telomerase activity that is 1/5 or less and preferably 1/10 or less that of Hela cells.
(viii) Regarding methylation state, methylation levels in Nanog and Oct3/4 promoter regions are low in iPS cells induced from Muse cells.
(ix) The pluripotent stem cells exhibit high phagocytic ability.
(x) The pluripotent stem cells exhibit no neoplastic growth. Here, the expression " . . . cells exhibit no neoplastic growth" refers to a situation in which, when suspension culture is performed, the cells stop their growth at the time when their clusters reach a predetermined size and do not undergo infinite growth. Moreover, such expression refers to a situation in which, when such cells are transplanted into the testis of an immunodeficient mouse, no teratoma is formed. In addition, the above (i) to (iv) and the like also relate to the fact that the relevant cells (clusters) do not undergo neoplastic growth.

Specifically, the cells of the present invention are the following pluripotent stem cells, for example:
(A) pluripotent stem cells that are obtained from mesodermal tissue, mesenchymal tissue, or the like of a living body and can be directly obtained without introduction of a chemical substance, a foreign gene, or a foreign protein into such cells;
(B) pluripotent stem cells having the property of (1) above, wherein mesodermal tissue or mesenchymal tissue of a living body is selected from the group consisting of bone marrow, skin, blood, umbilical cord, and fat;
(C) the pluripotent stem cells of (A) or (B) above that can be obtained without reprogramming or induction of dedifferentiation;
(D) the pluripotent stem cells of (A) or (B) above that do not become cancerous at least within half a year after being transplanted into the testis;
(E) the pluripotent stem cells of (A) or (B) above that do not undergo infinite growth, unlike ES cells and iPS cells; or (F) pluripotent stem cells from mesodermal tissue or mesenchymal tissue of a living body, which survive when treated with protease and thus are resistant to protease.

Moreover, the pluripotent stem cells of the present invention can be isolated by placing cellular stress on the cells of mesodermal tissue or mesenchymal tissue of a living body and then collecting surviving cells. Here, the term "cellular stress" refers to external stress. Specifically, cells are exposed to such stress via protease treatment, culture under low-oxygen conditions, culture under low phosphate conditions, culture under serum starvation conditions, culture in a sugar starvation state, culture under exposure to radiation, culture under exposure to heat shock, culture in the presence of a toxic substance, culture in the presence of active oxygen, culture under mechanical stimulation, culture under pressure treatment, or the like. Of these examples, protease treatment, and specifically, culture in the presence of protease, is preferred. Protease is not limited. Serine protease such as trypsin and chymotrypsin, aspartic protease such as pepsin, cysteine protease such as papain and chymopapain, metalloprotease such as thermolysin, glutamic protease, N-terminal threonine protease, and the like can be used. The concentration of protease to be added for culture is not limited. In general, concentrations to be employed for removal of adherent cells that are cultured in petri dishes or the like may be employed herein. The pluripotent stem cells of the present invention can be said to be stem cells having resistance to the above-mentioned external stresses, such as cells having resistance to trypsin.

Examples of mesodermal tissue and mesenchymal tissue of a living body include, but are not limited to, bone-marrow mononuclear cells, fibroblast fractions such as skin cells, pulp tissue, eyeball tissue, and hair root tissue. As cells, both cultured cells and cells collected from tissue can be used. Among these cells, bone marrow cells and skin cells are desired. Examples of such cells include a human bone marrow stromal cell (MSC) fraction and a human dermal fibroblast fraction. A bone marrow stromal cell (MSC) fraction can be obtained by culturing a bone marrow aspirate for 2 to 3 weeks.

Most cells of tissue subjected to the various above stresses will die. Surviving cells include the pluripotent stem cells of the present invention. After stress is placed on cells, dead cells should be removed. However, when protease is used, these dead cells are lysed via the effects of protease.

Also, after stress is placed on cells, a physical impact is provided to the cells to make them become easily disrupted, and then the cells may be removed. A physical impact can be provided by rigorous pipetting, rigorous stirring, vortexing, or the like.

Cellular stress is placed on cells, a physical impact is provided if necessary, and then the resulting cell populations are subjected to centrifugation. The resulting surviving cells are obtained and collected as pellets, so that the pluripotent stem cells of the present invention can be isolated. Also, from the thus obtained cells, the pluripotent stem cells or pluripotent cell fractions of the present invention can be isolated using the following surface markers as indices.

The pluripotent stem cells or pluripotent cell fractions of the present invention can also be isolated by culturing mesodermal tissue, mesenchymal tissue, or the like (in vivo) of a body subjected to stress such as trauma or a burn and then collecting cells that have migrated. Cells of damaged tissue are exposed to stress. Hence, in the present invention, the expression "culture of mesodermal tissue or mesenchymal tissue (in vivo) of a damaged body" also refers to placing cellular stress on cells of mesodermal tissue, mesenchymal tissue, or the like of a living body.

As an example, a method for treating such cells with trypsin is as described below. The concentration of trypsin at this time is not limited. For example, in general culture of adherent cells, the concentrations of trypsin may be concentrations that are employed for removal of adherent cells adhering to a culture vessel, ranging from 0.1% to 1% and preferably ranging from 0.1% to 0.5%, for example. For example, cells can be exposed to external stress by incubating cells (100,000-500,000 cells) from mesodermal tissue, mesenchymal tissue, or the like of a living body in 5 ml of a trypsin solution with the above concentration. The time for trypsin incubation ranges from about 5 to 24 hours and preferably ranges from about 5 to 20 hours. In the present invention, 8 or more hours of trypsin incubation, such as 8 hours or 16 hours of treatment, is long-term trypsin incubation.

After trypsin incubation, a physical impact is desirably provided by pipetting, stirring, vortexing, or the like, as described above. This is performed to remove dead cells or dying cells.

When suspension culture is performed after trypsin incubation, incubation is desirably performed in gel such as methylcellulose gel, in order to prevent cell-to-cell aggregation. Also, a cell culture vessel is desirably coated in advance with poly(2-hydroxyethyl methacrylate) or the like in order to prevent adhesion of cells to the culture vessel and maintain the state of suspension.

When cells exposed to external stress, collected by centrifugation, and then cultured, cells form cell clusters. The size of such a cell cluster ranges in diameter from about 25 μm to 150 μm. The pluripotent stem cells (Muse cells) of the present invention are included in an enriched state within a cell population that has survived after exposure to external stress. Such cell population is referred to as Muse-enriched cell fractions (Muse enriched populations). The percentage of Muse cells in such a Muse-enriched cell fraction differs depending on method of stress treatment.

The fact that the pluripotent stem cells or the pluripotent stem cell fractions of the present invention survive after exposure to stress suggests that the pluripotent stem cells or the pluripotent stem cell fractions of the present invention are resistant to such stress.

Regarding the medium to be used for culturing cells from mesodermal tissue, mesenchymal tissue, or the like of a living body and culture conditions, any medium and culture conditions generally used for culturing animal cells may be employed. Also, a known medium for culturing stem cells may be used. A medium may be appropriately supplemented with serum such as fetal calf serum, antibiotics such as penicillin and streptomycin, and various bioactive substances.

Furthermore, the present invention also encompasses pluripotent stem cells which are derived cells or induced cells of the pluripotent stem cells of the present invention that can be directly obtained from the mesodermal tissue, mesenchymal tissue, or the like of a living body. The term "derived cells or induced cells" refers to cells or cell populations obtained by culturing the pluripotent stem cells or cells obtained by subjecting the pluripotent stem cells to an artificial induction operation such as introduction of a foreign gene. Progeny cells are also included herein. In addition, it is said that iPS cells that had been reported at the time of the present invention are induced from pluripotent stem cells as a result of reprogramming (e.g., introduction of a foreign gene into differentiated cells in body tissue, such as dermal fibroblasts). Cells obtained by subjecting cells (that can be directly obtained from the tissue of the present invention and already have properties as pluripotent stem cells) to an artificial induction operation such as introduction of a foreign gene are distinguished from iPS cells.

Embryoid body-like (EB body-like) cell clusters are obtained through suspension culture of the pluripotent stem cells of the present invention. The present invention also encompasses such embryoid body-like cell clusters and cells contained in such embryoid body-like cell clusters. Embryoid bodies are formed as cell clusters through suspension culture of the pluripotent stem cells of the present invention. At this time, in the present invention, such an embryoid body obtained by culturing the pluripotent stem cells of the present invention is also referred to as a M-cluster (Muse cell-derived embryoid body-like cell cluster). Examples of a method for suspension culture for the formation of embryoid body-like cell clusters include culture using medium containing a water soluble polymer such as methylcellulose (Nakahata, T. et al., Blood 60, 352-361 (1982)) and hanging drop culture (Keller, J. Physiol. (Lond) 168: 131-139, 1998). The present invention also encompasses embryoid body-like cell clusters obtained via self-renewal from the embryoid body-like cell clusters, cells contained in such embryoid body-like cell clusters, and pluripotent stem cells. Here, the term "self-renewal" refers to a situation in which cells contained in embryoid body-like cell clusters are cultured so as to cause the formation of embryoid body-like cell clusters again. Self-renewal may be performed by repeating a cycle once to several instances. Also, the present invention also encompasses cells and tissue, which differentiate from either the above embryoid body-like cell clusters or cells contained in such embryoid body-like cell clusters.

FIG. 1-1 shows the relationship among mesenchymal cell (human fibroblast, human bone marrow stromal cell (MSC), and fresh bone marrow fluid) fractions, Muse cells, and M-clusters. When stress stimulation (e.g., long-term trypsin incubation (LTT)) is imposed upon mesenchymal cell-like cell clusters, Muse cells are enriched, and then cell fractions containing many Muse cells (referred to as a Muse-enriched cell fraction) are obtained. Through suspension culture of Muse cells in the cell fraction, an embryoid body-like cell cluster (M-cluster) is obtained. When embryoid body-like cell clusters are cultured in a culture dish coated with gelatin, cells differentiate into cells of the 3 germ layers. Also, as shown in FIG. 1-1, SSEA-3 (+) cells are directly separated and then suspension culture is performed without exposing cells to long-term stress, so that M-clusters can be obtained.

When the growth of Muse cells is stopped once via suspension culture, Muse cells initiate growth when transferred for adherent culture. Through repetition of separation using suspension culture-adherent culture-SSEA-3 expression as an index, Muse cells can be grown in large amounts (FIG. 1-2).

Furthermore, the pluripotent stem cells or pluripotent cell fractions of the present invention can also be directly isolated from body tissue without exposure to cellular stress. Specifically, the pluripotent stem cells or the pluripotent stem cell fractions of the present invention can be isolated from mesodermal tissue, mesenchymal tissue, or the like of a living body by the following method without an induction operation such as introduction of a foreign gene.

Examples of body tissue include, but are not limited to, mesodermal tissue and mesenchymal tissue of a living body such as bone marrow, skin, and umbilical cord tissue. When bone marrow is used, a mononuclear cell fraction of the bone marrow can be used. Isolation can be performed using a cell surface marker that is expressed richly on the surface of Muse cells. For example, isolation can be performed using SSEA-3 expression as an index. The pluripotent stem cells of the present invention may also be referred to as SSEA-3 (+) Muse cells. Moreover, Muse cells express CD105, which is a pluripotent stem cell marker. Muse cells are positive for SSEA-3, and positive for CD105. Therefore, Muse cells can be isolated using the expression of both SSEA-3 and CD105 as an index. With the use of these cell surface markers, the pluripotent stem cells of the present invention can be isolated in the form of single cells. The thus isolated single cells can be grown by culture. In addition, the present invention encompasses pluripotent stem cells that can be isolated from body tissue of a mammal other than a human using a marker corresponding to SSEA-3.

Meanwhile, Muse cells are negative for NG2, CD34, vWF (von Willebrand factor), c-kit (CD117), CD146, and CD271 (NGFR). Moreover, Muse cells are negative for Sox10, Snail, Slug, Tyrp1, and Dct.

Whether or not cells are negative for surface antigens such as NG2, CD34, vWF, CD117, CD146, and CD271 or whether or not the expression thereof is weak can be determined by microscopically observing whether or not cells are stained with antibodies (against these antigens) labeled with a chromogenic enzyme, a fluorescent compound, or the like. For example, cells are immunostained with these antibodies, so that the presence or the absence of a surface antigen can be determined. The presence or the absence of the same can also be determined using antibody-conjugated magnetic beads. Also, the presence or the absence of a surface antigen can be determined using FACS or a flowcyte meter. As a flowcyte meter, FACSAria (Becton Dickinson), FACS vantage (Becton Dickinson), FACS Calibur (Becton Dickinson), or the like can be used, for example.

Regarding transcription factors such as Sox10, Snail, Slug, Tyrp1, and Dct, the expression thereof can also be examined by a technique such as RT-PCR.

The expression " . . . are negative for these surface antigens" refers to that a situation in which, when FACS analysis is conducted as described above, cells are not sorted as positive cells or when expression is examined by RT-PCR, no expression thereof is confirmed. Even if such surface antigens are expressed to a degree such that they are undetectable by such techniques, cells are designated as negative in the present invention. Also, at the same time, measurement is performed with cells such as hematopoietic stem cells known to be positive for the above markers. When almost no expression is detected or the expression level is significantly lower compared with such positive cells, cells may be designated as negative.

Cells of the present invention can be isolated based on the properties of the aforementioned cell surface antigens.

As described above, Muse cells can be isolated using "being positive for SSEA-3" as an index. Moreover, Muse cells can be isolated using the expression of CD105 as an index. Muse cells can be further isolated using non-expression of at least 1, such as 2, 3, 4, 5, 6, 7, 8, 9, 10, or 11, markers selected from the group consisting of NG2, CD34, vWF (von Willebrand factor), c-kit (CD117), CD146, CD271 (NGFR), Sox10, Snail, Slug, Tyrp1, and Dct, as an index. For example, isolation is possible using non-expression of CD117 and CD146. Furthermore, isolation can be performed using non-expression of CD117, CD146, NG2, CD34, vWF, and CD271 as an index. Furthermore, isolation can be performed using non-expression of the above 11 markers as an index.

When isolation is performed using a surface marker(s), 1 or a plurality of pluripotent stem cells of the present invention can be directly isolated from mesodermal tissue, mesenchymal tissue, or the like of a living body without culture or the like. Also, the pluripotent stem cells of the present invention can be identified and isolated by visually observing the cell morphology using a microscope or the like.

After provision of a cellular stress to mesodermal tissue, mesenchymal tissue, or the like of a living body, isolation may also be performed from a surviving cell group using a surface marker.

Also, the pluripotent stem cells or the pluripotent cell fractions of the present invention can be characterized by high-level expression of another specific factor, in addition to the use of the above markers.

Muse cells that are the pluripotent stem cells of the present invention can be obtained from naive bone marrow stromal cell (MSC) fractions or dermal fibroblast fractions. Muse cells are further cultured, so that Muse cell-derived embryoid body (EB)-like cell clusters are obtained. Through comparison and examination of factors expressed in Muse cells, naive cells, Muse-derived embryoid body-like cell clusters, and human ES cells, a factor expressed at high levels in Muse cells can be detected. Examples of such factors include gene transcription products, proteins, lipids, and saccharides.

FIG. 2 shows factors for which the ratio of the expression level in M-clusters to the same in naive cells is high. In particular, the ratio is high for the following 18 factors.
(i) SSEA-3
(ii) v-fos FBJ murine osteosarcoma viral oncogene homolog
(iii) solute carrier family 16, member 6 (monocarboxylic acid transporter 7)
(iv) tyrosinase-related protein 1
(v) Calcium channel, voltage-dependent, P/Q type, alpha 1A subunit
(vi) chromosome 16 open reading frame 81
(vii) chitinase 3-like 1 (cartilage glycoprotein-39)
(viii) protease, serine, 35
(ix) kynureninase (L-kynurenine hydrolase)
(x) solute carrier family 16, member 6 (monocarboxylic acid transporter 7)
(xi) apolipoprotein E
(xii) synaptotagmin-like 5
(xiii) chitinase 3-like 1 (cartilage glycoprotein-39)
(xiv) ATP-binding cassette, sub-family A (ABC1), member 13
(xv) angiopoietin-like 4
(xvi) prostaglandin-endoperoxide synthase 2 (prostaglandin G/H synthase and cyclooxygenase)
(xvii) stanniocalcin 1
(xviii) coiled-coil domain containing 102B The pluripotent stem cells or the pluripotent stem cell fractions of the present invention are characterized in that at least 2, 3, 4, 5, 6, 7, 8, 9, 10, 11, 12, 13, 14, 15, 16, 17, or 18 factors above are expressed at high levels. Hence, the pluripotent stem cells or the pluripotent stem cell fractions can be isolated using high-level expression of at least 2 factors as an index.

Figures 1, 7:
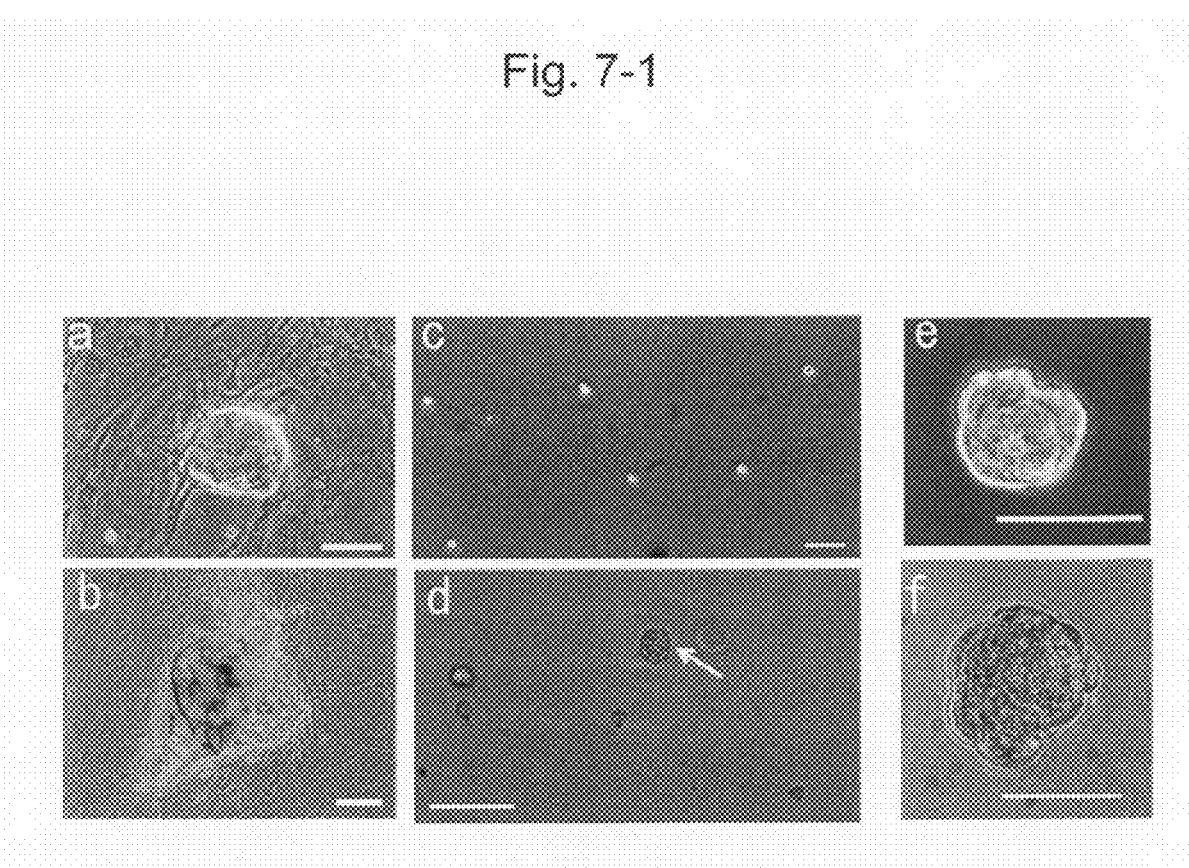
Figures 2, 7:
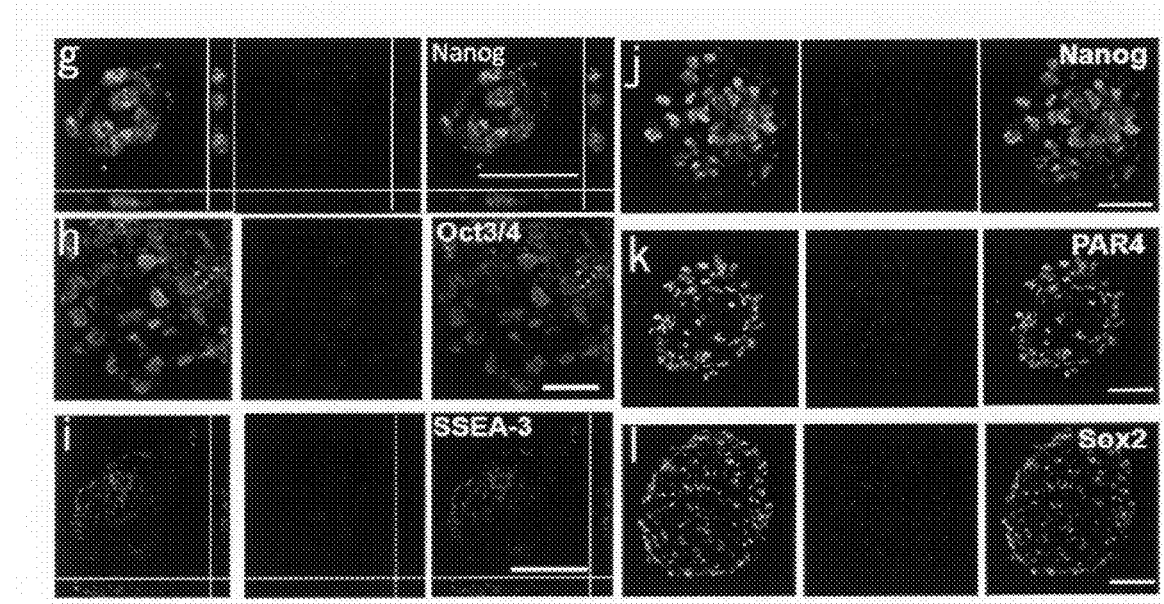
Figures 3, 7:
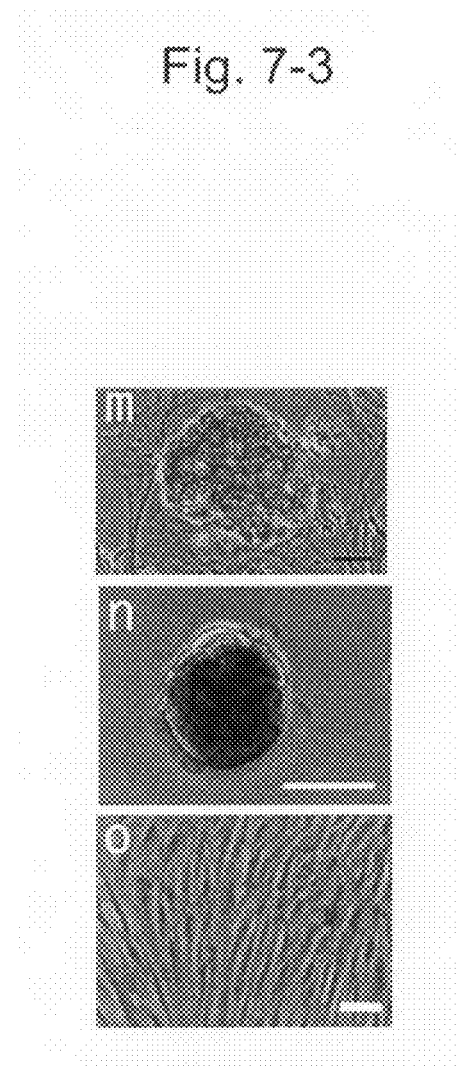

FIG. 3 shows factors for which the ratio of the expression level in M-clusters to the same in human ES cells is high. In particular, the ratio is high in the following 20 factors.
(a) matrix metallopeptidase 1 (interstitial collagenase)
(b) epiregulin
(c) chitinase 3-like 1 (cartilage glycoprotein-39)
(d) Transcribed locus
(e) chitinase 3-like 1 (cartilage glycoprotein-39)
(f) serglycin
(g) mRNA full length insert cDNA clone EUROIMAGE 1913076
(h) Ras and Rab interactor 2
(i) lumican
(j) CLCA family member 2, chloride channel regulator
(k) interleukin 8
(l) Similar to LOC166075
(m) dermatopontin
(n) EGF, latrophilin and seven transmembrane domain containing 1
(o) insulin-like growth factor binding protein 1
(p) solute carrier family 16, member 4 (monocarboxylic acid transporter 5)
(q) serglycin
(r) gremlin 2, cysteine knot superfamily, homolog (*Xenopus laevis*)
(s) insulin-like growth factor binding protein 5
(t) sulfide quinone reductase-like (yeast)

The pluripotent stem cells or the pluripotent stem cell fractions of the present invention are characterized in that at least 2, 3, 4, 5, 6, 7, 8, 9, 10, 11, 12, 13, 14, 15, 16, 17, 18, 19, or 20 factors above are expressed at high levels. Hence, the pluripotent stem cells or the pluripotent stem cell fractions can be isolated using high-level expression of at least 2 factors as an index.

Furthermore, in the pluripotent stem cells or the pluripotent stem cell fractions of the present invention, at least 2 of the above factors (i)-(xviii) and at least 2 of the above factors (a)-(t) may be simultaneously expressed at high levels. Hence, the pluripotent stem cells or the pluripotent stem cell fractions can be isolated using high-level expression of these genes as an index.

Furthermore, the pluripotent stem cells or the pluripotent stem cell fractions of the present invention are characterized in that: factors of an odorant receptor (olfactory receptor) group and factors of a chemokine receptor group, other than pluripotency markers, are expressed; that is, they are positive for specific odorant receptors or chemokine receptors.

Examples of odorant receptors that are expressed in the pluripotent stem cells or the pluripotent stem cell fractions of the present invention include the following 22 receptors.
olfactory receptor, family 8, subfamily G, member 2 (OR8G2);
olfactory receptor, family 7, subfamily G, member 3 (OR7G3);
olfactory receptor, family 4, subfamily D, member 5 (OR4D5);
olfactory receptor, family 5, subfamily AP, member 2 (OR5AP2);
olfactory receptor, family 10, subfamily H, member 4 (OR10H4);
olfactory receptor, family 10, subfamily T, member 2 (OR10T2);
olfactory receptor, family 2, subfamily M, member 2 (OR2M2);
olfactory receptor, family 2, subfamily T, member 5 (OR2T5);
olfactory receptor, family 7, subfamily D, member 4 (OR7D4);
olfactory receptor, family 1, subfamily L, member 3 (OR1L3);
olfactory receptor, family 4, subfamily N, member 4 (OR4N4);

olfactory receptor, family 2, subfamily A, member 7 (OR2A7);
guanine nucleotide binding protein (G protein), alpha activating activity polypeptide, olfactory type (GNAL);
olfactory receptor, family 6, subfamily A, member 2 (OR6A2);
olfactory receptor, family 2, subfamily B, member 6 (OR2B6);
olfactory receptor, family 2, subfamily C, member 1 (OR2C1);
olfactory receptor, family 52, subfamily A, member 1 (OR52A1);
olfactory receptor, family 10, subfamily H, member 3 (OR10H3);
olfactory receptor, family 10, subfamily H, member 2 (OR10H2);
olfactory receptor, family 51, subfamily E, member 2 (OR51E2);
olfactory receptor, family 5, subfamily P, member 2 (OR5P2); and
olfactory receptor, family 10, subfamily P, member 1 (OR10P1)

Examples of a chemokine receptor that is expressed in the pluripotent stem cells or pluripotent stem cell fractions of the present invention include the 5 following receptors.
chemokine (C—C motif) receptor 5 (CCR5);
chemokine (C—X—C motif) receptor 4 (CXCR4);
chemokine (C—C motif) receptor 1 (CCR1);
Duffy blood group, chemokine receptor (DARC); and
chemokine (C—X—C motif) receptor 7 (CXCR7).

The pluripotent stem cells or the pluripotent stem cell fractions of the present invention express at least one of the above olfactory receptors or express at least one of the above chemokine receptors.

Because of the effects of these odorant receptors or chemokine receptors and migratory factors that bind to the receptors, the pluripotent stem cells of the present invention migrate to damaged tissue and then survive and differentiate at the tissue. For example, when the liver, skin, spinal cord, or muscle is damaged, a specific migratory factor and an odorant receptor expressed on the cell surfaces function to cause the pluripotent stem cells to migrate to the relevant tissue, survive at the tissue, and then differentiate into liver (endoderm), skin (ectoderm), spinal cord (ectoderm), or muscle (mesoderm) cells, so that the tissue can be regenerated.

In a Muse-enriched cell fraction richly containing Muse cells that are the pluripotent stem cells of the present invention, Rex1, Sox2, KLF-4, c-Myc, DPPA2, ERAS, GRB7, SPAG9, TDGF1, and the like are upregulated. In a cell cluster of Muse cells, DAZL, DDX4, DPPA4, Stella, Hoxb1, PRDM1, SPRY2, and the like are upregulated.

Also, in pluripotent stem cells or the pluripotent stem cell fractions of the present invention, the expression of CD34 and CD117 hematopoietic stem cell markers is never observed or is observed at an extremely low level.

The present invention encompasses not only Muse cells, but also a cell population resulting from enrichment of Muse cells, a cell population resulting from growth of Muse cells, and a cell population resulting from differentiation of Muse cells. The present invention further encompasses a research kit, a cell chip, and a therapeutic device containing Muse cells or cells derived from Muse cells.

The pluripotent stem cells of the present invention have pluripotency and thus are able to differentiate into all types of tissue. The pluripotent stem cells or the pluripotent cell fractions can be used for regeneration medicine and the like. For example, such cells and cell fractions can be used for regeneration of various types of tissue, various organs, and the like. Specific examples thereof include skin, cerebrospinal cord, liver, and muscle. The pluripotent stem cells or the pluripotent stem cell fractions of the present invention are administered directly to or to an area in the vicinity of injured or damaged tissue, organs, and the like, so that the pluripotent stem cells enter the tissue or organ and differentiate into cells unique to the relevant tissue or organ. In this manner, the pluripotent stem cells can contribute to the regeneration or reconstruction of tissue and organs. Also, the systemic administration of the pluripotent stem cells or pluripotent stem cell fractions is possible by intravenous administration or the like. In this case, the pluripotent stem cells are directed by homing or the like to a damaged tissue or organ, reach and enter the tissue or organ, and then differentiate into cells of the tissue or organ, so as to be able to contribute to tissue or organ regeneration and reconstruction.

Administration can be performed via parenteral administration such as subcutaneous injection, intravenous injection, intramuscular injection, and intraperitoneal injection, oral administration, or intrauterine injection into an embryo, for example. Also, local administration or systemic administration may be performed herein. Local administration can be performed using a catheter, for example. The dose can be appropriately determined depending on an organ to be regenerated, a tissue type, or a size.

Examples of an organ to be regenerated include, but are not limited to, bone marrow, spinal cord, blood, spleen, liver, lungs, bowel, eyes, brain, immune system, circulatory system, bone, connective tissue, muscle, heart, blood vessel, pancreas, central nervous system, peripheral nervous system, kidney, bladder, skin, epithelial appendages, breast-mammary gland, adipose tissue, and mucous membranes of mouth, esophagus, vagina, and anus, for example. Also, examples of diseases to be treated therein include, cancer, cardiovascular disease, metabolic disease, hepatic disease, diabetes mellitus, hepatitis, haemophilia, blood system disease, degenerative or traumatic neurologic disorder such as spinal cord injury, autoimmune disease, genetic defects, connective tissue disease, anemia, infectious disease, graft rejection, ischaemia, inflammation, and damage to skin or muscle.

Cells may be administered with a pharmaceutically acceptable base material. Such base material may be made of a substance with high bio-compatibility, such as collagen or a biodegradable substance. They may be in the form of particles, plates, tubes, vessels, or the like. Cells may be administered after binding thereof to a base material or after causing a base material to contain cells therein.

Also, in vitro differentiation induction is performed for pluripotent stem cells of the present invention, tissue is constructed using cells that have further differentiated, and then the differentiated cells or tissue may be transplanted. Since the pluripotent stem cells of the present invention do not undergo tumorigenic transformation, a probability of canceration of the cells is low and can be said to be safe, even when the undifferentiated pluripotent stem cells of the present invention are contained in the above transplanted differentiated cells or tissue. To prevent rejection of transplanted cells or tissue by a recipient in such regeneration medicine, it is desired that mesodermal tissue, mesenchymal tissue, or the like is collected from a patient to be subjected to regeneration medicine, and then pluripotent stem cells or pluripotent cell fractions of the present invention are isolated from the relevant tissue for use. Furthermore, the pluripotent stem cells or the pluripotent stem cell fractions of the present invention can be used for treatment of diseases due to tissue degeneration or dysfunction. In this case, for example, the pluripotent stem cells or the pluripotent stem cell fractions of the present invention are enriched ex vivo, grown, or caused to differentiate and then returned into the body. For example, the pluripotent stem cells are caused to differentiate into specific tissue cells and then the cells are transplanted into tissue to be treated. Also, in situ cell therapy can be performed by transplantation of such cells. In this case, examples of target cells include hepatic cells, neural cells such as neuronal cells or glial cells, skin cells, and muscle cells such as skeletal muscle cells. The pluripotent stem cells of the present invention are caused to differentiate into these cells, the differentiated cells are transplanted, and then treatment can be performed in situ. Through such treatment, Parkinson's disease, brain infarction, spinal cord injury, myodystrophy, and the like can be treated, for example. Since the pluripotent stem cells of the present invention do not undergo tumorigenic transformation, they unlikely become cancerous and safe even if used for such treatment.

Also, the pluripotent stem cells of the present invention are caused to differentiate to form blood or blood components, so that blood or blood components can be formed ex vivo or in vitro. Examples of such blood components include erythrocytes, leukocytes, and blood platelets. The thus formed blood or blood components can be used for autologous transfusion or cross transfusion.

As described above, when the pluripotent stem cells or the pluripotent stem cell fractions of the present invention are used for treatment, their differentiation may be caused ex vivo, in vivo, or in vitro. The pluripotent stem cells of the present invention differentiate into osteoblasts, chondrocytes, adipocyte, fibroblasts, bone-marrow stroma, skeletal muscle, smooth muscle, myocardium, eyes, endothelium, epithelium, liver, pancreas, hematopoietic system, glia, neuronal cells, or oligodendroglial cell, for example. Differentiation of the pluripotent stem cells of the present invention can be achieved by culturing them in the presence of a differentiation factor. Examples of a differentiation factor include a basic fibroblast growth factor (bFGF), a vascular endothelium growth factor (VEGF), a dimethyl sulfoxide (DMSO), and isoproterenol; or a fibroblast growth factor 4 (FGF4) and a hepatocyte growth factor (HGF). The present invention also encompasses cells that have differentiated from the pluripotent stem cells of the present invention.

When the pluripotent stem cells of the present invention are used for treatment, a gene encoding a protein antitumor substance, a bioactive substance, or the like may be introduced. Therefore, it can be said that the pluripotent stem cells of the present invention have a function for the delivery of a therapeutic agent. Examples of such substance include antiangiogenic agents.

The present invention encompasses materials for cell transplantation therapy or compositions for cell transplantation therapy, or materials for regeneration medicine or compositions for regeneration medicine, which contain Muse cells, embryoid body-like cell clusters formed of Muse cells, and cells or tissue/organs obtained via differentiation from Muse cells or the above embryoid body-like cell clusters. Such a composition contains a pharmaceutically acceptable buffer, diluent, or the like in addition to Muse cells, an embryoid body-like cell cluster formed of Muse cells, or cells or tissue and/or organ obtained through differentiation from Muse cells or the above embryoid body-like cell cluster.

Moreover, cells are collected from a patient, Muse cells are isolated, and then the Muse cells can be used for various diagnoses. For example, a patient's genes are collected from Muse cells and then the gene information is obtained, so that precise diagnosis reflecting the information becomes possible. For example, cells of each tissue and/or organ having the same characteristics (e.g., genetic background) as those of a subject can be obtained by causing differentiation of patient's cell-derived Muse cells. Hence, regarding disease diagnosis, elucidation of pathological conditions, diagnosis for the effects or adverse reactions of drugs, or the like, appropriate diagnosis can be made according to the characteristics of each subject. Specifically, Muse cells, embryoid body-like cell clusters formed of Muse cells, and cells or tissue and/or organs obtained through differentiation of Muse cells or the above embryoid body-like cell clusters can be used as diagnostic materials. For example, the present invention encompasses a method for diagnosing the disease or the like of a subject using Muse cells isolated from the subject or using tissue or an organ (obtained via differentiation from the Muse cells) having the same genetic background as that of the subject.

Also, somatic cells can be obtained in large amounts via differentiation of Muse cells. Hence, basic research such as elucidation of a disease mechanism, development of a therapeutic agent, screening for the effects of a drug or toxicity, drug evaluation, and the like can be performed. Specifically, Muse cells, embryoid body-like cell clusters formed of Muse cells, and cells or tissue and/or organs obtained through differentiation of Muse cells or the above embryoid body-like cell clusters can be used as materials for drug evaluation or drug screening. For example, the present invention encompasses a method for screening for a drug or evaluating a drug, comprising causing differentiation and/or growth of Muse cells, obtaining somatic cells, administering a candidate drug to the somatic cells, and then examining the response of somatic cells.

Also, a Muse cell bank is constructed by constructing a library of various (e.g., various types of HLA) Muse cells, so that a system capable of providing Muse cells to Muse cell application sites according to need can be realized. For example, in addition to the above listed purposes, provision of cells with no (or little) rejections to urgently required cell transplantation therapy can be performed, for example. Specifically, the present invention encompasses a method for constructing a Muse cell library; that is, a Muse cell bank, having different genetic properties, comprising isolating and collecting Muse cells having various genetic properties. Also, a library or a bank can also be constructed using not only Muse cells, but also an embryoid body-like cell cluster formed from Muse cells, and cells or tissue and/or organ obtained through differentiation from Muse cells or the above embryoid body-like cell clusters. In the present invention, libraries or banks that are constructed by obtaining embryoid body-like cell clusters formed of these Muse cells, and cells or tissue and/or organs obtained through differentiation of Muse cells or the above embryoid body-like cell clusters are also referred to as cell libraries or cell banks. The present invention encompasses the thus constructed cell libraries or cell banks. Such cell libraries or cell banks comprise vessels such as a plurality of tubes containing cells and the like having different genetic characteristics. Such cells may also be frozen. For example, when tissue or an organ is transplanted into a subject or regeneration thereof is required, cells appropriate in terms of genetic background or the like of the subject are selected from the above cell library or cell bank. Thus, transplantation or regeneration therapy can be performed using the cells.

The present invention encompasses a therapeutic method, comprising administering, for treatment of a disease, a therapeutically effective dose of the pluripotent stem cells, a cell fraction thereof of the present invention, or cells derived or induced from such cells to a patient who needs treatment. The effective dose can be specified based on the number of cells to be administered, for example, and appropriately determined depending on disease types or severity. In the above therapeutic method, the pluripotent stem cells of the present invention do not form any teratoma, so that no teratoma is formed in a patient. Also, when autologous cell-derived Muse cells are administered, there is no need to cause bone marrow dysfunction by subjecting a patient to radiation exposure, chemotherapy, or the like. When Muse cells that are not autologous cells are used, the above treatment is performed.

Furthermore, Muse cells can be a source of iPS cells (induced pluripotent stem cells). Efficiency for preparation of iPS cells using Muse cells as a source is much higher (at least higher by 25 or more folds) than that of a case of using another type of cells (e.g., dermal fibroblasts not fractioned using SSEA-3 expression as an index) as a source.

iPS cells can be prepared by introducing a specific gene or a specific compound into Muse cells so as to alter cytoplasms. Alterations of cytoplasms include reprogramming or canceration, for which currently known methods or all methods that will be established in the future can be employed.

For example, a gene is introduced into Muse cells according to the description of JP Patent No. 4182742 or the description in FIG. 27, so that iPS cells can be established from Muse cells. Also, in addition to the method described in FIG. 27, it can be said that iPS cells can be established through introduction of a chemical substance, a foreign gene, or a foreign protein. Establishment of iPS cells from Muse cells can be performed by methods described in Examples described later, for example.

The iPS cells obtained as described above from Muse cells may also be referred to as "Muse-derived iPS cells (Muse-iPSC)." The present invention encompasses such Muse-derived iPS cells. Muse-derived iPS cells can be said to be pluripotent stem cells having Muse cell-derived proliferative ability.

Hereafter, the present invention is described in greater detail with reference to the following examples, although the present invention is not limited to these examples Example 1

Preparation and Characterization of Muse-Enriched Cell Fractions and M-Clusters

Materials and Methods

The following cells are used in Examples.

Two strains of human dermal fibroblast fractions (H-fibroblasts) and four strains of human MSC (bone marrow stromal cell) fractions (H-MSC fractions) were used as mesenchymal cells. Human fibroblast fractions were (1) H-fibroblast-1 (normal human fibroblast cells (NHDF), Lonza), and (2) H-fibroblast-2 (adult human dermal fibroblasts (HDFA, ScienCell, Carlsbad, Calif.)). Human MSC fractions, H-MSC-1, -2 and -3 were obtained from Lonza, and H-MSC-4 was obtained from ALLCELLS. Human MSC fractions are specifically described in Pittenger, M. F. et al. Science 284, 143-147 (1999); Dezawa, M. et al. J Clin Invest 113, 1701-1710 (2004); and Dezawa, M. et al. Science 309, 314-317 (2005).

Cells were cultured at 37° C. in α-MEM (alpha-minimum essential medium) containing 10% FBS and 0.1 mg/ml kanamycin with 5% $CO_2$. Cells cultured directly after their shipment were considered to be the $1^{st}$ culture. When cells reached 95% confluence, cells were expanded at a ratio of 1:2 (cell culture solution: medium). In this study cells from the $4^{th}$ to $10^{th}$ subcultures were used.

Human ES cells (hESC) used herein were kyoto hESC-1 (KhES-1) obtained from Kyoto University.

Mouse ES cells (TT2 cells) and human ES cells (KhES-1) were maintained on mouse embryonic feeder (MEF) cells established from 12.5-day embryos of C57BL/6 mice.

Experiments were conducted by the following methods.
1. Stress Conditions for Mesenchymal Cells To perform exposure to stress conditions including culture under poor nutrition, culture under low serum, culture under low $O_2$, repetitive-trypsin incubations and long-term trypsin incubation, the following six conditions were employed:
1) culture in non-serum containing medium (STEMPRO MSC SFM, Invitrogen) for 2 days (serum free);
2) culture in Hanks' Balanced Salt Solution (HBSS) buffer (Invitrogen) for 2 days (HBSS);
3) culture in 10% FBS in α-MEM combined with low $O_2$ (1% $O_2$) for 2 days (10% FBS+Low $O_2$);
4) three consecutive 1-hr incubations (a total of 3 hours of trypsin incubation) (Try 3×1 hr) in trypsin (0.25% trypsin-HBSS);
5) long-term trypsin-incubation (LTT) for 8 hrs (LTT 8 hr); and
6) LTT for 16 hrs (LTT 16 hr).

For negative controls, human peripheral mononuclear cell fractions were used.

For conditions 4), 5) and 6), approximately $1 \times 10^5$ to $5 \times 10^5$ cells were suspended in 5 ml trypsin solution, and incubated. Cells from stress conditions 1) through 3) were collected by a 5-min trypsin incubation, and cells from stress conditions 4) to 6) were transferred directly to tubes.

Large numbers of dead cells resulting from stress conditions were disrupted by vortexing. Specifically, 5 ml medium containing a maximum of 500,000 cells was transferred into a 15-ml Falcon tube, followed by 3 min of vortexing at 1800-2200 rpm/min using a vortex mixer (IKA Works, Inc.). Centrifugation was performed at 2000 rpm for 15 min, so as to remove the supernatant. Collection efficiency of live cells after vortexing ranged from approximately 70% to 80%.

2. MC Culture

In the Examples, cells were subjected to suspension culture in methylcellulose-containing medium. Culture in methylcellulose-containing medium is referred to as "MC culture." MC culture is as described in Nakahata, T. et al., Blood 60, 352-361 (1982).

Culture dishes were first coated with poly-HEMA (poly (2-hydroxyethyl methacrylate)) to avoid attachment of cells to the bottom of the dish. In brief, 600 mg of poly-HEMA (SIGMA) was dissolved in 40 ml of 95% EtOH by stirring at 37° C., added to the dish (e.g., 40 μl/well for 96-well culture dish and 200 μl/well for 12-well culture dish), and the dish was air-dried overnight.

MC (MethoCult H4100, StemCell Technologies) was suspended in 20% FBS+α-MEM to a final concentration of 2%. The cell concentration in the semisolid MC medium was adjusted to be $8 \times 10^3$ cells/ml at this concentration, so that the cell-to-cell distance was sufficiently large to minimize cell aggregation. Cells and MC medium were mixed thoroughly by gentle pipetting, and the mixture was transferred to a polyHEMA-coated dish. To prevent drying, a volume equal to one tenth of the initial MC culture of 10% FBS in α-MEM was gently added to the dish every 3 days.

Cell clusters (referred to as Muse cell-derived embryoid body-like cell cluster=M-clusters since cell clusters were clusters from the pluripotent stem cells, Muse cells, of the present invention) were cloned on day 7. 0.01 M PBS was added to the medium, the cells centrifuged at 2000 rpm for 20 min, and the supernatant discarded. This procedure was repeated three times to wash the cells. The collected cell pellet was finally suspended in 10 μl of 0.01 M PBS containing Trypan Blue, applied to a glass slide, and the entire area was automatically imaged using phase contrast microscopy. Only multicellular clusters larger than 25 μm that were negative for Trypan Blue and had an appearance similar to hES cells were counted as M-clusters. The frequency of M-cluster formation was calculated as the number of M-clusters divided by the number of all live cells (all the Trypan Blue-negative cells). Since determination of the precise number of cells in each M-cluster was difficult, each aggregate was counted as one cell, irrespective of its size.

For making cell clusters from hES cells, they were carefully isolated from feeder cells so as not to include feeder cells, transferred to MC culture as described above, and imaged by phase contrast microscopy on day 3 of culture.

3. Single-Cell Suspension Culture

A 96-well dish was coated with polyHEMA as described above. Following a limiting dilution of cells with 10% FBS in α-MEM, single cells were plated into each well. After plating, the actual number of cells deposited in each well was determined by visual inspection using a phase contrast microscope. Empty wells or wells with more than one cell were marked and excluded from the analysis. The calculation of M-cluster formation was performed on day 10 of culture. The frequency of M-cluster formation was calculated from 3 experiments for each strain with a minimum of 250 wells per experiment.

4. Alkaline Phosphatase Staining

M-clusters from H-fibroblast fractions and H-MSC fractions were washed several times with a sufficient volume of saline. Staining was performed using the Leukocyte Alkaline Phosphatase kit (Sigma).

5. In Vitro Differentiation of M-Cluster

After 7 to 10 days of MC culture or single-cell suspension culture, single M-clusters from H-fibroblast fractions and H-MSC fractions were picked up with a glass micropipette and transferred onto a gelatin-coated culture dish or cover glass. After another 7 days of incubation, cells were dispersed from cell clusters. Cells were subjected to immunohistochemical and RT-PCR analyses to determine the presence or the absence of differentiation of the cells.

6. Immunohistochemistry

Cells were fixed with 4% paraformaldehyde in 0.01 M PBS. Muse-enriched cell fractions and M-clusters both from H-fibroblasts and H-MSC fractions were collected by centrifugation, embedded in OCT compound, and 8 μm thick cryo-sections were cut. Cell clusters were fixed on gelatin-coated cover glasses and then subjected to immunohistochemical analysis.

The following primary antibodies against: Nanog (1:500, Chemicon), Oct3/4 (1:800, kindly provided by Dr. H. Hamada, Osaka University, Japan), Sox2 (1:1000, Abcam), PAR4 (1:100, Santa Cruz), SSEA-3 (1:20, DSHB), smooth muscle actin (1:100, Lab Vision), neurofilament M (1:200, Chemicon), α-fetoprotein (1:100, DAKO), mouse Numblike (1:500, kindly provided by Dr. Yuh-Nung Jan, University of California San Francisco) and type 1 collagen (1:20, Southern Biotech) were sued. Alexa 488- or Alexa 568-conjugated anti-rabbit IgG, anti-mouse IgG or anti-mouse IgM antibodies (Molecular Probes, Carlsbad, Calif.) were used as secondary antibodies for immunohistochemical analysis. ここは抗体の種類が増えるのでは？

7. Determination of Karyotypes

Karyotypes of cells clonally expanded from M-clusters (obtained through repetition (1 to 3 times) of a cycle of collecting single cells from M-clusters and then causing cells to form cell clusters again) both from H-fibroblast fractions and H-MSC fractions were determined by quinacrine-Hoechst staining.

8. Injection of Cells into the Testes of Immunodeficient Mice

Naive cell fractions and Muse-enriched cell fractions and M-clusters both from H-fibroblast fractions and H-MSC fractions were used. Muse-enriched cell fractions were prepared by adding serum to the cells after LTT and followed by three washes with 0.01 M PBS. M-clusters were collected from MC cultures and also washed three times with PBS. $1 \times 10^5$ cells were suspended in PBS and injected using glass microtubes into the testes of NOG mice (Registered trademark, mouse NOD/Shi-scid, IL-2RγKO Jic, 8 weeks old, International Council for Laboratory Animal Science (ICLAS) Monitoring Center Japan). The average volume of the cells in M-clusters was measured using the 3D-graphic analysis software provided with the laser confocal microscope (50 M-clusters were measured and the total volumes of the clusters were divided by the number of nuclei), which resulted in $1.5 \times 10^5$ cells per 1 μl volume of collected M-cluster pellet. Each testis of a NOG mouse was then injected with the volume corresponding to $1 \times 10^5$ cells, and the mice were subjected to the experiment for analysis 6 months after the injection.

As controls, $1 \times 10^6$ mouse ES cells (for positive control, n=3) and mitomycin C-treated MEF cells (mouse embryonic feeder cells for negative control, n=3) were injected into SCID mice testes, and the mice were subjected to the experiment 8 weeks after the injection.

9. High-Resolution Analysis of Cells by Optical Microscope

Muse cells and M-clusters from H-fibroblast fractions and H-MSC fractions were observed using a stable high-resolution optical microscope for cell types such as human MSC, fibroblasts, and neuronal cells.

10. Ultrathin Sectioning for Electron Microscopy

M-clusters, SSEA-3(+) and SSEA-3(−) cells both from H-fibroblast fractions and H-MSC fractions as well as cell clusters formed by hES cells were centrifuged. The pellets were fixed with 2.5% glutaraldehyde in 100 mM phosphate buffer (pH 7.2) for 30 min. The fixed samples were embedded in 1% agar. The embedded samples were trimmed to 1 $mm^3$, washed with PBS, and stained with 2% $OsO_4$ in 100 mM phosphate buffer (pH 7.2) for 10 minutes at 4° C. The samples were washed with distilled water and then stained with 5 drops of 2% uranyl acetate (UA) for 20 min at 4° C. After washing with distilled water, the stained samples were incrementally dehydrated with 50%, 70% and 90% ethanol for 10 min each at 4° C., and then completely dehydrated with three exchanges of 100% ethanol. The samples were incubated with propylene oxide for 5 min (for exchange) and embedded in 50% epoxy resin in propylene oxide for 60 min, followed by embedding in 100% epoxy resin and hardening at 60° C. overnight. Ultrathin sections were cut with a thickness of 70-80 nm and observed in a 100 kV electron microscope using a CCD camera.

11. Growth Rate of M-Clusters

To calculate the population doubling time for cells in the M-clusters from both H-fibroblast fractions and H-MSC fractions, the clusters were each transferred to 96-well plates and treated with trypsin for 15 min followed by pipetting with a glass micropipette. The number of cells in each well was counted. At least 20-30 M-clusters were analyzed at predetermined time points (day 1, 3, 5, 7, 9, 10, 11, 12, 13 and 14).

12. RT-PCR

Naive cell fractions (about 10,000 cells per well of a 24-well plate) and cells in vitro differentiated from single M-clusters (1 to 3 cycles) both from H-fibroblast fractions and H-MSC fractions (about 10,000 cells per well of a 24-well plate) were used. Total RNA was extracted and purified using NucleoSpin RNA XS (Macherey-Nagel). First-strand cDNA was generated using the SuperScript VILO cDNA Synthesis Kit (Invitrogen). The PCR reactions were performed using appropriate primers designed and Ex Taq DNA polymerase (TaKaRa Bio Inc.). The used primers were as follows.

Total RNA was extracted and purified using NucleoSpin RNA XS (Macherey-Nagel). First-strand cDNA was generated using the SuperScript VILO cDNA Synthesis Kit (Invitrogen). The PCR reactions were performed using appropriate primers designed and Ex Taq DNA polymerase (TaKaRa Bio Inc.). As positive controls, human fetal liver (Clonetech) was used for α-fetoprotein primers and human complete embryos were used for others.

13. Quantitative-PCR (Q-PCR)

Total RNA was collected from naive cell fractions, Muse-enriched cell fractions and M-clusters from H-fibroblast-1, H-fibroblast-2, H-MSC-1, and H-MSC-2 using the RNeasy Mini Kit (Qiagen GmbH) and cDNA was synthesized using the $RT^2$ First Strand Kit (SA Biosciences). Customized primers were purchased from SA Biosciences and the DNA was amplified by quantitative PCR with the 7300 real-time PCR system (Applied Biosystems). The data were processed using the $\Delta\Delta C_T$ method (Livak K J et al., Methods 25: 402-408, 2001).

14. DNA Microarray Analysis

Naive cell fractions, Muse-enriched cell fractions and M-clusters from H-fibroblast-1, H-fibroblast-2, H-MSC-1, and H-MSC-2, as well as the mixture of human peripheral mononuclear cells obtained from 4 healthy volunteers were used. Total RNA was collected using the RNeasy Mini Kit (Qiagen) and analyzed by DNA microarray (TaKaRa Bio Inc.). Array signals were processed and normalized using the Affymetrix Expression Console V1.1 software. Pathway Studio 6.0 (Ariadne Genomics) was used to assign the differentially expressed genes to functional categories in the Gene Ontology. Hierarchical clustering was performed at a Euclidean distance based on differentially expressed genes with average linkage clustering by MeV4 (Saeed A I et al., Biotechniques 34(2): 374-378, 2003).

15. Detection of Telomerase Activity

Muse-enriched cell fractions and M-clusters from H-fibroblast fractions and H-MSC fractions, and Hela cells were used. Telomerase activity was detected using the TRAPEZE XL telomerase detection kit (Millipore) and Ex Taq polymerase (TaKaRa Bio Inc.). Fluorescence intensity was measured with a micro plate reader (Tecan).

16. Bisulfite Sequencing

Genomic DNA (1 μg) from naive cell fractions, Muse-enriched cell fractions, or M-clusters from H-fibroblast fractions and H-MSC fractions was treated using CpGenome DNA modification kit (Chemicon). DNA was purified using a QIAquick column (Qiagen). The promoter regions of human Oct3/4 and Nanog genes were amplified by PCR and then the PCR products were subcloned into pCR2.1-TOPO. Up to 10 clones of each sample were verified by sequencing using M13 universal primers, so that the methylation in each promoter region was detected. Primers described in Shimazaki T et al., EMBO J, 12:4489-4498, 1993 were used for PCR amplification.

17. M-Cluster Formation from Human Bone Marrow Aspirates

Three human bone marrow aspirates from healthy donors were purchased from ALLCELLS. Mononuclear cell fractions were collected using the Lymphoprep Tube (Axis-Shield PoC AS) and subjected to MC culture directly (without trypsin incubation) or after 8 hr-LTT as described above. M-clusters were counted on day 7.

18. MACS Sorting

Figure 4:
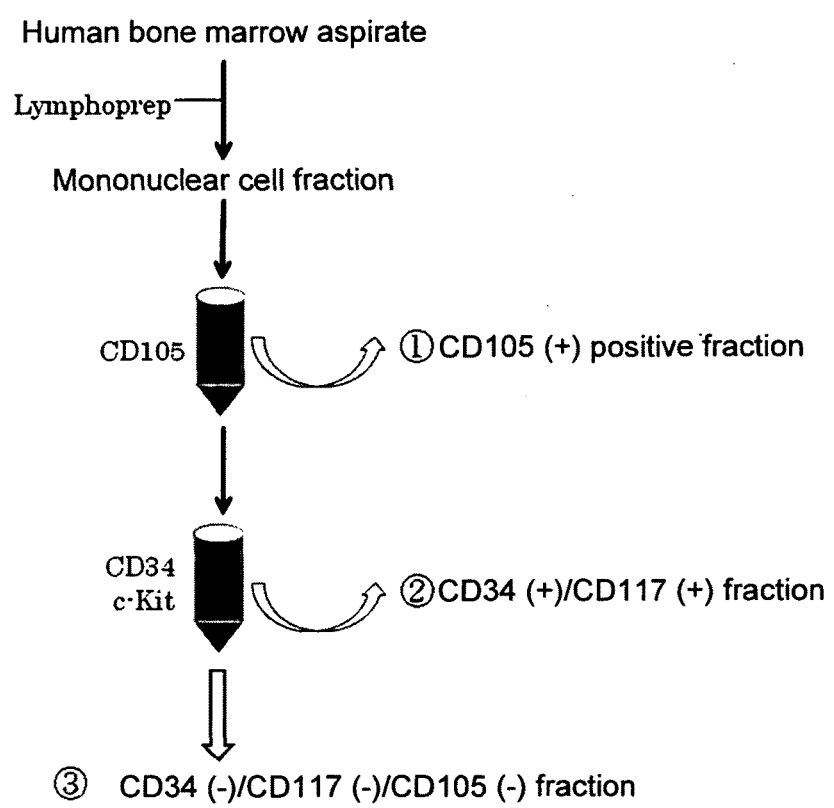
FIG. 4 shows protocols for MACS sorting.

Mononuclear cell fractions from human bone marrow aspirates of three healthy donors (ALLCELLS) were first reacted with microbeads-conjugated anti-CD105 antibody and sorted using MS Columns (Miltenyi Biotech). CD105 (+) cells were collected as Fraction 1 (mesenchymal cell population). CD105(−) cells were incubated with a mixture of anti-CD34 and anti-CD117 antibodies conjugated to microbeads and sorted again to obtain CD34(+)/CD117(+) cells (Fraction 2 corresponding to a hematopoietic stem cell population) and CD105(−)/CD34(−)/CD117(−) cells (Fraction 3) (FIG. 4). The thus collected samples were subjected to 8 hr-LTT and then the formation of M-clusters was determined.

19. Immunohistochemistry

Mice testes were fixed with 4% paraformaldehyde in 0.02 M PBS, and a cryostat was used to cut 10 μm-thick sections. Samples were washed with 0.02 M PBS, incubated with 20% BlockAce (Yukijirushi)-containing buffer for blocking and then incubated with primary antibodies for immunohistochemical analysis. The primary antibodies used were: smooth muscle actin antibody (1:200, Lab Vision), anti-MAP-2 antibody (1:200, Biogenesis), and anti-α-fetoprotein antibody (1:10, DAKO).

Anti-rabbit IgG antibodies conjugated with Alexa488 or Alexa568 and anti-mouse IgG antibodies conjugated with Alexa568 used as secondary antibodies were incubated in the presence of DAPI. Samples were inspected with a C1si Nikon confocal microscope system (Nikon Corporation).

20. Flow Cytometry and Cell Sorting

Cells were incubated with phycoerythrin-labeled antibodies against CD11c, CD29, CD34, CD44, CD45, CD49f, CD54, CD71, CD90, CD105, CD166, CD271 or vWF (Becton Dickinson) or with anti-SSEA-3 antibodies (Millipore). In the case of labeling with the anti-SSEA-3 antibody, cells were further incubated with FITC-conjugated anti-rat IgM antibodies. Calcium and magnesium-free 0.02 M PBS supplemented with 2 mM EDTA and 0.5% bovine serum albumin was used as the FACS antibody diluents. Data were acquired and analyzed using FACSCalibur (Becton Dickinson) and the CellQuest software or using FACSAria and the DIA software. For cell sorting, cells were incubated with anti-SSEA-3 antibody in the FACS antibody diluents and sorted by FACSAria (Becton Dickinson) using a low stream speed and in the 4-way purity sorting mode.

21. Statistical Analysis

Data are expressed with average±SEM. Data were compared via paired comparison according to the Bonferroni method using ANOVA.

Results

A. Stress Conditions for H-Fibroblast Fractions and H-MSC Fractions

Examples of the results of exposure of H-fibroblast fractions and H-MSC fractions to stress conditions are shown in Table 1.

After exposing the cells to stress conditions and vortexing, Trypan Blue staining was used to count the number of live cells, from which the survival rate was calculated. The surviving cells were collected and grown in MC culture for 7 days. Stress conditions 2) resulted in a large number of dead cells and low efficiency for collecting surviving cells. It was therefore not possible to accurately determine the number of formed M-clusters, and the number of M-clusters for stress conditions 2) is thus denoted as ND (not determined) in Table 1.

Among the 6 stress conditions tested, the 16 hr-trypsin incubation was most effective for H-fibroblast fractions and the 8 hr-trypsin incubation for H-MSC fractions. When this experiment was repeated using two strains of H-fibroblast fractions and four strains of H-MSC fractions, the same trend was observed. M-clusters could not be recognized in the negative control using human peripheral mononuclear cells. Examples of typical observed values are shown in Table 1.

TABLE 1

Survival rates after exposure to stress conditions and M-cluster formation in MC culture in H-fibroblasts, H-MSCs and human peripheral mononuclear cells.

| | | Start cell number | Survival after stress (%) | Cell cluster formation in MC culture (>25 μm) (% to survived cells) |
|---|---|---|---|---|
| | H-fibroblast-1 | | | |
| 1 | Non-serum | 30,000 | 75 | 7 |
| 2 | HBSS | 2,000,000 | 6 | ND |
| 3 | 10% FBS + LowO2 | 30,000 | 99 | 8 |
| 4 | Tryp 3 × 1 hr | 2,000,000 | 0.3 | 6 |
| 5 | LTT 8 hr | 2,000,000 | 1 | 15 |
| 6 | LTT 16 hr | 500,000 | 5 | 20 |
| | H-MSC-1 | | | |
| 1 | Non-serum | 30,000 | 44 | 5 |
| 2 | HBSS | 2,000,000 | 2 | ND |
| 3 | 10% FBS + LowO2 | 300,000 | 99 | 8 |
| 4 | Tryp 3 × 1 hr | 380,000 | 0.9 | 9 |
| 5 | LTT 8 hr | 380,000 | 10 | 21 |
| 6 | LTT 16 hr | 500,000 | 3 | 14 |
| | Human peripheral mononuclear cells | | | |
| 5 | LTT 8 hr | 300,000 | 2 | 0 |
| 6 | LTT 16 hr | 300,000 | 1 | 0 |

ND (not determined): M-clusters could not be calculated accurately, because the final fraction contained a large number of dead cells and efficiency for collecting surviving cells was low.

Figure 5:
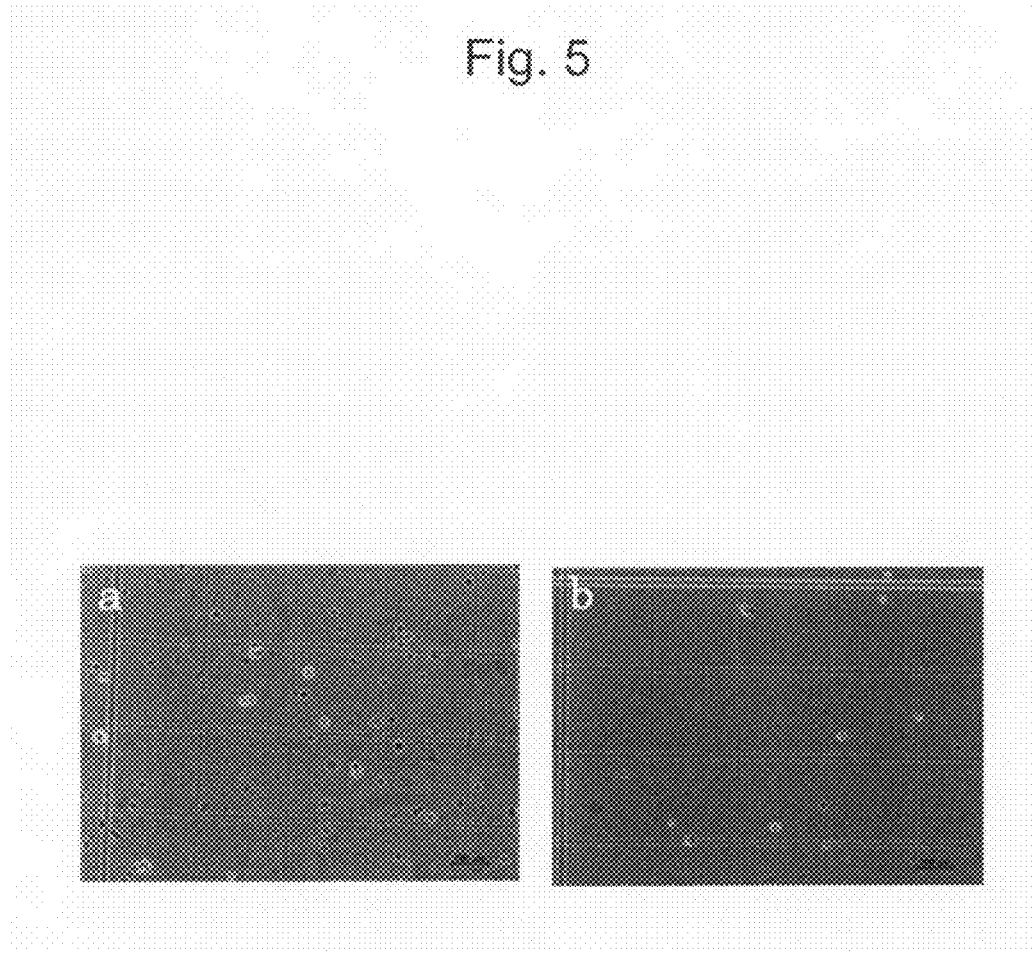
FIG. 5 shows photos (stained images) showing the removal of dead cells when human fibroblast (H-fibroblast) fractions were subjected to 16-hr-long trypsin incubation (FIG. 5a), 3 minutes of vortexing at 1800 rpm-2200 rpm/minute (FIG. 5b), and then trypan blue staining.

Among the 6 stress conditions tested, the 16 hr-trypsin incubation (H-fibroblast fractions) and the 8 hr-trypsin incubation (H-MSC fractions) were the most effective for the formation of M-clusters. A series of procedures including 16 hr- or 8 hr-trypsin incubation followed by vortexing at 1800-2200 rpm/min for 3 min and centrifugation at 2000 rpm for 15 min was termed "Long-Term Trypsin incubation (LTT)" and used for the enrichment of Muse cells. Collection efficiency of live cells after vortexing ranged from approximately 70% to 80% (FIG. 5).

B. Criteria for M-Clusters

Figure 6:
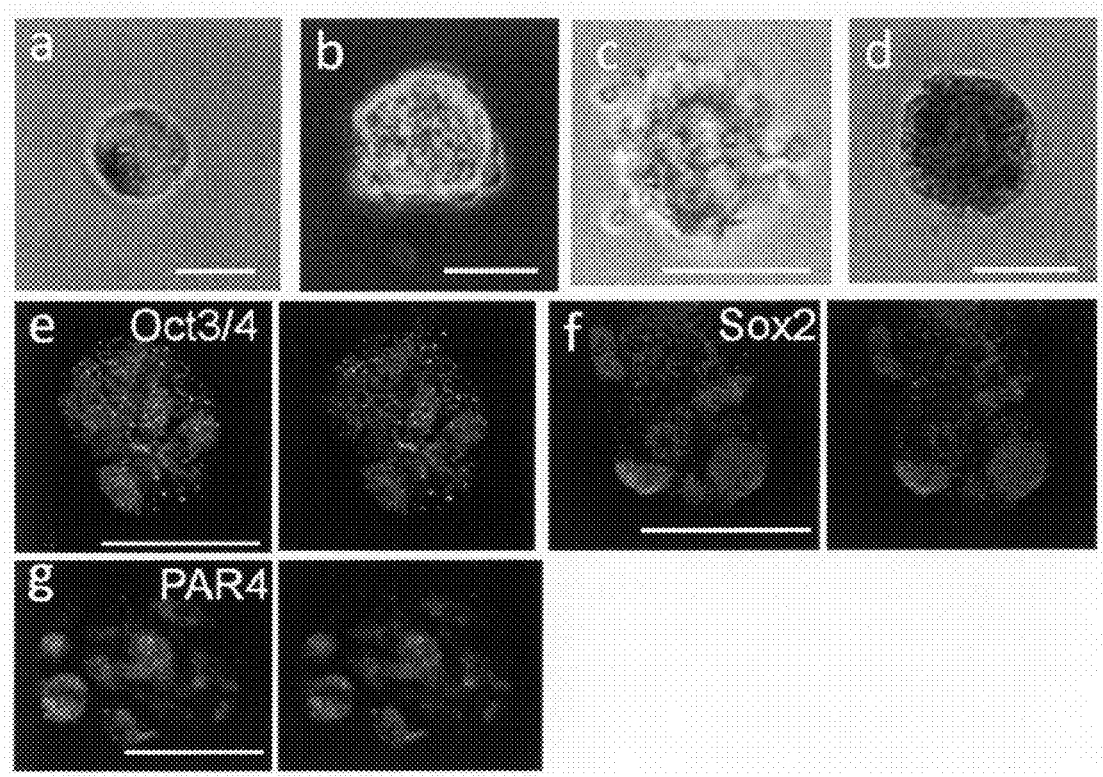
FIG. 6 shows photos of various cells.

In the Examples, criteria for M-clusters were established. The average diameter of single cells in Muse-enriched cell fractions both from H-fibroblast fractions and H-MSC fractions was 10-13 μm (FIG. 6a). When these cells were transferred to MC culture, the cells started to divide. The size of the individual cells became smaller after cell division, and the gradually forming multicellular clusters comprised cells of 8-10 μm in diameter (FIGS. 7e and 7f). The size and appearance of the cells were similar to those of human ES cells subjected to MC culture (FIGS. 6b and 6c). On day 7, most of the multicellular clusters became larger than 25 μm, having a diameter of 100-150 μm. The cell clusters had an appearance very similar to cell clusters formed by ES cells. Cell clusters larger than 25 μm were collected using (D25 μm filters (FIG. 6b) and then analyzed (up to 100 M-clusters each from H-fibroblast fractions and H-MSC fractions) by immunocytochemistry. Most of M-clusters were positive for the pluripotency markers Nanog, Oct3/4, Sox2, PAR4 and SSEA-3 and also positive for alkaline phosphatase staining (FIGS. 6e-g). Pluripotency markers could be detected or not detected in cell clusters smaller than 25 μm, but their localization was sometimes atypical and the appearance of the cells was more similar to that of cells in Muse-enriched cell fractions.

Based on these findings, only multicellular clusters larger than 25 μm in diameter were counted as M-clusters.

C. Analysis of Cell Clusters Generated from Human Mesenchymal Cell Fractions

It is well known that dormant tissue stem cells are activated when the tissue is exposed to stress, burdens or damages. In the Examples, H-MSC fractions and H-fibroblast fractions were exposed to stress conditions by various methods. Specifically, the stress conditions tested were: treatment with non-serum medium; treatment with Hanks' Balanced Salt Solution (HBSS); treatment with low $O_2$ concentration; and long-term trypsin incubation (LTT) for a total of 3, 8, or 16 hours. Cells that had survived the stress conditions were collected and then suspended in methylcellulose (MC)-containing medium (referred to as MC culture), followed by 7 days of MC culture at a density of 8000 cells/mL (FIG. 7-1d). Each condition gave rise to cell clusters with sizes up to 150 μm in diameter (FIGS. 7-1e and f). FIG. 7-1c shows MC culture of H-fibroblast-1 fractions on day 0, FIG. 7-1d shows MC culture of the same on day 7. Formation of the highest number of cell clusters were observed in H-fibroblast fractions subjected to 16-hr LTT and in H-MSC fractions subjected to 8-hr LTT. FIGS. 7-1e and f show cell clusters (M-clusters) formed from H-fibroblast-1 fractions. FIG. 7-1e shows MC culture on day 7 and FIG. 7-1f shows suspension culture of single cells on day 10. Cell clusters were sorted using filters with different pore-sizes according to their size, so that immunocytochemical analysis was performed. The cell clusters with a diameter larger than 25 μm contained cells positive for the pluripotent stem cell markers Nanog, Oct3/4, SSEA-3, PAR-4 and Sox2 (FIGS. 7-2g-l) and positive for alkaline phosphatase staining (FIGS. 7-3 m-o). Electron microscopy revealed that cell clusters generated from H-fibroblast fractions and H-MSC fractions had the same characteristics as clusters formed by ES cells. The cells showed a similar nucleus/cytoplasm ratio, fewer organelles, and presence one or two big nucleoli in the nucleus (FIGS. 7-4 p-r).

Cells capable of forming cell clusters positive for pluripotency markers and alkaline phosphatase staining by suspension culture were found from the H-MSC fractions and H-fibroblast fractions of a living body. The present inventors named these cells "Muse cells" (multilineage differentiating stress enduring cells). Cell populations formed from H-fibroblast fractions subjected to 16 hr-LTT and H-MSC fractions subjected to 8 hr-LTT are referred to as "Muse-enriched cell fractions (Muse-enriched cell populations)." Single cells obtained from the cell populations were subjected to suspension culture. Formation of M-cluster was observed in 9%-10% of Muse-enriched cell fractions. This indicates that the muse-enriched cell fractions contained about 9%-10% Muse cells.

Figures 1, 8:
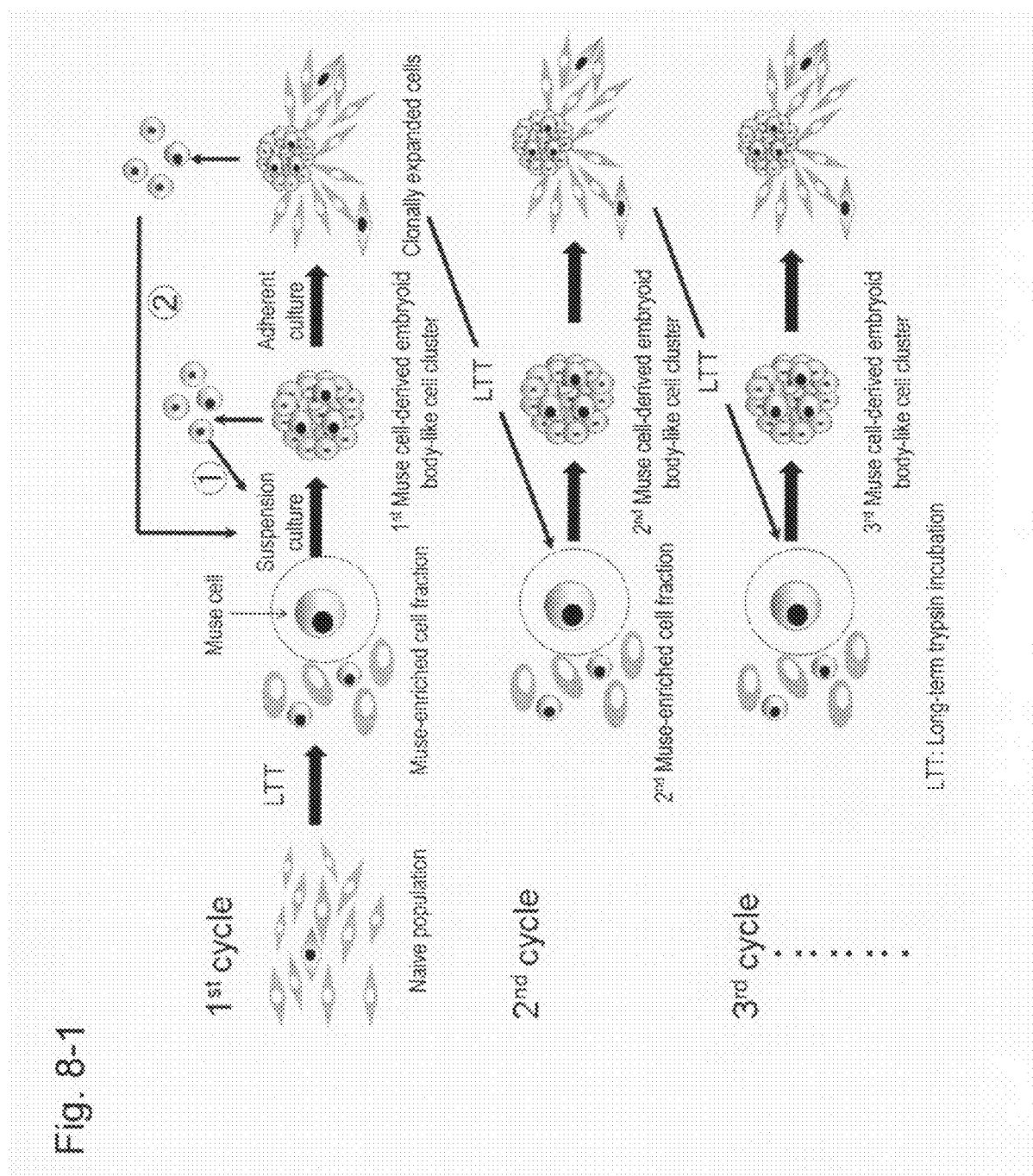
Figures 2, 8:
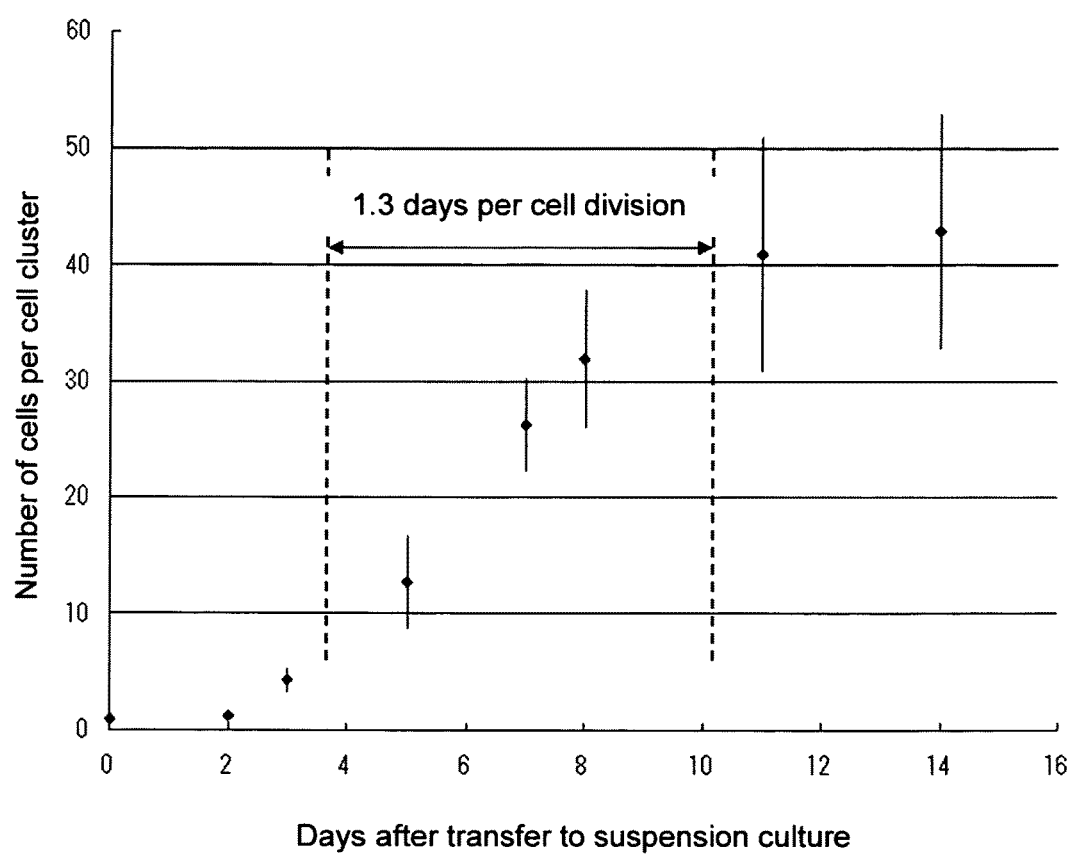
Figures 3, 8:
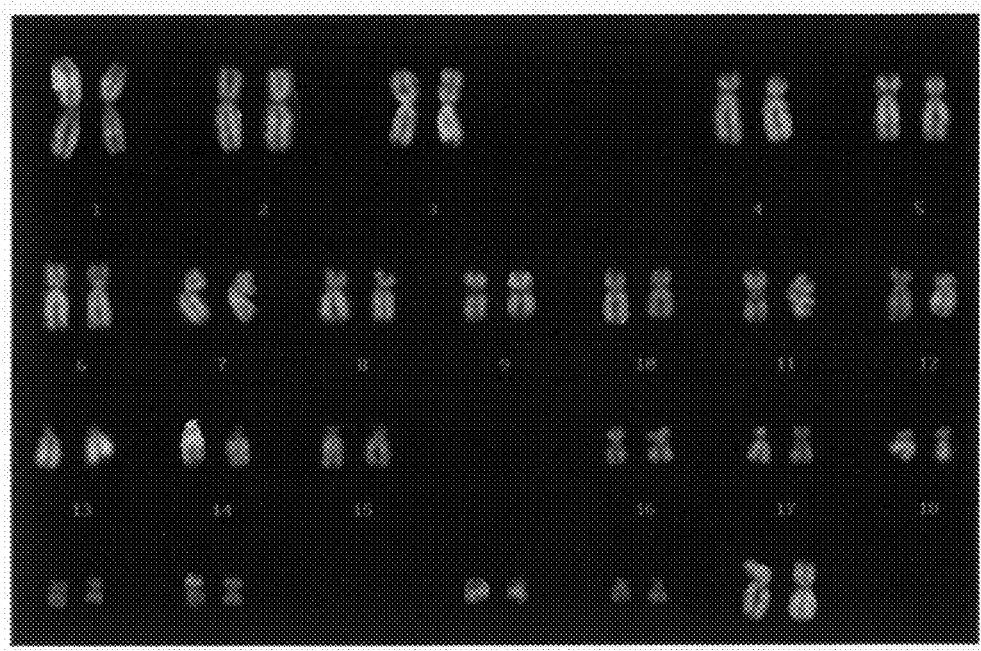

The growth of Muse cells isolated was examined. Cells began to divide after 1-2 days in MC culture and kept dividing at a rate of approximately 1.3 days/cell division until day 10 (FIG. 8-2). However, cell growth gradually slowed down by days 11-12 and seized by around day 14, with cell clusters that reached a maximum size of 150 µm in diameter. When the formed M-clusters were directly dissociated into single cells by a 5-min trypsin incubation and returned to single-cell suspension culture, the cells remained alive but divided very slowly (5-7 days/cell division) or sometimes not at all (FIG. 8-1 (1)). Thus, once their proliferation has been limited (or once their growth rate has been lowered), Muse cells do not re-accelerate their proliferation as long as they are maintained in suspension culture. However, transfer of single M-clusters to adherent culture reinitiated cell proliferation. After 5-7 days, when relatively small-scale cell populations, at a stage of 3,000 to 5,000 cells, were dissociated by 5 minutes of trypsin incubation and subjected to MC culture, 40% of the cells formed new cell clusters (FIG. 8-1 (2)). When the clonally expanded cell populations were allowed to reach a scale of about 5–10×10$^4$ cells and then subjected to LTT to produce Muse cells ($2^{nd}$ cycle) again, nearly 10% of these cells formed M-clusters (FIG. 8-1). This culture cycle was repeated five times, consisting of LTT-suspension culture-adherent culture, so that every cell generation showed the similar behavior and frequency of M-cluster formation. The $5^{th}$ generation M-clusters (at the $5^{th}$ cycle) were still positive for pluripotency markers and alkaline phosphatase staining.

To confirm that these phenomena were not due to abnormal cells that had undergone mutation or the like, karyotypes of cells were determined. The karyotypes of most cells clonally expanded from M-clusters were normal and did not show detectable chromosomal abnormalities (FIG. 8-3). These results demonstrate that the phenomena resulted from normal cells.

These results demonstrate the capacity of Muse cells for self-renewal and clonal expansion. Muse cells grow through the series of cycle, "Muse cells—M-cluster—clonal expansion." It might be possible to obtain large numbers of Muse cells from mesenchymal cell populations.

D. Differentiation of M-Cluster into the Three Germ Layers

To confirm differentiation ability, single M-clusters were transferred onto gelatin-coated dishes and analyzed for differentiation. On day 7, α-smooth muscle actin (mesodermal marker), desmin (mesodermal marker), neurofilament-M (ectodermal marker), α-fetoprotein (endodermal marker), or cytokeratin-7 (endodermal marker) were detected (FIG. 9-1 a-c). RT-PCR confirmed that $1^{st}$ and $3^{rd}$ generation M-clusters ($1^{st}$ to $3^{rd}$ cycles) expressed α-fetoprotein and GATA6 (endodermal marker), microtubule-associated protein-2 (MAP-2) (ectodermal marker), and Nkx2.5 (mesodermal marker) while no differentiation was observed in naive H-fibroblasts or MSC populations cultured on gelatin-coated dishes (FIG. 9-2).

Muse-enriched cell fractions, M-clusters, or ES cells were injected into the testes of immunodeficient mice, so as to confirm teratoma formation (FIG. 9-3e). Histological examination of the testes revealed that within 8 weeks all mice injected with ES cells developed teratomas. However, remaining transplanted human cells and differentiation into various cell species were detected in the testes of 10 out of 13 mice injected with Muse-enriched cell fractions and 10 out of 11 mice injected with M-clusters as shown in FIG. 9-3e. Teratoma formation was never detected until at least 6 months in groups to which Muse cell-enriched cell fractions or M-clusters had been transplanted. Transplanted human cells were labeled with an anti-human mitochondria antibody. These cells were simultaneously confirmed to express ectodermal-(neurofilament), endodermal-(α-fetoprotein) and mesodermal-(smooth muscle actin) markers (FIG. 9-3f-i).

These data suggest that H-fibroblast fraction-, and H-MSC fraction-derived Muse cells, and M-clusters are capable of differentiating into the 3 germ layers both in vitro and in vivo.

E. Quantitative PCR

Expression of markers relating to pluripotency and differentiation state is shown in FIG. 10. The expression levels of Nanog were not so high in Muse-enriched cell fractions and cell clusters, compared with naive cells. Some pluripotent stem cells did not express Nanog at high levels (Chou Y F et al., Cell 135, 449-461 (2008)); Bui H T et al., Development. 135(23):3935-3945 (2008)). Similar to Nanog, Oct-4 was expressed at a low level in reprogramming somatic cells compared with mouse ES cells, as determined by Q-PCR (Bui H T et al., Development. 135 (23): 3935-3945 (2008)). Therefore, the expression levels of Nanog and other pluripotency markers are not so important for pluripotency.

F. Gene Expression in Muse-Enriched Cell Fractions and M-Clusters

It was found by using quantitative PCR that some markers for pluripotency and an undifferentiated cell state were up-regulated to various degrees in both Muse-enriched cell fractions and M-clusters. Muse-enriched cell fractions merely contained 9%-10% Muse cells as described above. However, compared to naive cell fractions, the genes showed tendency of higher-degree or moderate up-regulation in Muse-enriched cell fractions: Rex1 (ZFP42), Sox2, KLF-4, c-Myc, DPPA2 (developmental pluripotency associated 2), ERAS, GRB7 (growth factor receptor-bound protein 7), SPAG9 (sperm associated antigen 9), and TDGF1 (teratocarcinoma-derived growth factor 1). The genes showed tendency of higher degree or moderate up-regulation in M-clusters were: DAZL (azoospermia-like), DDX4 (VASA), DPPA4 (developmental pluripotency associated 4), Stella, Hoxb1, PRDM1, and SPRY2 (sprouty homolog 2) (FIG. 10a) compared with naive cells.

Figure 10A:
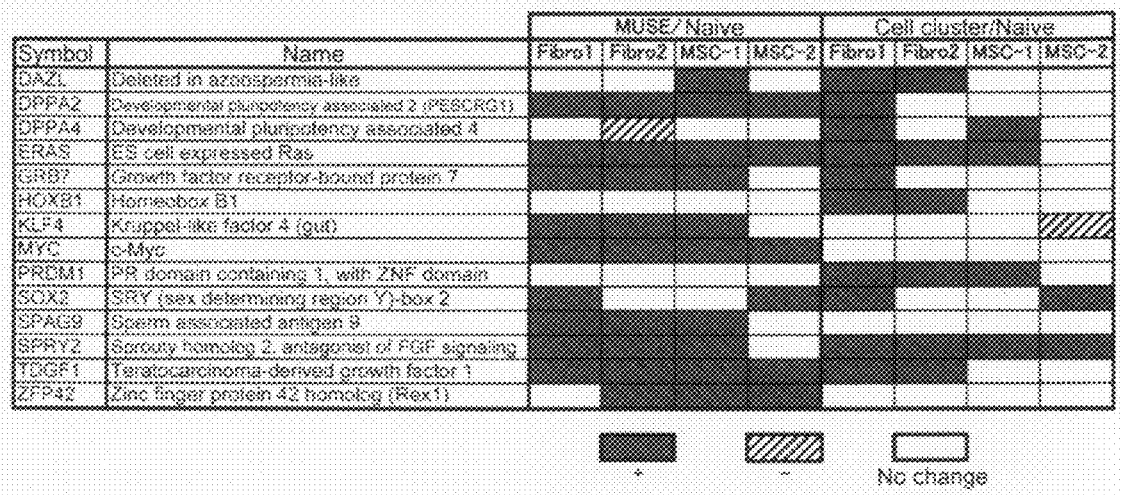
FIG. 10*a* shows the results of quantitative PCR for factors involved in pluripotency and undifferentiated cell states of H-fibroblasts (Fibro-1 and Fibro-2) and H-MSCs (MSC-1 and MSC-2) (No. 2). Each pattern given in a column in FIG. 10*a* indicates the result of comparing the gene expression level in Muse-enriched cell fractions or M-clusters (day 7) with the same in naive cell fractions. A white pattern indicates that the ratio of the gene expression level in the Muse-enriched cell fractions or the M-clusters to the same in naive cell fractions is greater than ⅓ (1:3) but is lower than 3 (3:1). A gray pattern indicates that the ratio of the gene expression level in the Muse-enriched cell fractions or the M-clusters to the same in naive cell fractions is greater than 3 (3:1). A pattern of oblique lines indicates that the ratio of the gene expression level in the Muse-enriched cell fractions or the M-clusters to the same in naive cell fractions is lower than ⅓ (1:3).

Overall gene expression in H-fibroblast fraction- and H-MSC fraction-derived naive cell fractions, Muse-enriched cells fractions, and M-clusters was compared with that in a human peripheral mononuclear cell fraction as a control. As a result, fluctuations in expression patterns of some genes were observed in naive cell fractions, Muse-enriched cells fractions, and M-clusters (FIG. 10a).

Muse-enriched cell fractions and M-clusters showed low telomerase activity, suggesting that telomerase activity is not strongly related to the proliferation activity of Muse cells (FIG. 10b).

G. DNA Microarray Analysis of Global Gene Expression

Figure 11:
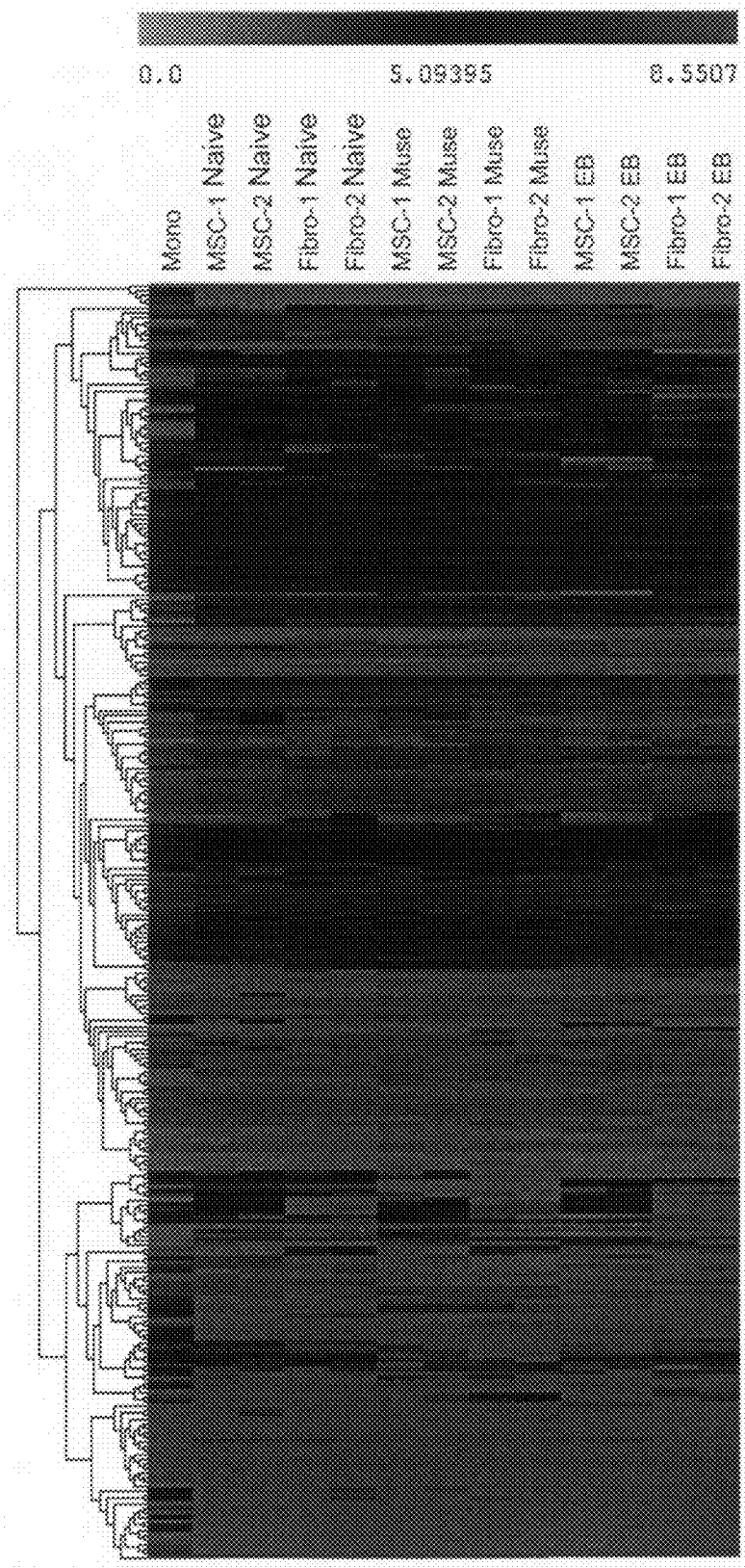
FIG. 11 shows the results of DNA microarray analysis for H-fibroblast fraction- and H-MSC fraction-derived naive cell fractions, Muse-enriched cell fractions, and M-clusters.

Pearson correlation analysis of 108 probes was performed for human peripheral blood mononuclear cells (as negative control), naive cell fractions, and the Muse-enriched cell fractions and M-clusters from H-fibroblast fractions and H-MSC fractions (FIG. 11).

Also, odorant receptors and chemokine receptors expressed were picked up by DNA microarray analysis.

H. Muse Cells Exist In Vivo

Figure 12:
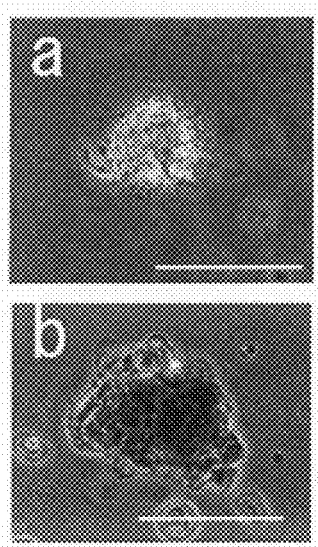
FIG. 12 shows photos showing embryoid body-like cell clusters formed by MC culture of Muse cells directly collected as SSEA-3/CD105 double positive cells from a mononuclear cell component of human bone marrow.
Figure 13:
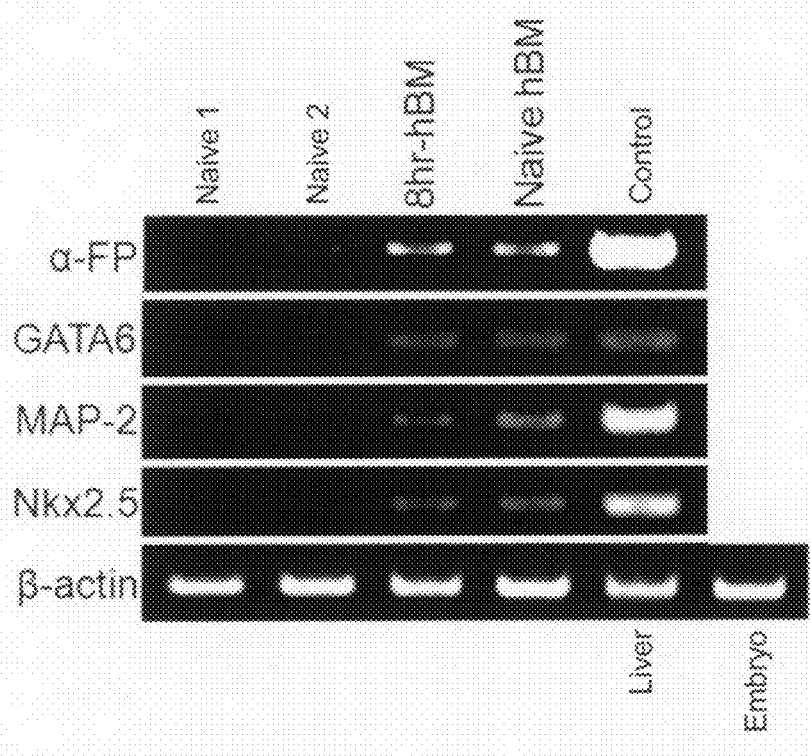
FIG. 13 shows the results of RT-PCR analysis for α-fetoprotein (α-FP), GATA6, MAP-2, and Nkx2.5 in cell populations prepared by culturing on gelatin M-clusters formed from naive H-MSC-1 fractions (naive 1), naive H-MSC-2 fractions (naive 2) (both fractions were negative controls), and human bone marrow-derived mononuclear cell fractions (8 hr-hBM) subjected to 8 hours of trypsin incubation or human bone marrow-derived mononuclear cell fractions (naive hBM) not subjected to trypsin incubation, so as to induce spontaneous differentiation thereof.

The experiments described so far were performed with stable cultured cells, which may have acquired characteristics that differ from cells in situ when they are obtained from an adult body and then cultured. Hence, a possibility that Muse cells or M-clusters are artifact products cannot be denied. Therefore, we attempted to directly obtain M-clusters from a human body; that is, human bone marrow cells without culture. The mononuclear cell fractions were isolated from human bone marrow aspirates and either cultured directly on MC (naive hBM-MC) or subjected to 8 hr-LTT prior to MC culture (8 hr-hBM-MC; the survival rate of mononuclear cells after LTT was about 3.5%). After 7 days, the cultures were tested for M-cluster formation. 8 hr-hBM-MC formed M-clusters at a frequency of about 0.3%, approximately 75 times higher than that of naive hBM-MC (about 0.004%) (FIG. 12a). The M-clusters were positive for alkaline phosphatase staining (FIG. 12b). RT-PCR of cells clonally expanded from single M-clusters both from naive hBM-MC and 8 hr-hBM-MC showed expression of α-fetoprotein, GATA6, MAP-2 and Nkx2.5 (FIG. 13). These results prove that Muse cells exist in vivo in human bone marrow, that they can be enriched by 8 hr-LTT and that they can form M-clusters. It was also confirmed that, among many cell types in bone marrow, the majority of Muse cells belong to the CD105(+) mesenchymal cell fractions.

As described above, Naive hBM-MC formed M-clusters at an extremely low frequency of about 0.004% in mononuclear cell fractions directly isolated from the human bone marrow aspirate. Since it is conceivable that culturing cells changes the composition of the cell population, cells in stable culture may have a different propensity to form M-clusters compared with naive mononuclear cells isolated from the bone marrow. To confirm this possibility, a human bone marrow aspirate was cultured to collect primary MSCs and then the cells were directly subjected to MC culture. This protocol resulted in a much higher frequency of M-cluster formation of about 0.2%. When these primary MSCs were further cultured, to the $2^{nd}$ and $5^{th}$ subculture, the frequency of M-cluster formation increased by about 0.5% and about 1.0%, respectively, with respect to naive cell fractions. Consistent with this finding, about 1.2% of naive H-fibroblast fractions and H-MSC fractions formed M-clusters. These results suggest that Muse cells have high stress tolerance and can endure in vitro culture environment such as subculture procedures. Stable subcultured cell fractions thus showed a higher frequency of M-cluster formation than mononuclear cell fractions isolated directly from the bone marrow aspirate.

Bone marrow contains many cell types of mononuclear cells including MSCs, hematopoietic lineage cells, and endothelial cells. To determine which fraction contains the Muse cells, mononuclear cell fractions were isolated from a human bone marrow aspirate and then directly subjected to MACS sorting using antibodies against CD34, CD117 (markers for hematopoietic cells) and CD105 (marker for MSCs). The fractions were then treated with 8 hr-LTT, and the cells were grown in MC culture for 7 days. Almost no M-clusters were detected in the CD34+/CD117+ fraction, but the CD34–/CD117–/CD105+ fraction contained 50 times more cell clusters than the CD34–/CD117–/CD105– fraction. This result suggests that the majority of Muse cells belong to the CD105(+) mesenchymal cell fraction.

I. MACS Sorting

The three fractions from mononuclear cells from bone marrow contained the following percentages of total cells: Fraction 1 (CD105+ fraction): 1.8%; Fraction 2 (CD34+/CD117+ fraction): 8.5%; and Fraction 3 (CD34–/CD117–/CD105– fraction): 89.7%. The frequencies of cell cluster formation in Fractions 1, 2, and 3 were 0.5%, 0% and 0.01%, respectively. The formation of cell clusters in Fraction 1 was thus about 50 times higher than that in Fraction 3.

J. FACS Sorting

As an example, FACS sorting was performed using SSEA-3 as a marker. For both H-fibroblasts and H-MSCs, SSEA-3(+) and SSEA-3(–) cells were separated by FACS sorting and subjected to single-cell suspension culture. Approximately 50%-60% of the SSEA-3(+) cells generated M-clusters, while only few M-clusters were formed from SSEA-3(–) cells.

K. Characteristic Features of Muse Cells

Figure 14:
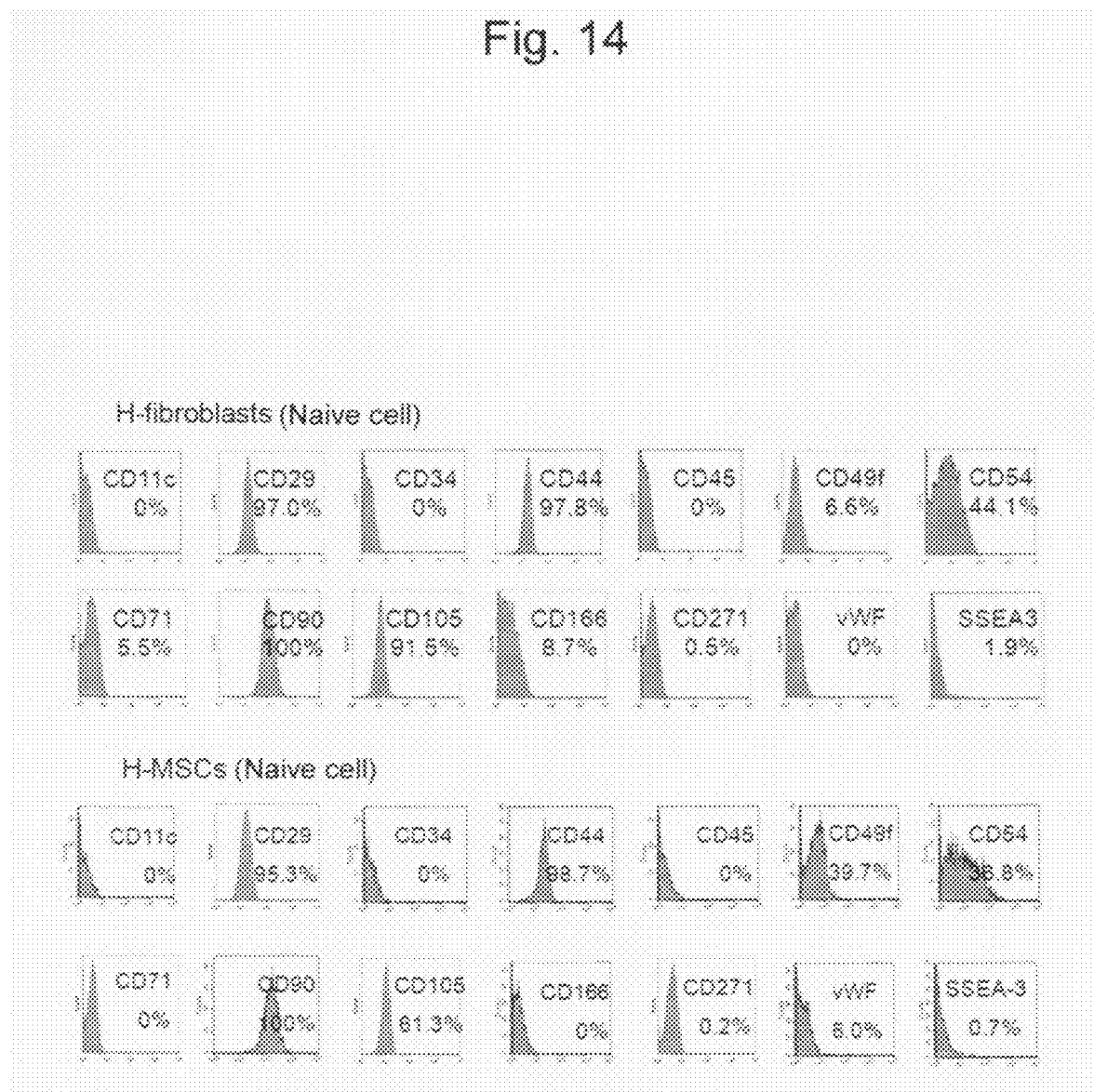
FIG. 14 shows the results of FACS analysis for H-fibroblast fractions (naive cells) and H-MSC fractions (naive cells).

FACS analysis revealed that naive H-fibroblast fractions and H-MSC fractions contained fractions positive for CD44, CD49f, CD54, CD90, and CD105 expressed in mesenchymal cells, but were negative for CD11c, CD34, CD45, CD71, CD166, CD271, and von Willebrand (vWF) factors. Muse-enriched cell fractions contained about 0.7%-1.9% SSEA-3 (+) fractions (negative for CD44 and CD54) (FIG. 14).

Figures 1, 15:
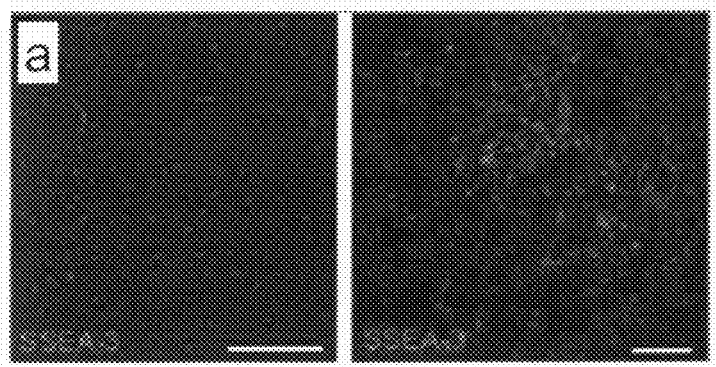
Figures 2, 15:
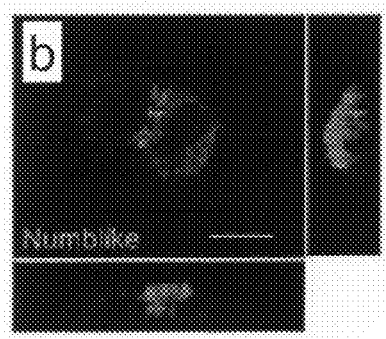
Figures 4, 15:
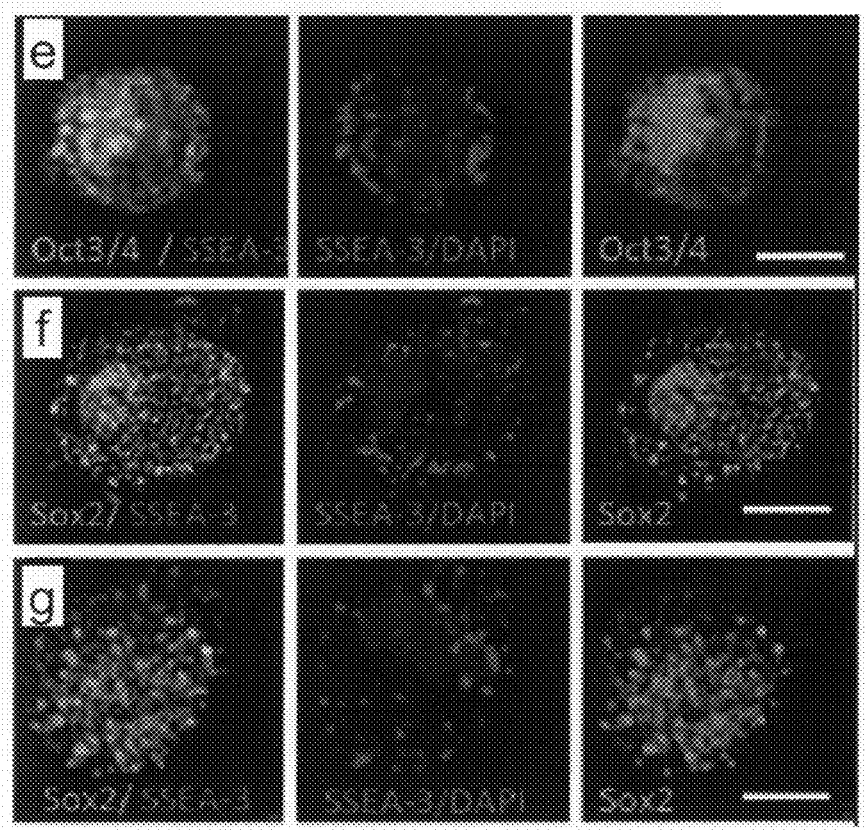

SSEA-3 is one of the known markers for pluripotency. In naive H-fibroblast fractions and H-MCS fractions, the frequency of M-cluster formation (about 1.2%) and the frequency of Muse-enriched cell fraction formation (9%-10%) were similar to the relevant percentage of SSEA-3(+) cells (naive cell fraction: about 0.7%-0.9%; and Muse-enriched cell fraction: 7%-8.3%). Such percentage of SSEA-3(+) cells may indicate a state of Muse cells. Immunohistochemical analysis revealed that the percentage (number) of SSEA-3(+) cells in naive H-fibroblast fractions and H-MSC fractions was less than 1%. SSEA-3(+) cells were then sorted from Muse-enriched cell fractions derived from H-fibroblast fractions and H-MSC fractions and then subjected to single-cell suspension culture. As a result, 50%-60% of the SSEA-3(+) cells generated M-clusters. This result is about 6-7 times higher than that of M-cluster formation in Muse cell-enriched cell fractions and about 60 times higher than that of M-cluster formation in naive cell fractions. Meanwhile, M-cluster formation was not observed in SSEA-3 (–) cell fractions. Of note, in clonally expanded cells (3000 to 5000 cells) from a single cell cluster derived from a FACS-sorted SSEA-3(+) cell fractions, about 45% of the cells were SSEA-3(+) (FIG. 15-1a). This finding suggested that asymmetric cell division is involved in M-cluster formation and that this can also be said in clonal expansion of a single M-cluster. Actually Numblike (known to be involved in asymmetric cell division) exists in only one of the two daughter cells after cell division (FIG. 15-2b). These results suggest that asymmetric cell division is involved in the growth of Muse cells.

Electron microscopy revealed the presence of nuclear deformities and vacuoles in the cytoplasm in SSEA-3 (–) cells from H-fibroblast fractions and H-MSC fractions sorted after LTT, indicating cell damage. Electron microscopy did not reveal clearly recognizable morphological differences between SSEA-3 (–) and SSEA-3(+) cells (FIGS. 15-3c and d). SSEA-3 (–)

The importance of SSEA-3 (+) cells was also demonstrated in the transplantation experiments. When SSEA-3 (–)

cell fractions were transplanted, very small number of cells were positive for the tissue markers compared to SSEA-3 (+) cell fraction transplantation.

The majority of SSEA-3(+) cells in Muse-enriched cell fractions expressed both Oct3/4 and Sox2, which were detected in the cytoplasm (FIGS. 15-4e and g), and a very small number of cells expressed in the nucleus (FIG. 15-4D). This result indicates that SSEA-3 can be a good marker for Muse cells. In contrast, in cells in M-clusters, Oct3/4 and Sox2 predominantly localized to the nucleus (FIGS. 7-2h and l). It is possible that this difference in the intracellular localization of the two markers reflects a difference in the cell status.

The possibility remains that Muse cells are artificially induced by LTT. As described above, the majority of Muse cells exist in the bone marrow's CD105(+) cell fraction. Furthermore, SSEA-3(+) cells also showed Muse cell properties. We therefore attempted to directly obtain Muse cells from adult human bone marrow aspirates by isolating them as SSEA-3/CD105 double-positive cells. Double-positive cells, which constituted 0.025% to 0.05% of bone marrow-derived mononuclear cells, were directly subjected to single-cell suspension culture without LTT. After 7 days, 11.4%±1.2% of the cells (corresponding to 0.003% to 0.005% of the mononuclear cells) formed M-clusters, which were ALP(+). Single M-clusters were then again expanded by adherent culture to 3000 cells and subsequently subjected to single-cell suspension culture. Of these cells, 33.5%±3.1% cells formed $2^{nd}$ generation M-clusters, and RT-PCR of the cells that expanded from a single M-cluster on gelatin-coated dishes indicated the expression of α-fetoprotein, GATA6, MAP-2, and Nkx2.5, suggesting that cells with properties consistent with those of Muse cells reside in adult human bone marrow.

As described above, non-stem cells were removed by exposure to stress conditions, so that stem cells could be enriched. Muse cells could be efficiently collected by LTT and the following sorting of SSEA-3 (+) cells. Muse cells expressed pluripotency markers, were positive for alkaline phosphatase staining, and formed M-clusters capable of differentiating into ectodermal, mesodermal, and endodermal cells. Also, Muse cells have no characteristics relating to tumorigenic proliferation and no telomerase activity, as revealed by measurement of the growth rate. This suggests that Muse cells have a multi-layered safety system that prevents a burst in proliferation. Such non-tumorigenic property of Muse cells was also confirmed by an experiment wherein Muse cells were injected into mouse testes. This property is convenient for maintaining the balance of biofunctions. Absence of such property may destroy a living body due to abnormal growth or dysplasia, resulting in tumorigenesis or teratoma formation.

The pluripotency of Muse cells did not become obvious in an adherent culture system, but was observed in suspension culture.

In general, it is thought that Muse cells are in a dormant state, but are activated in response to signals related to an acute crisis or to continued stressful conditions such as a severe injury, starvation, or ischemia. Upon activation, Muse cells may contribute to tissue regeneration, intercellular interactions, and thus tissue organization.

Example 2

Characterization of Muse Cells Isolated Using SSEA-3

Examination in Example 1 revealed that SSEA-3 (+) cell fractions obtained by FACS had the properties of pluripotent stem cells; that is, they were Muse cells (J, K, and the like above). Furthermore, in vitro differentiation ability and in vivo differentiation ability were examined using isolated SSEA-3 (+) cells and then Muse-derived iPS cells were established.

1. Examination of In Vivo Differentiation Ability by Transplantation of Cells into Damaged Tissues SSEA-3 (+) Muse cells labeled with GFP (green fluorescent protein)-lentivirus were isolated and then transplanted via intravenous injection into immunodeficient mice (NOG mice) with damaged spinal cord (Crush injury of spinal cord), damaged liver (intraperitoneal injection of $CCl_4$, fulminant hepatitis model), or damaged gastrocnemius (muscle) (cardiotoxin injection). Human skin cell-derived Muse cells were labeled with GFP (green fluorescent protein)-lentivirus (Hayase M et al., J Cereb Blood Flow Metab. 29(8): 1409-20, 2009) and then it was confirmed using GFP that M-clusters were derived from the labeled cells. Crush injury of spinal cord was performed at the level of Th9 (Farooque M et al., Acta Neuropathol., 100; 13-22, 2000) for NOG mice. Cardiotoxin was injected into the gastrocnemius (muscle) of the NOG mice to induce muscle degeneration. Carbon tetrachloride was administered to NOG mice by peritoneal injection to induce liver degeneration. $1 \times 10^5$ Muse cells were transplanted by intravenous injection 2 days after for the muscle and liver and 7 days after for the spinal cord. Six mice were used for each condition. Intact mice that received intravenous injection of GFP-labeled MEC population were used as controls. At 3 or 4 weeks after transplantation, mice were fixed with 4% paraformaldehyde and then subjected to immunohistochemical analysis and confocal laser microscopic observation.

Figures 1, 16:
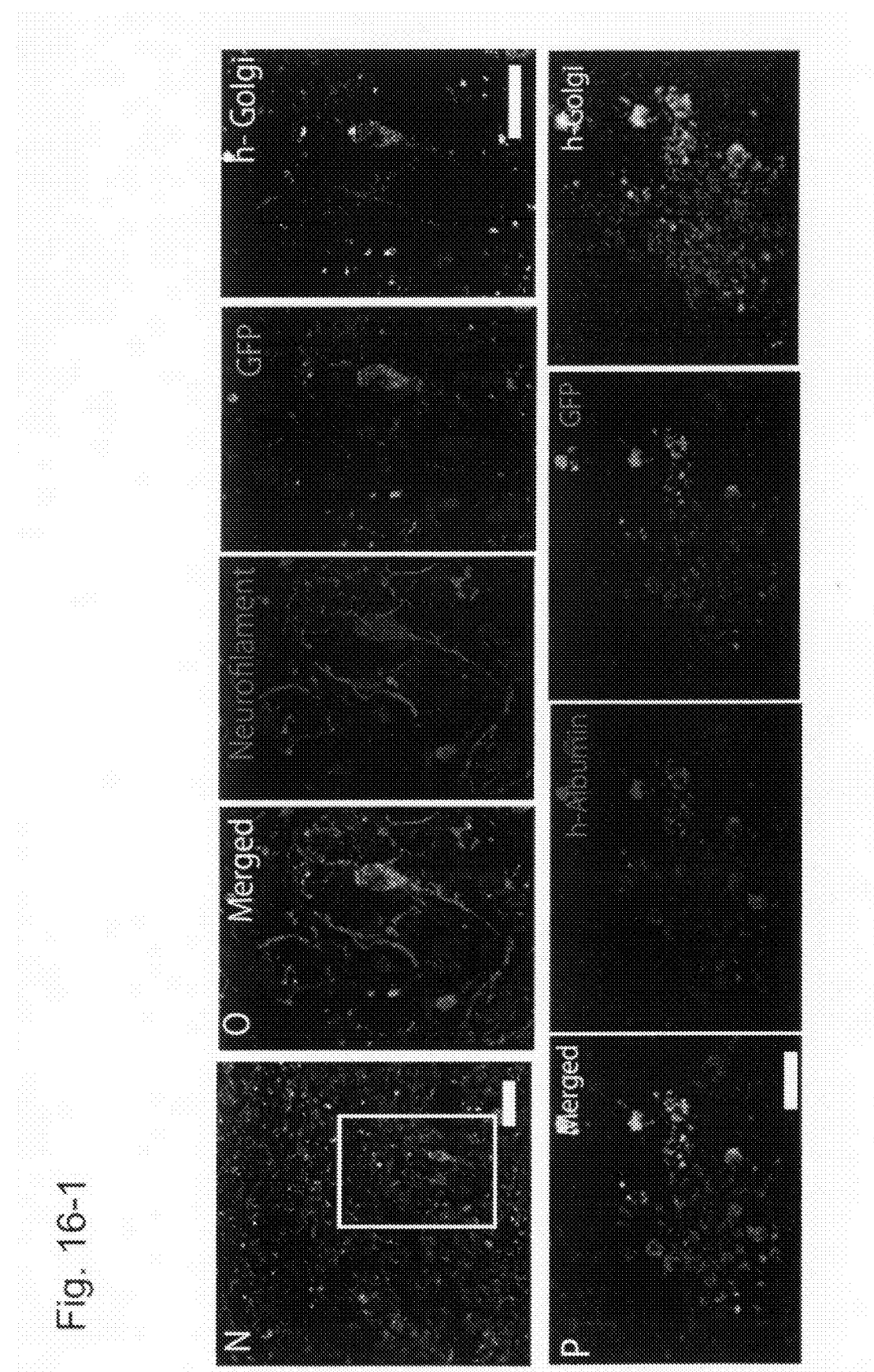
Figures 3, 16:
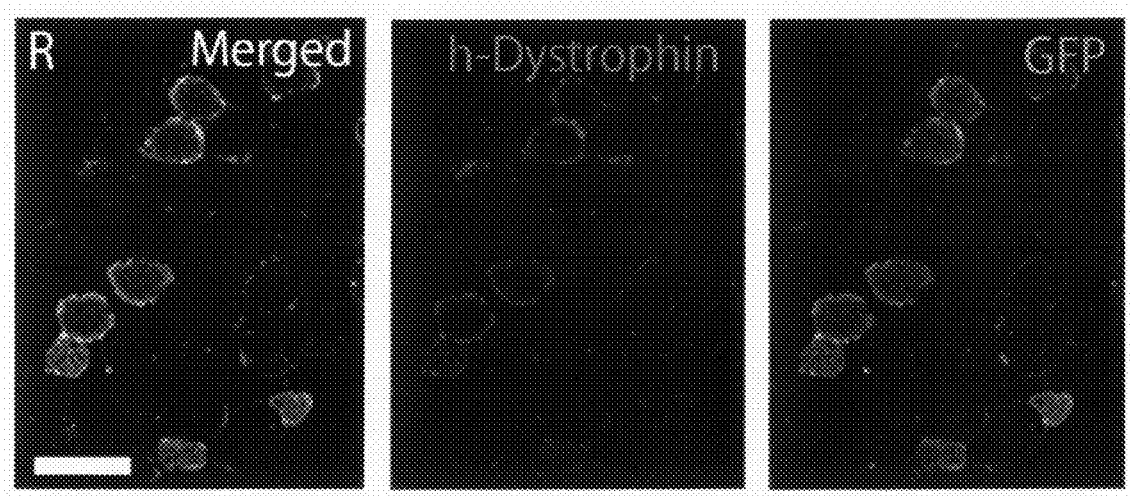

After 4 weeks, in mice with spinal cord injury, it was found that: cells positive for GFP and human Golgi complex expressed neurofilaments (FIG. 16-1N and O); and that in mice with liver damage, cells positive for GFP and human Golgi complex (in regenerated liver) expressed human albumin (FIG. 16-1P). RT-PCR further confirmed the expression of human albumin in Muse cell-transplanted NOG mice liver (FIG. 16-2). GFP(+) cells injected into the regenerating muscle and at 3 weeks expressed human dystrophin (FIG. 16-3). In contrast to these results, transplantation of SSEA-3(−) human dermal fibroblast fractions resulted in a significantly smaller number of integrated cells and fewer cells that were positive for the respective tissue markers. These findings suggest that Muse cells have an ability to integrate into damaged tissues and also to differentiate in vivo into ectodermal-, endodermal-, and mesodermal-lineage cells.

2. Differentiation of Expanded Cells Derived from M-Cluster Generated from Single Muse Cells It was examined whether an induction system is effective for regulation of differentiation of Muse cells. Single SSEA-3(+)-Muse cell-derived M-clusters were transferred individually to adherent culture for expansion. Expanded cells derived from a single Muse cell were collected, divided into four populations, and then each subjected to neural, osteocytes, adipocytes and hepatocyte inductions (n=5).

For neural induction, cells at a density of $1.0 \times 10^5$ cells/ml were cultured in NEUROBASA1 medium (Gibco) supplied with B-27 Supplement in poly-HEMA coated dish and cultured for 7 days for sphere formation. For differentiation, spheres were transferred onto poly-L-Lysin-coated glass, and incubated in 2% FBS supplied with 25 ng/ml FGF and 25 ng/ml BDNF for 10 days.

For osteocyte induction, cells at a density of $4.2 \times 10^3$ cells/$cm^2$ were incubated with osteocyte induction medium of Human Mesenchymal Stem Cell Functional Identification Kit (R&D Systems, SC-006) for 14 days.

For adipocyte induction, cells at a density of $2.1\times10^4$ cells/cm$^2$ were incubated with adipocytes induction medium of the human mesenchymal stem cell functional identification kit (R&D Systems) and incubated for 14 days.

For hepatocyte induction, cells at a density of $2.0\times10^4$ cells/cm$^2$ were incubated with DMEM (+10% FBS, 10×ITS (GIBCO) supplied with 10 nM dexamethasone and 100 ng/ml HGF, 50 ng/ml FGF4) on collagen-coated dish for 14 days.

Figures 1, 17:
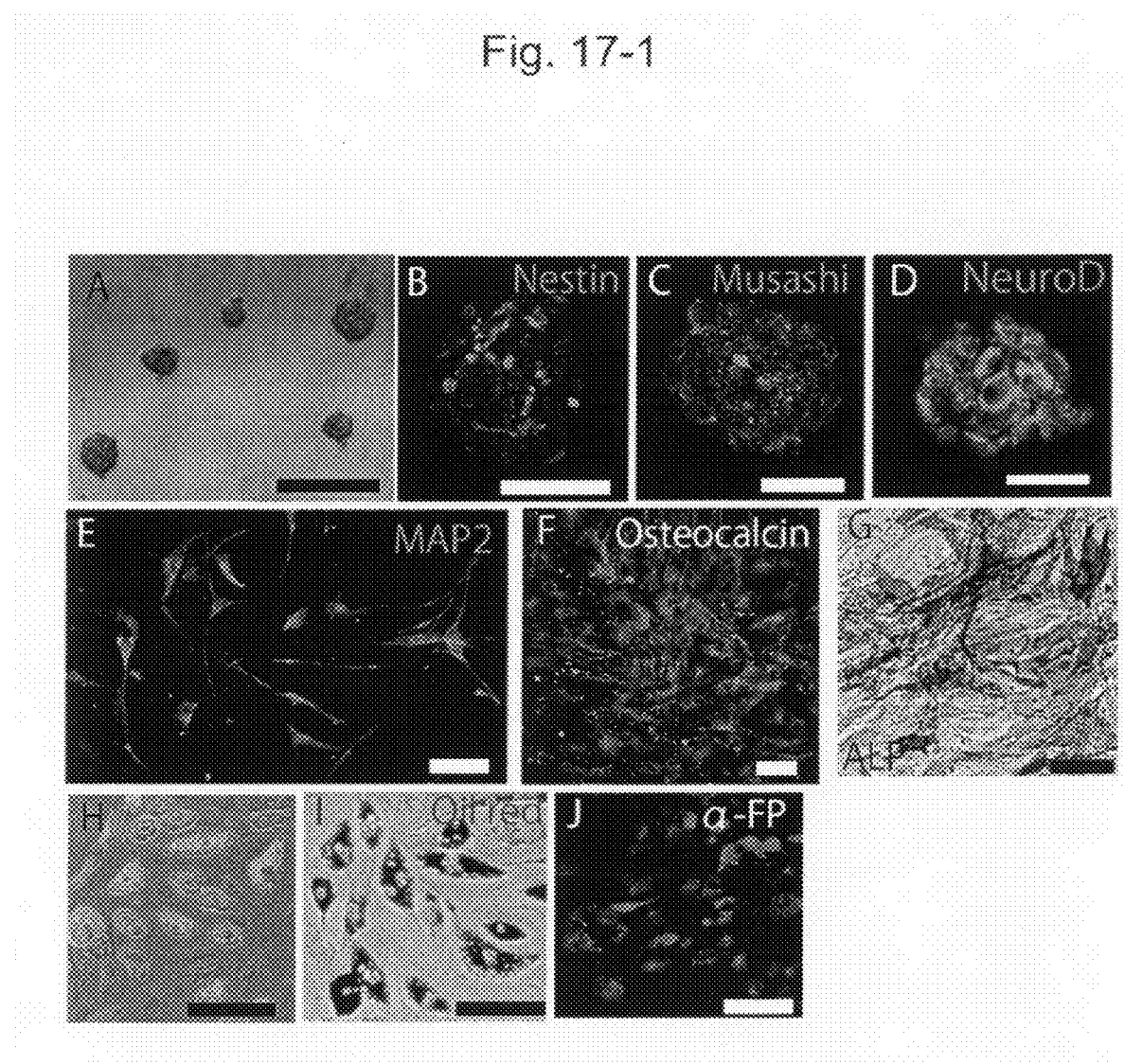

Neural induction generated spheres containing cells positive for neural stem cell markers nestin, Musashi and NeuroD (FIGS. 17-1A-D), which further differentiated into MAP-2- or GFAP-positive cells when cultured in differentiation medium (FIG. 17-1E; 89±5.7% positive either for MAP-2 or GFAP). Osteocyte induction produced cells positive for osteocalcin (97±3.5%) and alkaline phosphatase (FIGS. 17-1F-G). Adipocyte differentiation produced cells with lipid droplets that stained with oil red (90±4.9%) (FIGS. 17-1H-I). Hepatocyte induction generated cells positive for human α-fetoprotein (FIG. 17-1J; 87±7.6%), and RT-PCR confirmed the expression of human albumin and α-fetoprotein (FIG. 17-2). These results demonstrate that Muse cells can be regulated (via induction) to differentiate into cells of three lineages with very high efficiency.

3. Collection of SSEA-3 (+) Cells from the Adult Human Skin

It was attempted to directly isolate Muse cells from adult human skin without incubation of cultured cells or formation of M-clusters.

Human skin from healthy donors (n=3) was obtained from BIOPREDIC

International. The epidermis and fat tissues were carefully removed to separate the dermis, and the dermis was incubated with Collagenase/Dispase in α-MEM containing 10% FBS for 36 hrs at 37° C. Cells were collected by filtering digested dermis, and were subjected to centrifugation at 1500 rpm for 20 min, washed with α-MEM and incubated with 0.25% trypsin-HBSS for 5 min. Cells were further washed with FACS buffer, and incubated with SSEA-3 for collecting SSEA-3 (+) cells by cell sorting using FACS. From about 7 cm$^2$ of the skin tissue, $1.3\pm0.3\times10^4$ single cells could be finally collected. SSEA-3(+) cells accounted for 1.7±0.2% of these collected single cells.

21.0±1.7% of SSEA-3(+) cells formed M-clusters within 7 days of single-cell suspension culture by limiting dilution. The M-clusters were positive for ALP staining, and RT-PCR showed that cells expanded from a single M-cluster on gelatin-coated dishes expressed MAP-2, Brachyury, Nkx2.5, GATA6, and α-fetoprotein. These findings suggest that adult human dermis contains cells with the same properties as those of Muse cells as in the case of adult human bone marrow aspirates.

Human adult dermis contains several types of stem or progenitor cells, such as SKPs (skin-derived progenitor cells), NCSCs (neural crest stem cells), melanoblasts (MBs), perivascular cells (PCs), endothelial progenitors (EPs) and adipose-derived stem cells (ADSCs). To rule out a possibility that Muse cells are identical to one of these known stem cells, Muse cells were analyzed for expression of Snail (markers for SKPs), Slug (markers for SKPs), Sox10 (markers for NCSCs), CD271 (markers for NCSCs), Tyrp1 (markers for MBs), Dct (markers for MBs), CD117 (markers for MBs), CD146 (markers for PCs and ADSCs), NG2 (markers for PCs), CD34 (markers for EPs and ADSCs), and von Willebrand Factor (markers for EPs). None of these markers were detected in SSEA-3(+) cells by FACS or RT-PCR analysis (FIG. 18-1 and FIG. 18-2), suggesting that Muse cells differ from these stem or progenitor cells known to be present in adult human dermis.

Figures 2, 18:
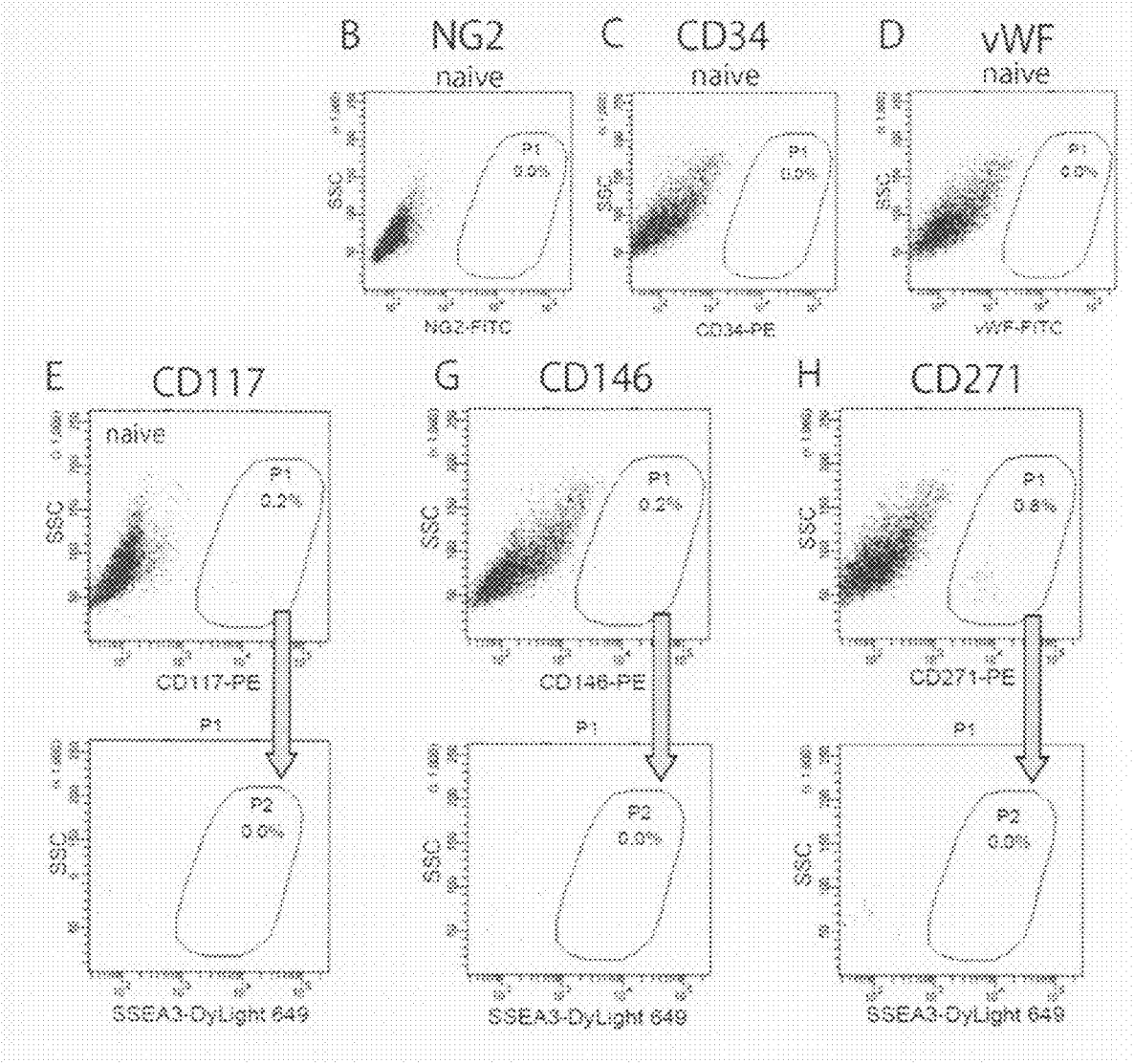
Figures 3, 18:
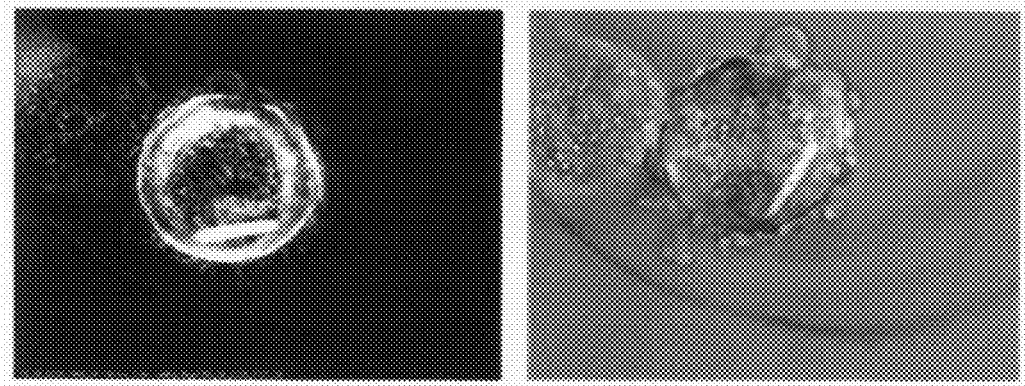

Phagocytic activity of Muse cells was determined using ferrite particles. Muse cells easily incorporated ferrite particles, suggesting that Muse cells have high phagocytic activity (FIG. 18-3).

4. Establishment of Muse-Derived iPS Cells (Muse-iPSC)

iPS cells are prepared by introduction of Oct3/4 gene, Sox2 gene, Klf4 gene, c-Myc gene, Nanog gene, and Lin28 gene, for example. Muse cells have properties analogous to iPS cells in that they express pluripotency markers and can differentiate into ectodermal, mesodermal, and endodermal cells. It was examined if Muse cells could be good materials for iPS cells.

A method employed for this purpose is as follows.

Four factors (Nanog, Oct3/4, KLF4, and c-Myc) were introduced into SSEA-3(+) cells and SSEA-3 (−) cells from H-fibroblast fractions using retroviral vectors according to the description of Takahashi et al., Cell, 131, 861-872 (2007) and then cultured. The method is specifically described as follows.

Establishment of Plasmid

The open reading frames of human Oct3/4, Sox2, Klf4, and c-Myc were inserted into the pMXs retroviral vectors (Cell Biolabs).

Infection with Retrovirus and Establishment of iPS Cells

PLAT-A cells were seeded at a density of $5\times10^6$ cells per 100-mm dish and then cultured overnight. On the next day, transfection was performed using Fugene HD. At 24 hours after transfection, medium exchange was performed. Supernatants were collected after 3 days and then filtered through a 0.45-μm filter. Polybrene (4 μg/ml) was then added. NHDFs (Normal Human Dermal Fibroblasts) seeded at a density of $1\times10^5$ cells per 60-mm dish were infected with a virus solution. 24 hours later, the medium was exchanged with new medium containing no virus. Cells were removed using trypsin on day 4 after viral infection and then seeded on MEF (feeder cells) at a density of $3\times10^4$ cells. On the next day, the medium was exchanged with Primate ES medium supplemented with 4 ng/ml bFGF. After 2 days, medium exchange was performed once every other day. After 30 days, colonies were picked up and then seeded over a 24-well plate.

PCR Analysis

RNA was purified using an RNeasy mini kit (QIAGEN). RNA (500 ng) was reverse transcribed using SuperScriptII. Endogenous Oct, Sox2, Klf4, Myc, and Nanog primers, PCR conditions, and the like are as described in Takahashi et al., Cell, 131, 861-872 (2007).

In Vitro iPS Cell Differentiation iPS cells were collected using collagenase. Cell clusters were placed on dishes coated with Poly-HEMA and then cultured in DMEM/F12 medium containing 20% Knockout serum replacement (Invitrogen), 2 mM L-Glutamine, $1\times10^-$4M nonessential amino acid, $1\times10^{-4}$M 2-mercaptoethanol (Nacalai), and 0.5% Penicillin/Streptomycin. Medium was exchanged once every other day. 7 days later, embryoid bodies were seeded on gelatin-coated dishes, followed by 1 week of culture in the same medium.

Formation of Teratomas iPS cells in a 60-mm diSh were treated with a Rock inhibitor, collected using Accutase (registered trademark) in a tube, subjected to centrifugation, and then suspended in PBS. These cells were injected into the testis of an NOG mouse (registered trademark) (Central Institute for Experimental Animals). After 12 weeks, the resultants were fixed with 4% paraformaldehyde. Paraffin sections were subjected to HE (Hematoxylin & Eosin) staining.

The following results were obtained.

Figure 19:
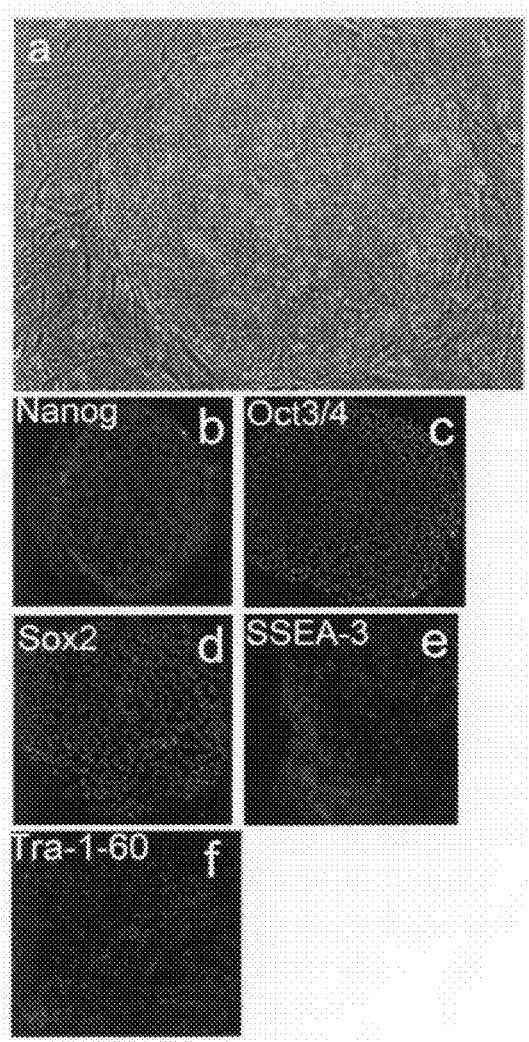
FIG. 19 shows photos showing the formation of iPS cells prepared from Muse cells.
Figure 20:
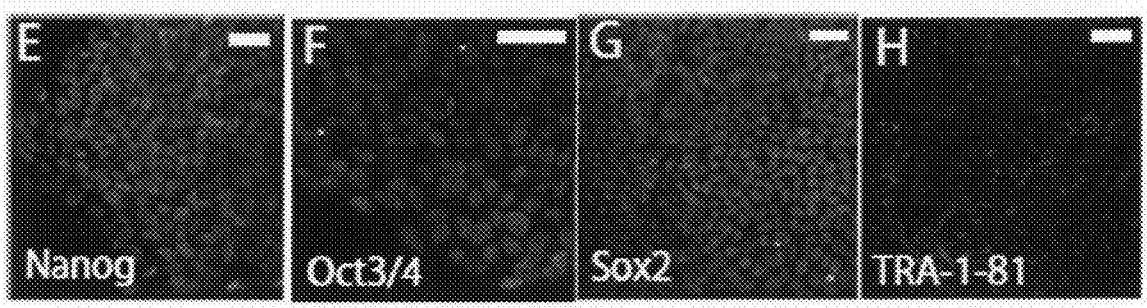
FIG. 20 shows photos showing the results of immunohistochemical analysis for Nonog (E), Oct3/4 (F), Sox2 (G), and Tra-1-81 (H).
Figure 21:
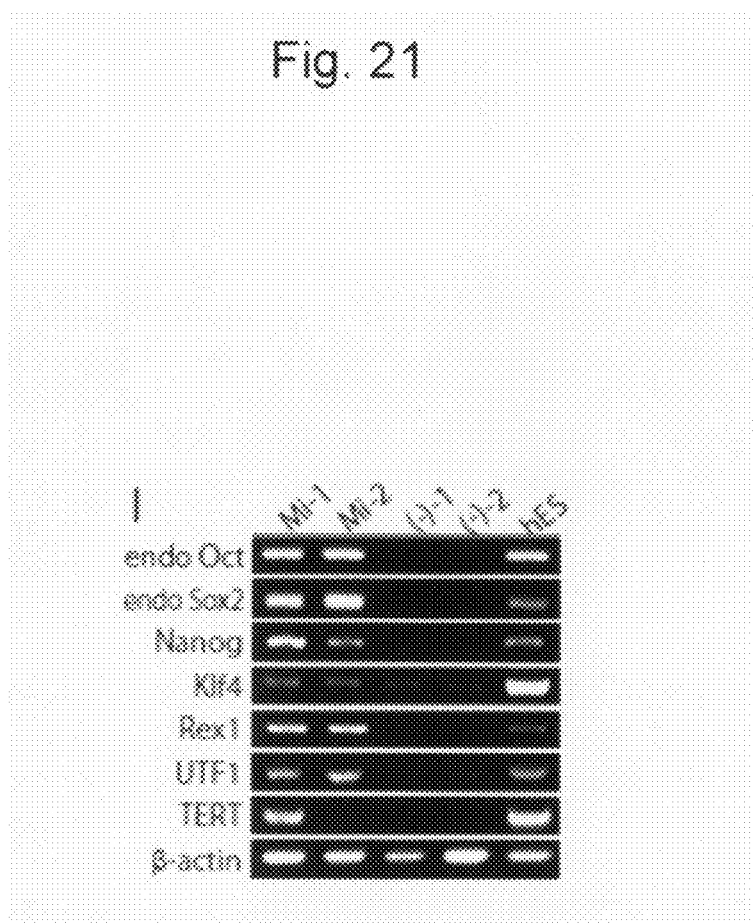
FIG. 21 shows photos showing the expression of pluripotency markers in colonies ((−)-1 and (−)-2) that grew from Muse-derived iPS cells (Mi-1 and Mi-2) and SSEA-3 (−) cells, as examined by RT-PCR.

Four factors, Nanog, Oct3/4, KLF4 and c-Myc were introduced into H-fibroblast fraction-derived SSEA-3(+) and (−) cells using retroviral vectors according to the method described by Takahashi et al, Cell, 131, 861-872 (2007). Cells were seeded again on MEF after 5 days, and then cultured. Immediately before colony pickup; that is, on day 30 of culture on MEF, the generated colonies in SSEA-3 (−) cells were non-ES cell-like colonies and none of them were positive for Tra-1-80 (ES cell marker). In contrast, many SSEA-3(+) cells formed colonies about sevenfold the number of colonies formed by SSEA-3(−) cell populations, which were positive for Tra-1-80. Importantly, genes tightly related to pluripotency, such as Nanog and Sox2 were all negative in SSEA-3 (−) cells (all colonies and cells not forming colonies were collected) even immediately before colony pickup on day 30 on MEF, as determined by RT-PCR. Meanwhile, SSEA-3(+) cells showed up-regulation of endogenous Oct3/4, KLF4, and Rex1 and expressed Nanog and Sox2. As expected, SSEA-3(+) cells were subjected to colony pickup and then transferred onto new MEF (feeder cells), iPS cells could be successfully generated at efficiency about 30 times higher than that of naive H-fibroblast fraction cells. These iPS cells exhibited up-regulation or new appearance of Tra-1-60, Tra-a-80, Rex1, UTF-1, telomerase reverse transcriptase (TERT) and factors expressed in human ES cells, as revealed by immunocytochemistry, RT-PCR, and Q-PCR (FIGS. 19 and 21). Furthermore, Nanog, Oct3/4, Sox 2, and TRA-1-81 were expressed in the thus obtained Muse cell-derived iPS cells (FIG. 19). RT-PCR revealed that Nanog, Oct3/4, and Sox 2 were expressed in Muse cell-derived iPS cells, but not expressed in SSEA-3 (−) cell-derived colonies (FIG. 21).

Figures 1, 22:
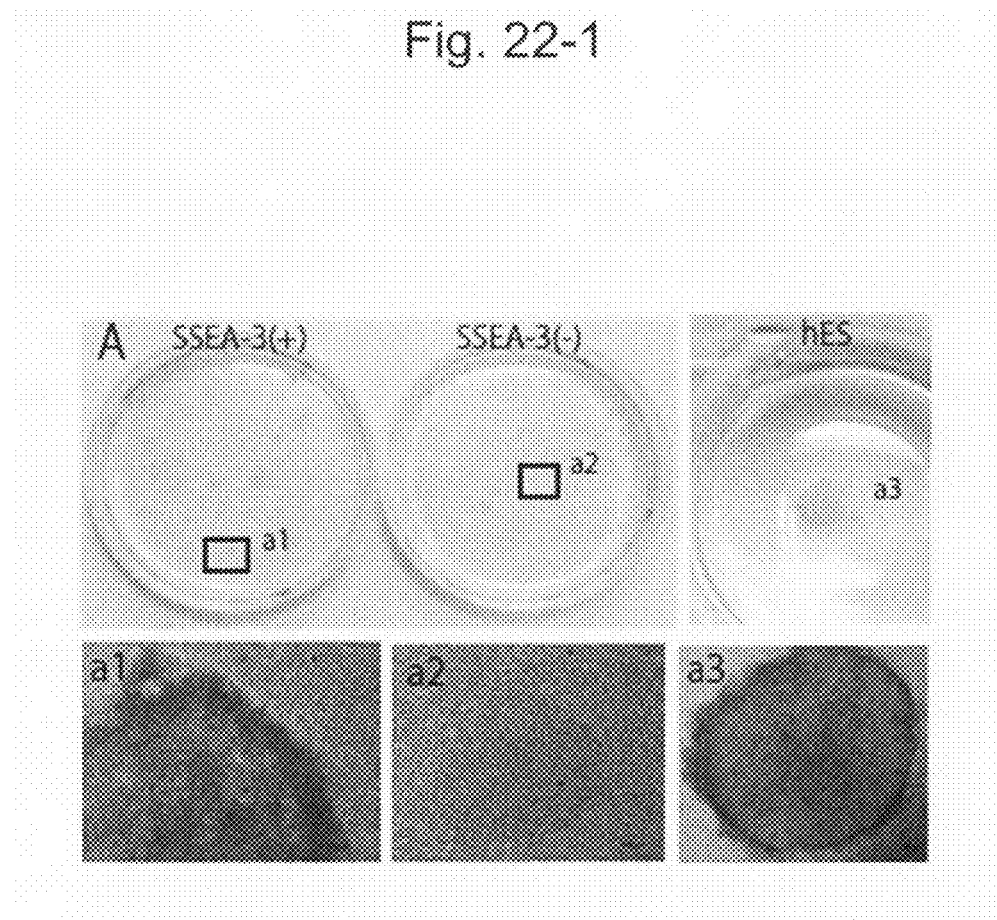
Figures 3, 22:
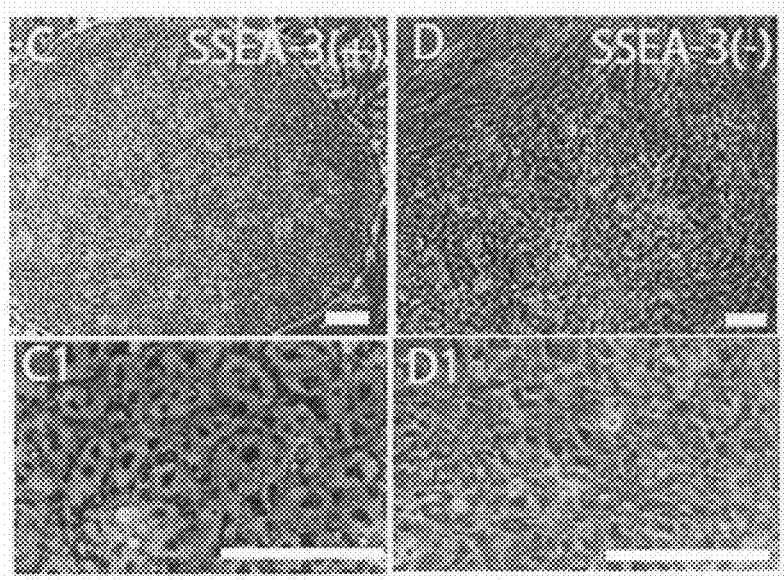

The efficiencies for transduction of Oct3/4 gene, Sox 2 gene, Klf4 gene, and c-Myc gene were almost identical for the SSEA-3(+) and SSEA-3(−) cell fractions. Transduced cells with above four factors were then transferred onto and cultured on mouse feeder cells at a density of $1 \times 10^5$ cells per dish. The generation of colonies were observed in both populations, but SSEA-3(+) cell fractions formed seven times more colonies than the SSEA-3 (−) cells. Furthermore, in contrast to those derived from the SSEA-3(+) cell fractions, none of the colonies derived from the SSEA-3 (−) cell fractions were found to be positive for the human pluripotent stem cell marker TRA-1-81 even on day 30 of culture immediately before colony pickup (FIG. 22-1). RT-PCR revealed that endogenous Sox2 and Nanog were only expressed in SSEA-3(+) cell-derived fractions but not in SSEA-3(−) cell fractions (FIG. 22-2).

All colonies generated from SSEA-3(+) and SSEA-3 (−) cell fractions were picked and passaged in individual wells to establish iPS cell lines. After 3 passages, all colonies exhibiting human ES cell-like morphology (flat colonies) were individually subjected to RT-PCR (FIGS. 22-3C and C1). Colonies expressing all three factors (endogenous Oct3/4, endogenous Sox2 and Nanog) were counted iPS colonies. This analysis revealed that only colonies originating from SSEA-3(+) cells generated iPS cells and the efficiency was 0.03%, while none of the colonies originating from SSEA-3 (−) cells generated iPS cells (FIG. 22-3D and D1).

Figures 1, 23:
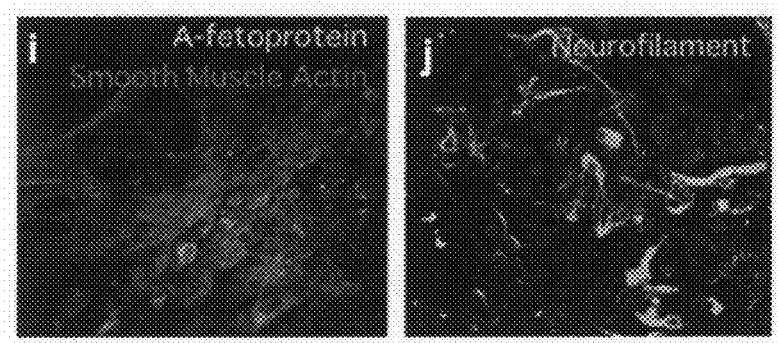
Figures 3, 23:
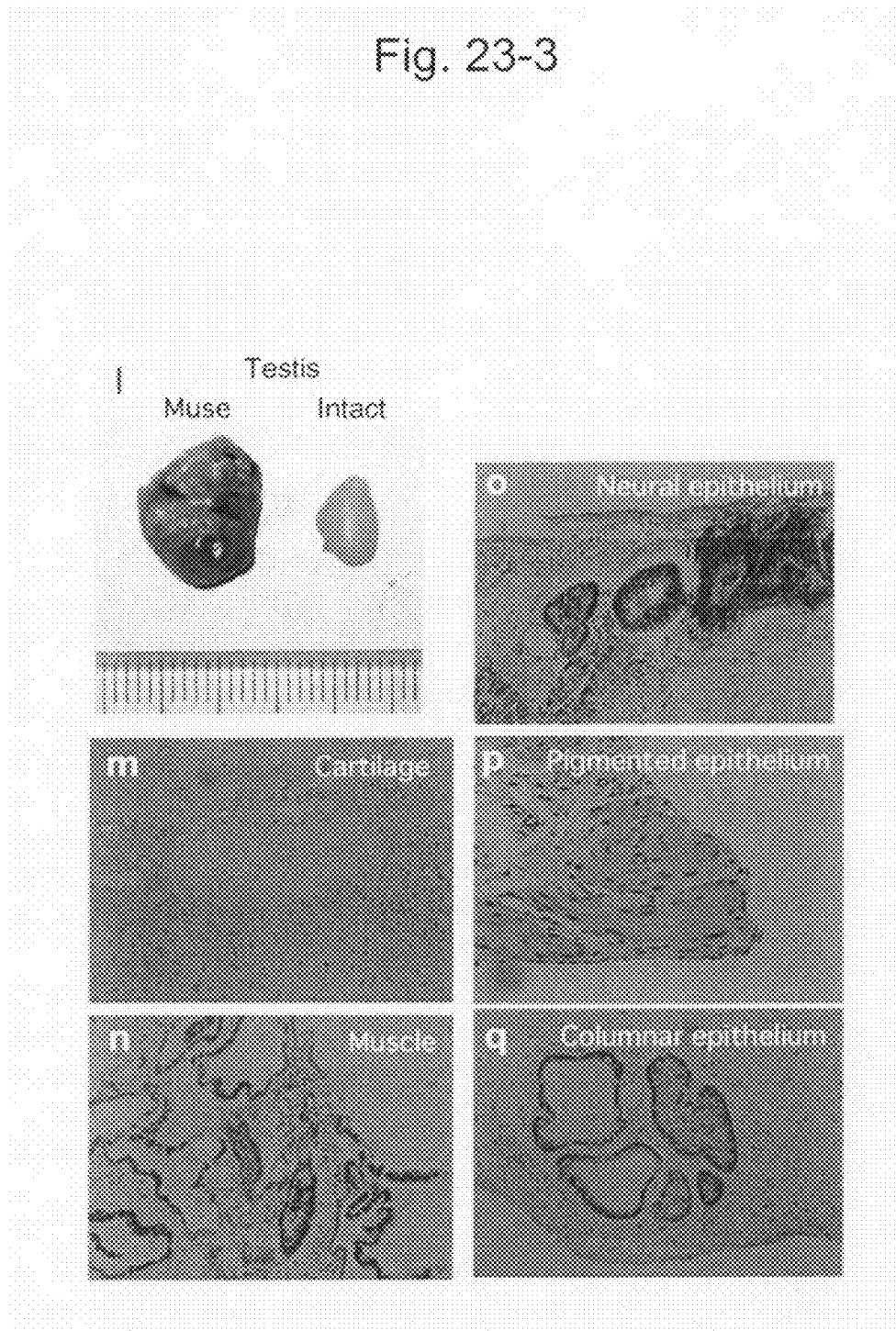

Furthermore, iPS cells established from Muse cells differentiated into ectodermal, mesodermal, and endodermal cells, and formed teratomas in mice testes (FIGS. 23-1 to 23-3).

The proliferation activity of Muse cells was not so high in terms of growth rate and telomerase activity. Consistently, while Muse cells differentiated into triploblastic cells in the mice testes, they did not develop into teratomas. This may be reasonable because if Muse cells are maintained in adult human tissue such as in skin and bone marrow, their proliferation should be strictly regulated, otherwise they would easily develop into tumors in virtually every part of the body. Moreover, even pluripotent cells do not always show teratoma formation since epiblast stem cells cultured under certain conditions were demonstrated not to form teratomas in mice testes (Chou et al., Cell, 135, 449-461 (2008)). As Muse cells originally showed some of the characteristics of pluripotent cells such as pluripotency marker expression and their differentiation ability, it is suggested that Muse cells could easily become iPS cells solely by an elevation of proliferative activity and formed teratoma in the mice testes. The induction mechanism of iPS is not yet clarified, but procurement of tumorigenic proliferation in Muse cells among mesenchymal cell population might be one of the possibilities.

iPS cells could be established at efficiency of about 0.001% from naive human dermal fibroblast fractions. This agrees with the report of K. Takahashi et al., Cell 131, 861 (2007). Therefore, iPS cell preparation efficiency from SSEA-3 (+) cells was 30 times higher than that from naive fibroblasts. This suggests that Muse cells mainly contribute to iPS cell generation.

Immunohistochemical analysis and RT-PCR analysis of embryoid bodies that developed from Muse-derived iPS cells showed that cells differentiated into ectodermal cells expressing neurofilament and MAP-2, mesodermal cells expressing SMA, Brachyury and Nkx2.5, and endodermal cells expressing α-fetoprotein and GATA-6 in vitro. Furthermore, injection of Muse-derived iPS cells into testes of immunodeficient mice resulted in teratoma formation. In contrast, testes injected with M-clusters did not develop teratomas for up to 6 months, and most were not significantly larger than control testes that were injected with inactivated MEFs. However, cells positive for human mitochondria, and for SMA, α-fetoprotein and neurofilament were identified. These results show that unlike Muse-derived iPS cells, original Muse cells do not form teratoma, but differentiate into mesodermal, ectodermal, and endodermal lineage cells in immunodeficient mice.

Figure 24:
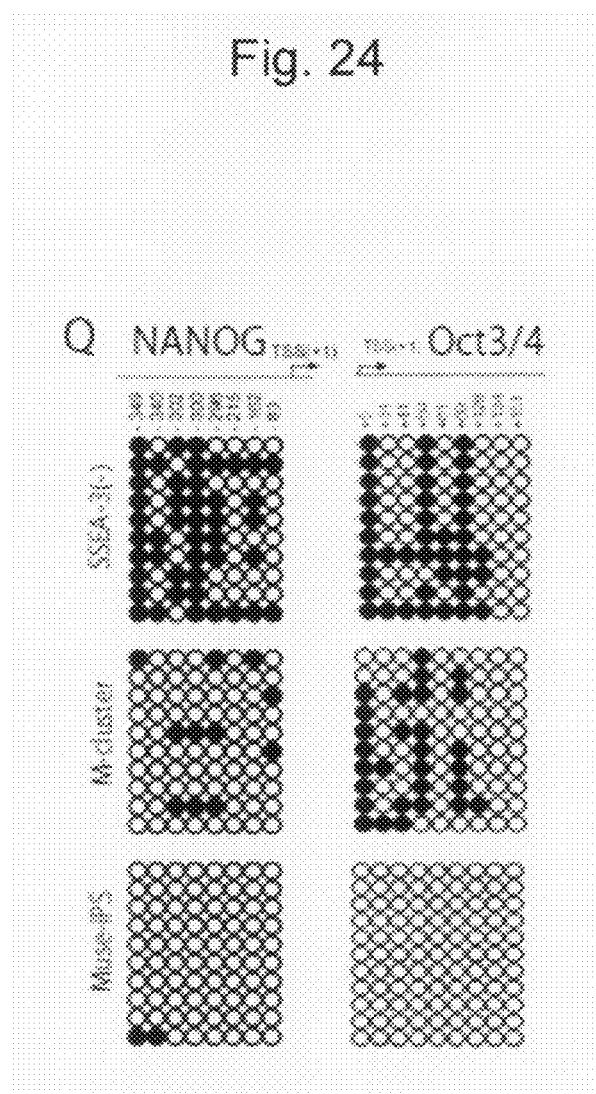
FIG. 24 shows the results of bisulfite (hydrogensulfite) sequencing for the Nanog gene and the Oct3/4 gene of SSEA-3 (−) cell fractions, M-clusters, and Muse-derived iPS cells. The numerical value in each column indicates the position of CpG downstream of the transcription start site (TSS). An open circle indicates unmethylated cytosine and a filled circle indicates methylated cytosine.
Figure 25:
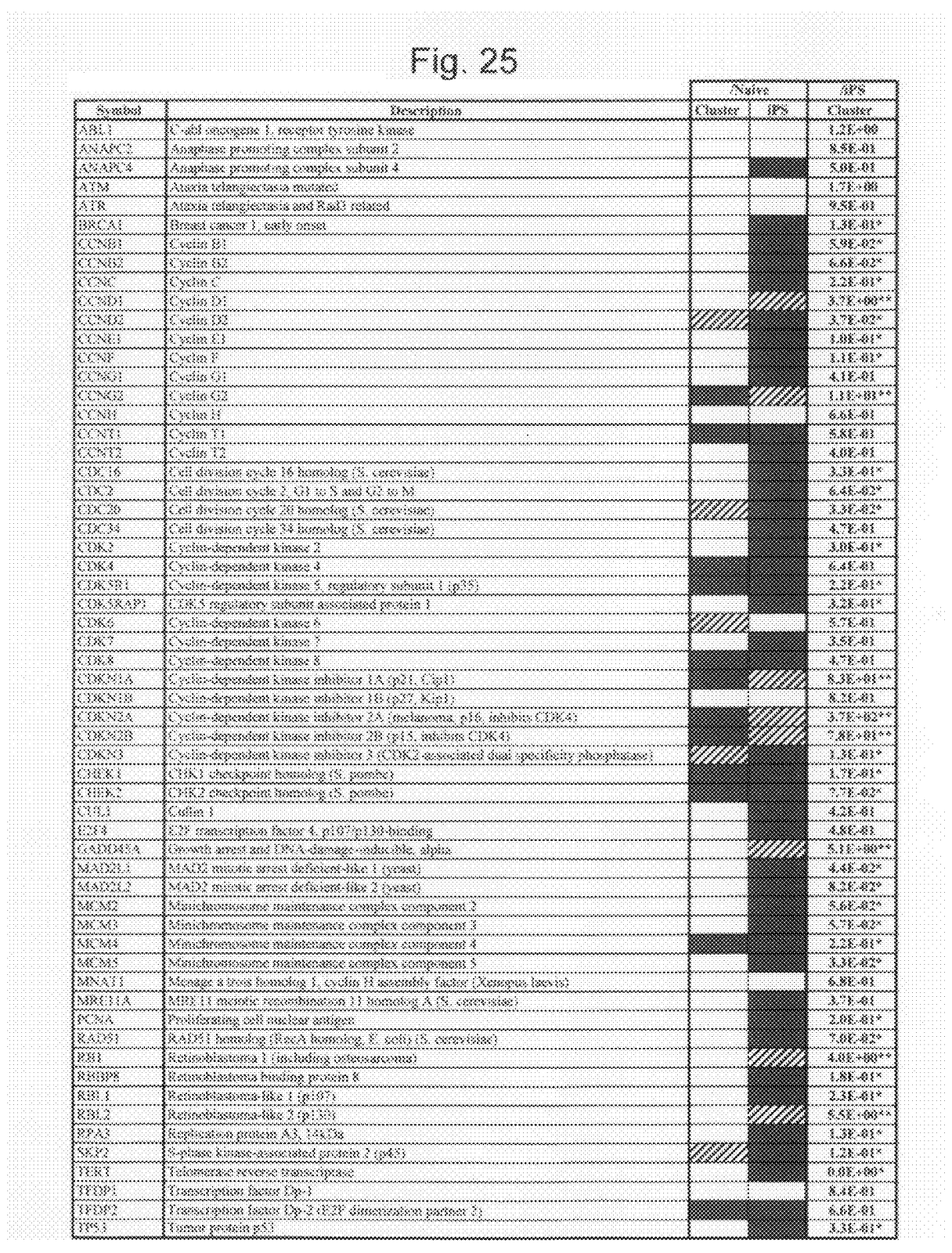

M-clusters and Muse-derived iPS cells were subjected to quantitative-PCR (Q-PCR). The results are shown in FIGS. 25 and 26. The expression patterns of genes related to cell cycle regulation differed substantially. Genes related to cell cycle progression were mostly down-regulated in M-clusters but up-regulated in Muse-derived iPS cells. Expression of genes related to pluripotency and an undifferentiated cell state were similar in M-clusters and Muse-derived iPS cells, but the expression levels of Nanog, Oct3/4 and Sox2 were much lower in M-clusters than in Muse-derived iPS cells. Furthermore, cytosine guanine dinucleotides (CpGs) in the promoter regions of Nanog and Oct3/4 genes were less methylated in Muse-derived iPS cells than in M-clusters, and the promoter region of Nanog gene showed a lower CpG methylation level in M-clusters than in naive SSEA-3 (−) cell fractions (FIG. 24). This result may partly explain the differences in the expression level of pluripotency markers between Muse cells and Muse-derived iPS cells.

INDUSTRIAL APPLICABILITY

According to the present invention, pluripotent stem cells can be obtained from body tissue without using any germ cells or early embryos and without using an artificial induction operation such as foreign gene transfer or introduction of a specific compound. The pluripotent stem cells of the present invention can be efficiently prepared without using an artificial operation such as foreign gene transfer, so that they can be safely used when applied for treatment. Also, the pluripotent stem cells of the present invention can be used for regeneration medicine and treatment for dysfunctional tissue or the like, and they can be further used for research into cell division or tissue regeneration, for example.

All publications, patents, and patent applications cited in this specification are herein incorporated by reference in their entirety.

What is claimed is:

1. A method for enriching for human cells isolated from mesodermal or mesenchymal tissue of a living mammalian body, the method comprising
   (a) isolating human mesodermal or human mesenchymal cells that express SSEA-3 from human mesodermal or mesenchymal cells; and
   (b) collecting the SSEA-3 (+) human cells which comprise SSEA-3(+) human cells which are capable of forming cell clusters, the cell clusters including SSEA-3(+) human cells which:
      (i) exhibit low or no telomerase activity;
      (ii) are capable of differentiating into three germ layers;
      (iii) exhibit the lack of neoplastic proliferation;
      (iv) exhibit self-renewal capability;
      (v) are CD31 (−);
      (vi) are CD105(+); and
   (c) enriching the SSEA-3(+) human cells which exhibits (i) to (vi) above.

2. The method according to claim 1, wherein the human cell further has the following properties:
   (i) being negative for CD117 and negative for CD146;
   (ii) being negative for CD117, negative for CD146, negative for NG2, negative for CD34, negative for vWF, and negative for CD271;
   (iii) being negative for CD34, negative for CD117, negative for CD146, negative for CD271, negative for NG2, negative for vWF, negative for Sox10, negative for Snail, negative for Slug, negative for Tyrp1, and negative for Dct; and
   (iv) having low or no telomerase activity.

3. A method for enriching human cells isolated from mesodermal or mesenchymal tissue of a living mammalian body, the method comprising:
   (a) exposing a population of human mesodermal or human mesenchymal cells to cellular stress which is dispase or collagenase incubation;
   (b) collecting surviving cells which comprises at least 9% of human cells which can form cell clusters, the cell clusters including cells which comprise the following phenotypes:
      (i) are SSEA-3 (+);
      (ii) exhibit low or no telomerase activity;
      (iii) exhibit a lack of neoplastic proliferation;
      (iv) exhibit self-renewal capability;
      (v) exhibit a lack of CD31 expression or CD31 (−);
      (vi) are CD105(+); and
   (c) enriching the human cells which comprises phenotypes (i) to (vi) above.

* * * * *